United States Patent
Brousmiche et al.

(10) Patent No.: US 11,353,461 B2
(45) Date of Patent: Jun. 7, 2022

(54) METHODS OF ENHANCING MS DETECTION OF TAGGED GLYCANS

(71) Applicant: WATERS TECHNOLOGIES CORPORATION, Milford, MA (US)

(72) Inventors: Darryl W. Brousmiche, Grafton, MA (US); Matthew A. Lauber, North Smithfield, RI (US)

(73) Assignee: Waters Technologies Corporation, Medford, MA (US)

( * ) Notice: Subject to any disclaimer, the term of this patent is extended or adjusted under 35 U.S.C. 154(b) by 133 days.

(21) Appl. No.: 16/312,800

(22) PCT Filed: Jun. 19, 2017

(86) PCT No.: PCT/US2017/038119
§ 371 (c)(1),
(2) Date: Dec. 21, 2018

(87) PCT Pub. No.: WO2017/222975
PCT Pub. Date: Dec. 28, 2017

(65) Prior Publication Data
US 2019/0219587 A1    Jul. 18, 2019

Related U.S. Application Data

(60) Provisional application No. 62/483,015, filed on Apr. 7, 2017, provisional application No. 62/352,734, filed on Jun. 21, 2016.

(51) Int. Cl.
*G01N 33/00*    (2006.01)
*G01N 33/58*    (2006.01)
(Continued)

(52) U.S. Cl.
CPC ........... *G01N 33/582* (2013.01); *G01N 33/50* (2013.01); *G01N 33/6848* (2013.01);
(Continued)

(58) Field of Classification Search
CPC ..................................................... G01N 33/582
(Continued)

(56) References Cited

U.S. PATENT DOCUMENTS

2010/0261275 A1\* 10/2010 Durocher ............... C07K 14/56
435/369
2014/0179011 A1\* 6/2014 Brousmiche ......... C07D 207/46
436/89

(Continued)

FOREIGN PATENT DOCUMENTS

CN    105418586 A    3/2016
WO    2016069764 A1    5/2016

OTHER PUBLICATIONS

Lauber et al. "Rapid Preparation of Released N-Glycans for HILIC Analysis Using a Labeling Reagent that Facilitates Sensitive Fluorescence and ESI-MS Detection" Anal. Chem. 2015, 87, 5401-5409; plus Supporting Information (Year: 2015).\*

(Continued)

*Primary Examiner* — Christine T Mui
*Assistant Examiner* — Emily R. Berkeley
(74) *Attorney, Agent, or Firm* — Womble Bond Dickinson (US) LLP; Deborah M. Vernon

(57) ABSTRACT

Methods for derivatization of biomolecules including glycans or other biopolymers with one or more fluorescent, MS active compounds by reductive amination or rapid tagging in order to produce derivatized glycan having a pKa>7 and between about 200 Å$^2$ and about 1000 Å$^2$ of nonpolar surface area are described.

14 Claims, 25 Drawing Sheets

(51) Int. Cl.
    *G01N 33/50*     (2006.01)
    *G01N 33/68*     (2006.01)

(52) U.S. Cl.
    CPC ..... *G01N 2400/00* (2013.01); *G01N 2400/10* (2013.01); *G01N 2560/00* (2013.01)

(58) Field of Classification Search
    USPC .......................................................... 436/56
    See application file for complete search history.

(56) References Cited

U.S. PATENT DOCUMENTS

| | | | |
|---|---|---|---|
| 2014/0242709 A1* | 8/2014 | Brousmiche | G01N 33/582 436/94 |
| 2016/0139136 A1 | 5/2016 | Brousmiche et al. | |

OTHER PUBLICATIONS

International Search Report and Written Opinion for International application No. PCT/US17/38119, dated Sep. 11, 2017, 7 pages.

Extended European Search Report for Application No. EP1781600.1, dated Jan. 24, 2020, 8 pages.

Klapoetke, S., et al., "The evaluation of a novel approach for the profiling and identification of N-linked glycan with a procainamide tag by HPLC with fluorescent and mass spectrometric detection," Journal of Pharmaceutical and Biochemcial Analysis 53(3):315-324 (2010).

Walker, S., et al., "Hydrophobic Derivatization of N-linked Glycans for Increased Ion Abundance in Electrospray Ionization Mass Spectrometry," Journal of the American Society for Mass Spectrometry, 22(8):1309-1317 (2011).

Gustafsson, O.J. R., et al., "MALDI imaging mass spectrometry of N-linked glycans on formalin-fixed paraffin-embedded murine kidney," Analytical and Bioanalytical Chemistry, 407:2127-2139 (2015).

Author unknown, "Benzene" Molfield [online] Last updated, Feb. 21, 2014 [retrieved on Apr. 24, 2020]. Retrieved from Internet URL: http://asd.molfield.org/php/view_details.php?id=59, 2 pages.

Author unknown, "Compound Summary—Triethylamine" PubChem [online] Mar. 2005 [retrieved on Apr. 24, 2020]. Retrieved from Internet URL: https://pubchem.ncbi.nlm.nih.gov/compound/triethylamine#section=Top, 72 pages.

* cited by examiner

| COMPOUND | ANALOG OF LABEL MOIETY USED IN CALCULATIONS | ESTIMATED NON-POLAR SURFACE AREA | pKa OF LABEL MOIETY (NOT LINKAGE) |
|---|---|---|---|
| COMPOUND 1 | quinoline-2-carboxamide with N-ethyl diethylaminoethyl group | 222 Å² | 9 |
| COMPOUND 2 | benzamide | 69 Å² | N/A |
| COMPOUND 3 | quinoline | 108 Å² | 5 |
| COMPOUND 4 | N-(2-diethylaminoethyl)benzamide | 196 Å² | 9 |
| COMPOUND 5 | 2-(diethylamino)ethyl benzoate | 196 Å² | 9 |

FIG.9

METHODS OF ENHANCING MS DETECTION OF TAGGED GLYCANS

CROSS-REFERENCE TO RELATED APPLICATIONS

This application is a national phase filing claiming the benefit of and priority to International Patent Application No. PCT/US2017/038119, filed on Jun. 19, 2017, which claims priority to U.S. Provisional Patent Application No. 62/352,734 filed Jun. 21, 2016, incorporated herein by reference and U.S. Provisional Patent Application No. 62/483,015 filed Apr. 7, 2017, incorporated herein by reference.

STATEMENT REGARDING FEDERALLY SPONSORED RESEARCH OR DEVELOPMENT

None.

THE NAMES OF PARTIES TO A JOINT RESEARCH AGREEMENT

None.

BACKGROUND OF THE INVENTION

Analysis of glycans is used for protein research and can be important to clinical chemists and pharmaceutical manufacturers, especially where glycosylation profiling of proteins is monitored to ensure consistency of a therapeutic product. Therefore, fluorescent labeling of glycans is beneficial because the sensitivity and selectivity of glycan detection can be improved as well as the chromatographic behavior. However, upon derivatization with a reagent that provides a fluorescent moiety, the identity of the compound can only be speculated. Mass spectrometry ("MS") is required to identify the specific compound. Furthermore, certain tagging reagents have good fluorescence signal, but a poor MS signal.

There is a need, therefore, for methods for tagging glycans to provide both mass spectrometry and fluorescence signals through diverse sets of reaction conditions with reactivity to various functional groups that might be present in the glycan.

SUMMARY OF THE INVENTION

Methods of analyzing glycans via mass spectroscopy as well as fluorescence and ultraviolet ("UV") by tagging glycans, particularly N-linked glycan and O-linked glycans, using compounds of the various formulas are described herein. The methods described herein include derivatization of other biomolecules including proteins, peptides and/or biopolymers containing an aldehyde or ketone group, with one or more fluorescent, MS active compounds by reductive amination or rapid tagging to produce derivatized glycan having a pKa>7 and between about 200 Å$^2$ and about 1000 Å$^2$ of nonpolar surface area. The non-polar surface area can be used to estimate the hydrophobicity of a reagent. Furthermore, nonpolar surface area can be estimated as in the procedure described by Walker et. al., *Hydrophobic Derivatization of N-linked Glycans for Increased Ion Abundance in Electrospray Ionization Mass Spectrometry*, 22 J. AM. SOC. MASS SPECTROM. 1309 (2011). As the non-polar surface area or hydrophobicity of the reagent is increased, the signal of the derivatized glycan is increased.

Hence, the present methods use labeling moieties for reductive amination of glycans that are constructed to combine a high pKa (>7) basic residue with a functional group that affords comparatively significant non-polar surface area. Indeed, the combination of nonpolar surface area and high pKa is not restricted to compounds that are fluorescently active. Furthermore, nonpolar surface area can be combined advantageously with low pKa acidic moieties to enhance negative ion mode electrospray ionization mass spectrometry.

Also, provided are methods of tagging of glycans such as oligosaccharides, N-linked glycans, O-linked glycans and other biomolecules include, but not limited to, proteins and peptides that contain an aldehyde or ketone group, with the MS active fluorescent compounds described herein. The present methods provide for the analysis of tagged glycans via two different analytical methods, fluorescent and/or mass spectroscopic analysis. The analytical methods include: (a) tagging a glycan with a reagent to provide improved fluorescent signal in liquid chromatography, and (b) analyzing glycans tagged with a fluorescent and MS active compounds through reductive amination. Moreover, this methodology can be extended to capillary electrophoresis combined with fluorescence and MS detection.

In particular, the methods of tagging can use compounds of formulas described herein. Each compound can be the reagent for fluorescence and enhanced MS signaling. Generally, the MS active, fluorescence tagging compounds can be of the structural Formula I:

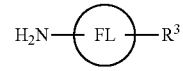

Formula I wherein
FL is a fluorophore such as a phenyl, quinoline, napthalene, coumarin or rhodamine compound.

More particularly, compounds of Formula I can be of any of the following structural formula, and salts or solvates thereof:

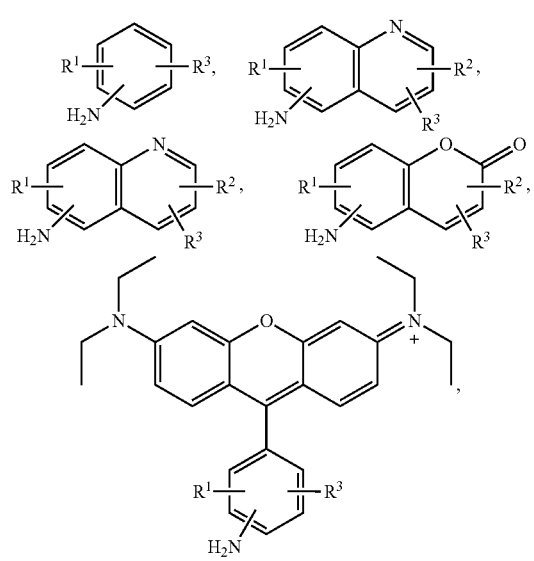

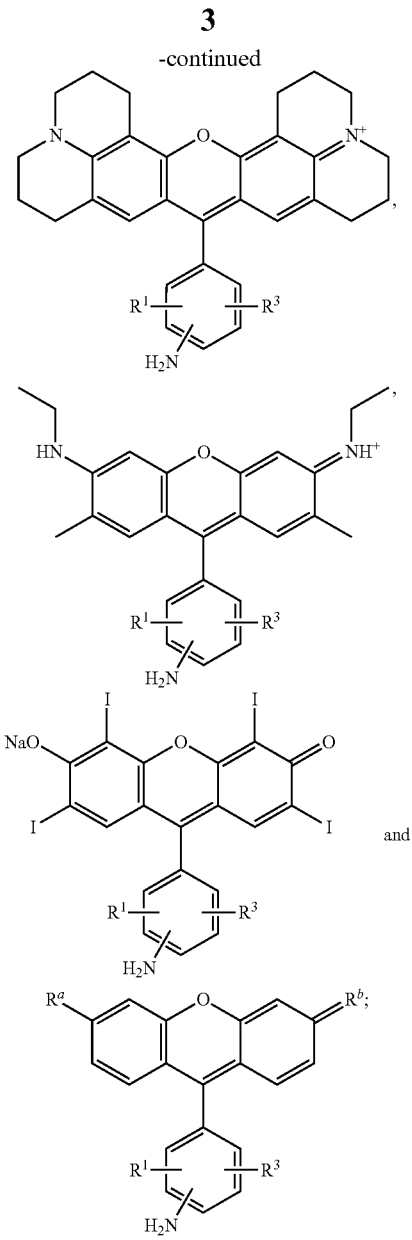

wherein each $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

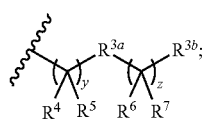

$R^{3a}$ is selected from ester, amide, amine, oxygen, urea, carbamate, carbonate, sulfur, thiourea, thiocarbamate, alkyl or carbonyl;

$R^{3b}$ is

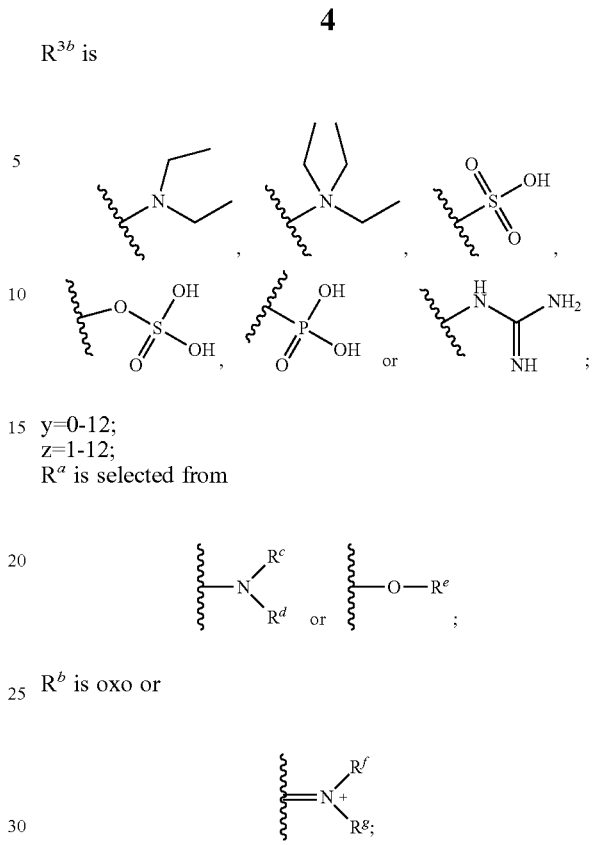

y=0-12;
z=1-12;
$R^a$ is selected from $R^b$ is oxo or and
$R^c$, $R^d$, $R^e$, $R^f$ and $R^g$ are independently selected from hydrogen and optionally substituted alkyl; and
each of $R^4$, $R^5$, $R^6$ and $R^7$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$.

Furthermore, the compounds described herein can have optical centers. Therefore, the compounds can occur in different enantiomeric and diastereomeric configurations. Stereoisomers of such compounds of each formula, as well as racemic compounds and racemic mixtures and other mixtures of stereoisomers thereof can occur.

BRIEF DESCRIPTION OF THE DRAWINGS

FIG. 2A shows HILIC fluorescence by 6-ADEQ and FIG. 2B shows base peak intensity MS chromatograms obtained for 6 pmoles of each type of labeled Man5 oligosaccharide with 6-ADEQ. FIG. 2C shows HILIC fluorescence by 2-AB and FIG. 2D shows base peak intensity MS chromatograms obtained for 6 pmoles of each type of labeled Man5 oligosaccharide with 2-AB.

FIG. 9 shows estimated non-polar surface area and pKa values of various tagging moieties.

DETAILED DESCRIPTION

Figure 1:
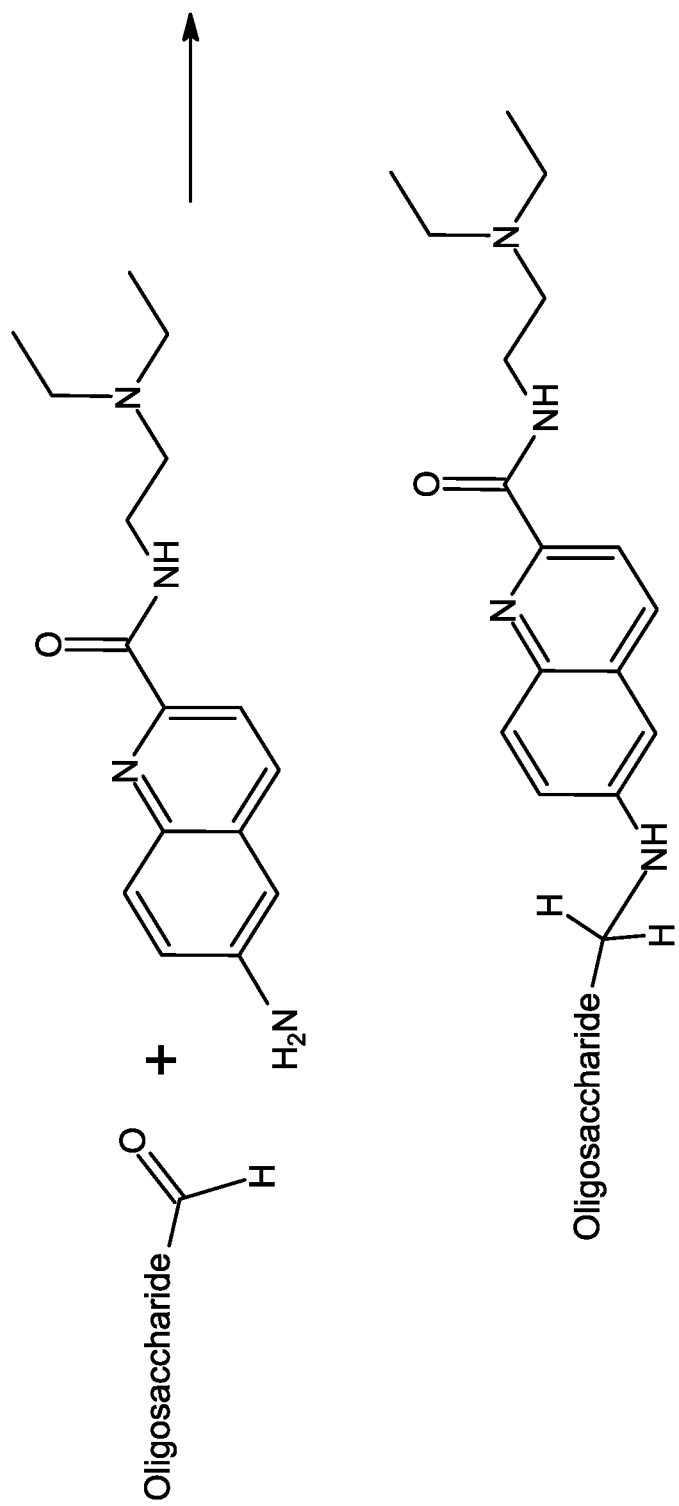
FIG. 1 shows chemical structure of a compound referred to as 6-ADEQ and a schematic for its use in reductive amination of an oligosaccharide.
Figure 2B:
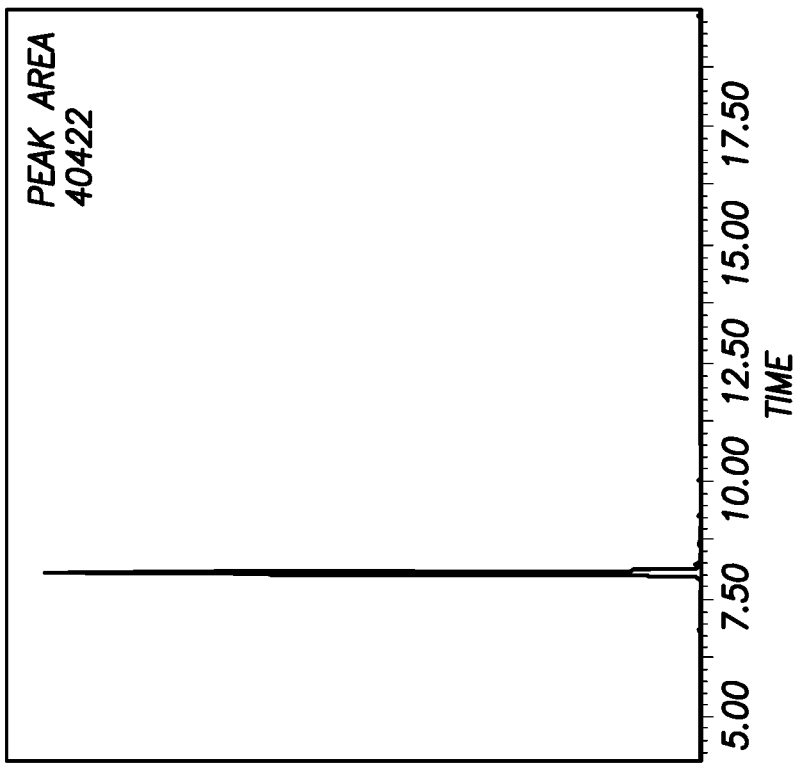
FIGS. 2A, 2B, 2C and 2D show a comparison of signal provided by 6-ADEQ versus 2-AB labeled Man 5 oligosaccharide.
Figure 2A:
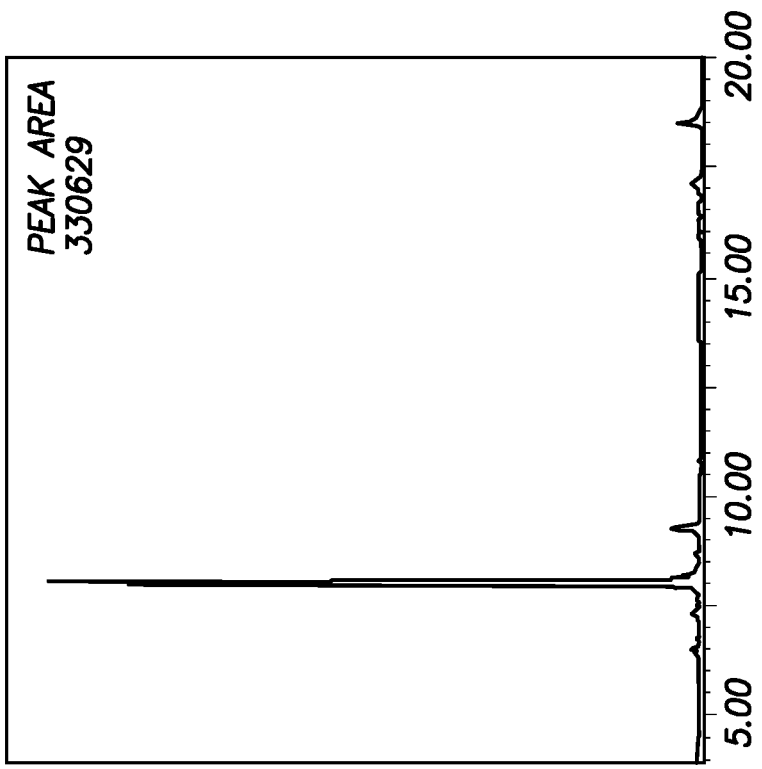
Figure 2D:
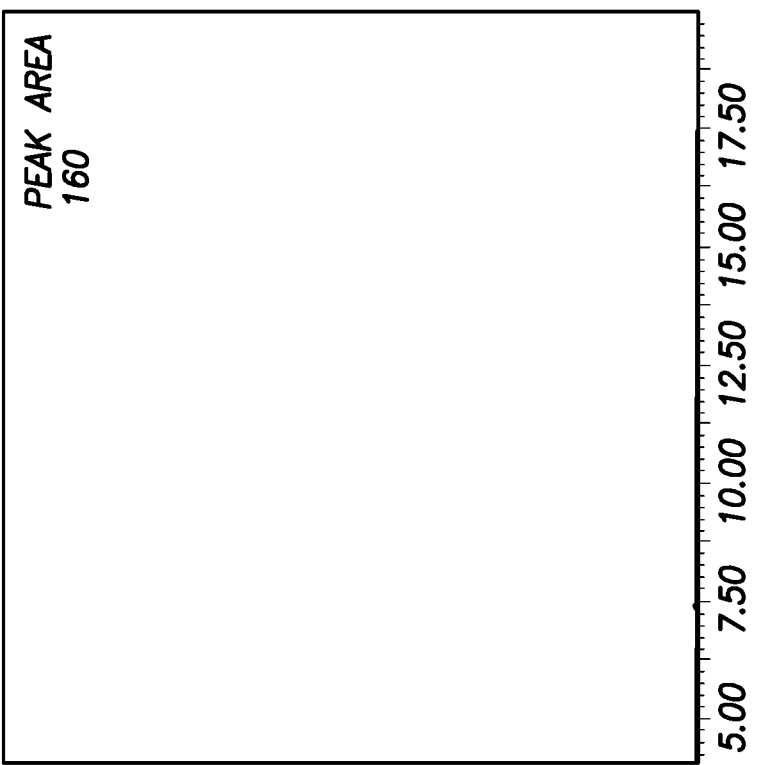
Figure 2C:
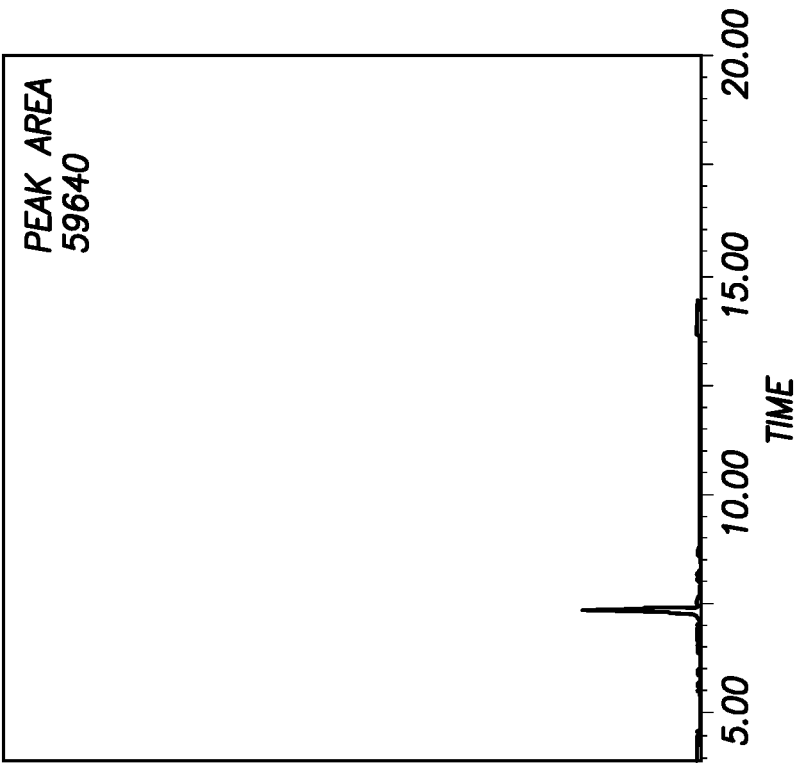
Figure 3A:
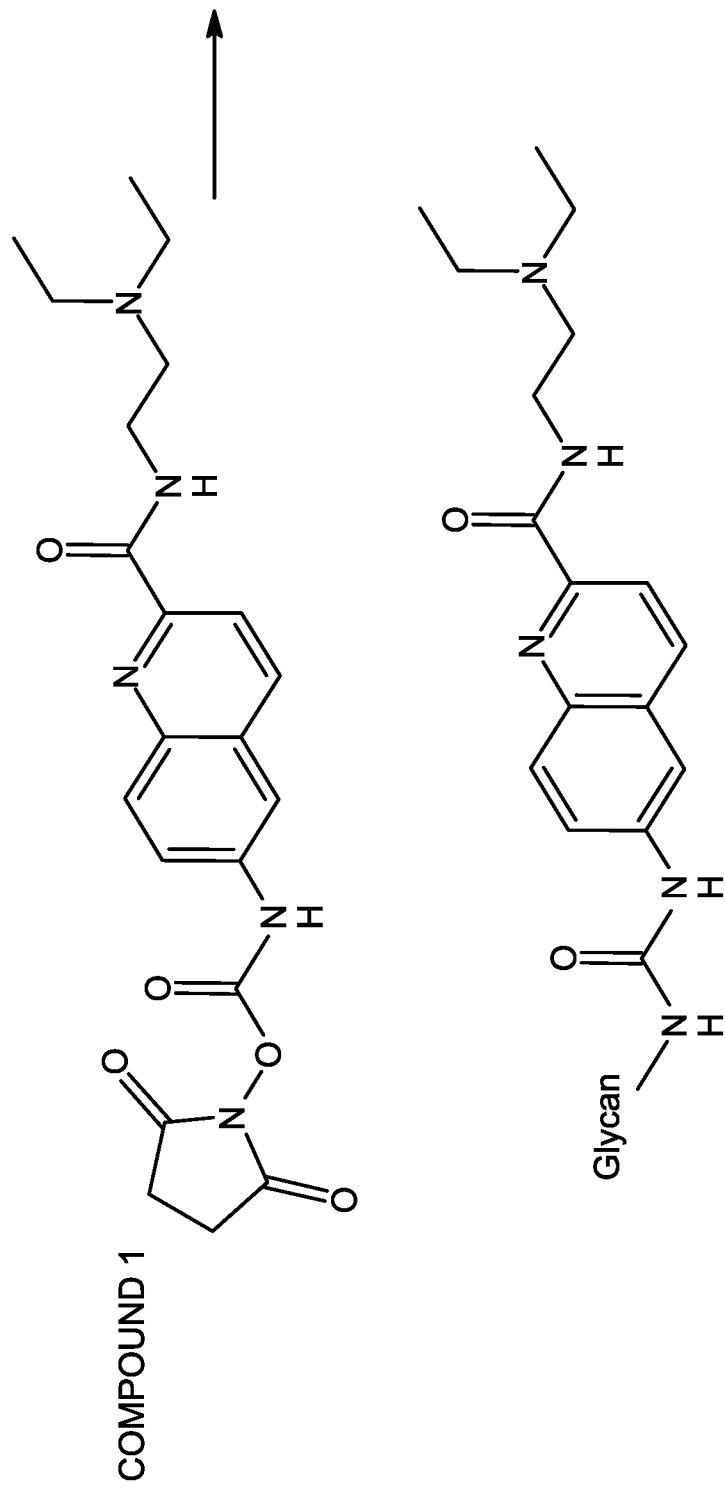
FIG. 3 depicts certain rapid tagging glycosylamine reagents and the corresponding derivatized glycan product.
Figure 3B:
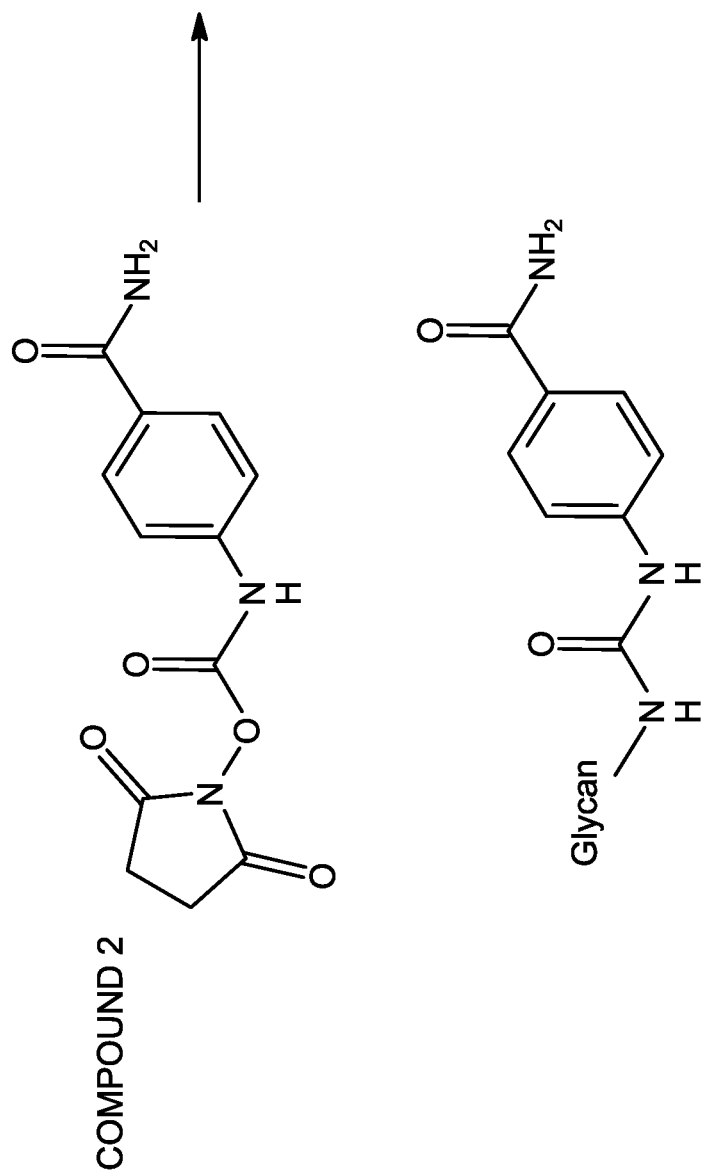
Figure 3C:
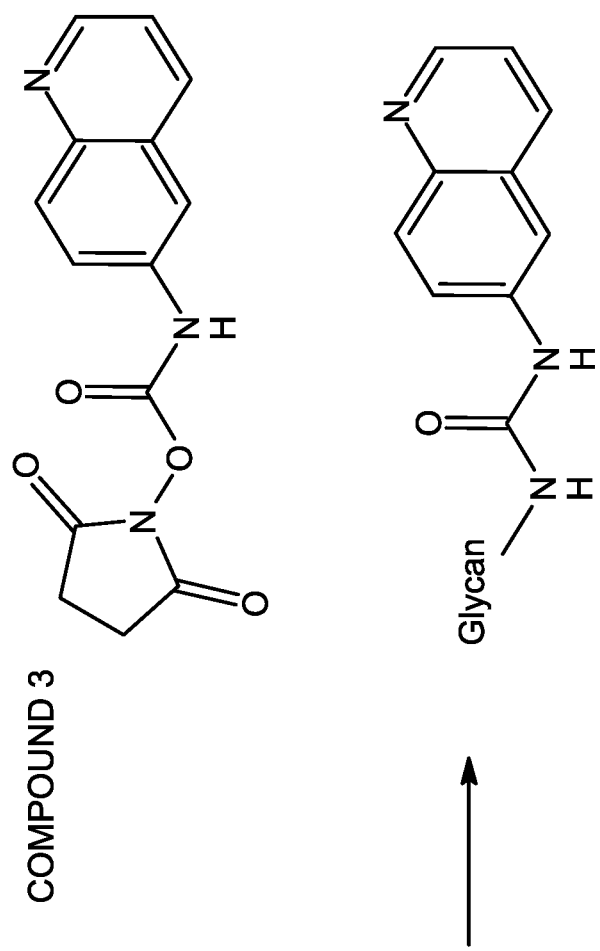
Figure 3D:
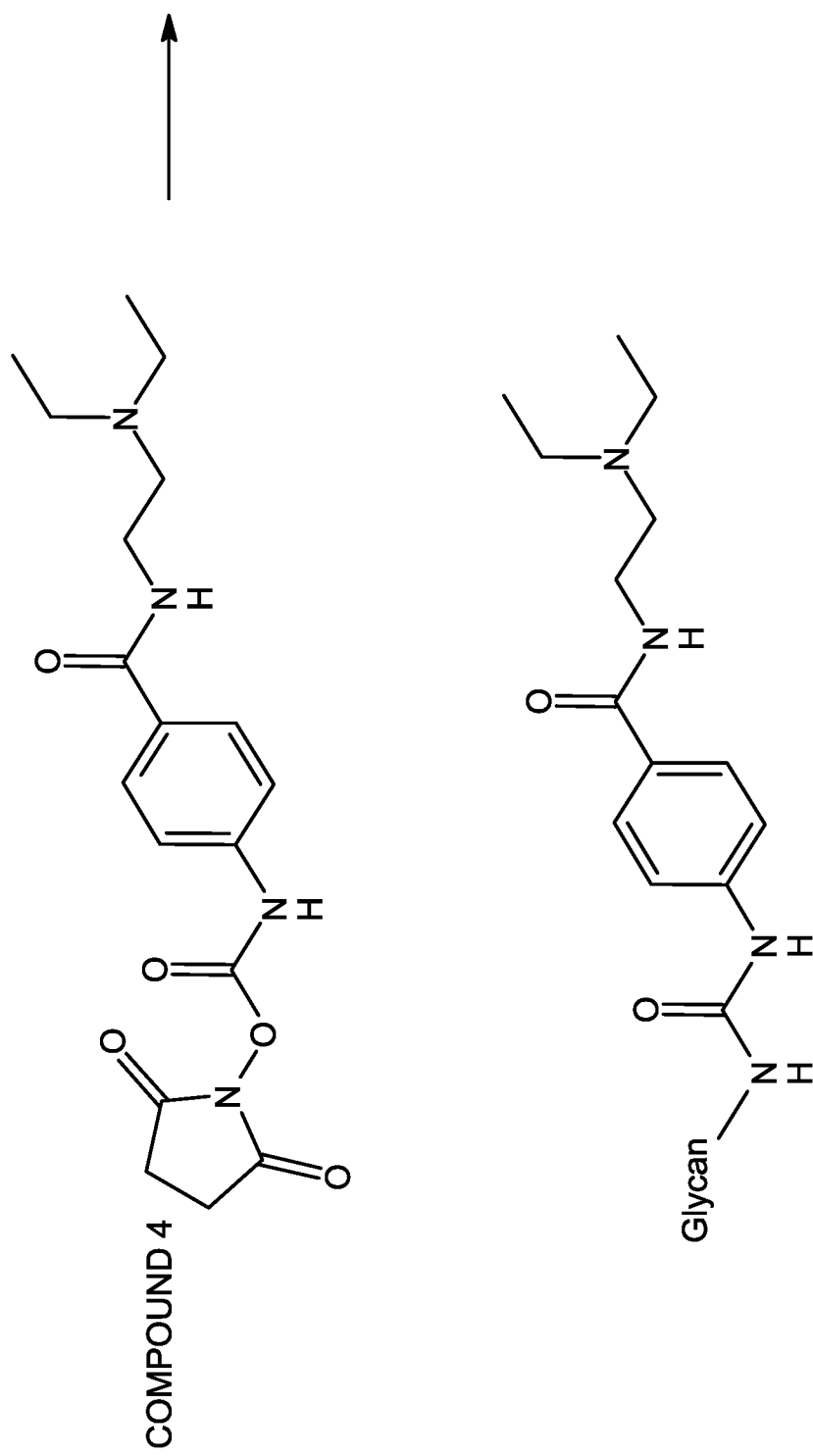
Figure 3E:
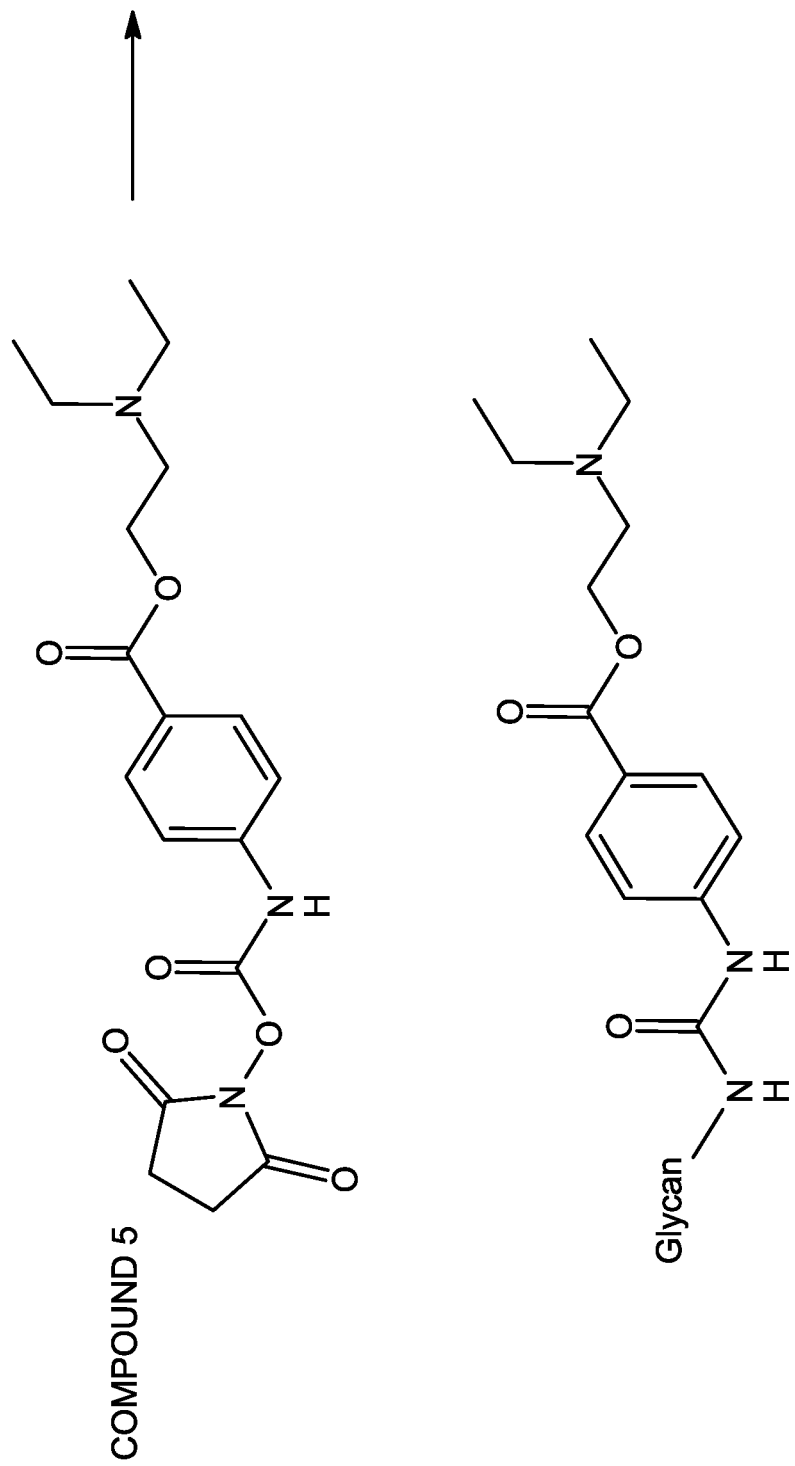
Figure 4A:
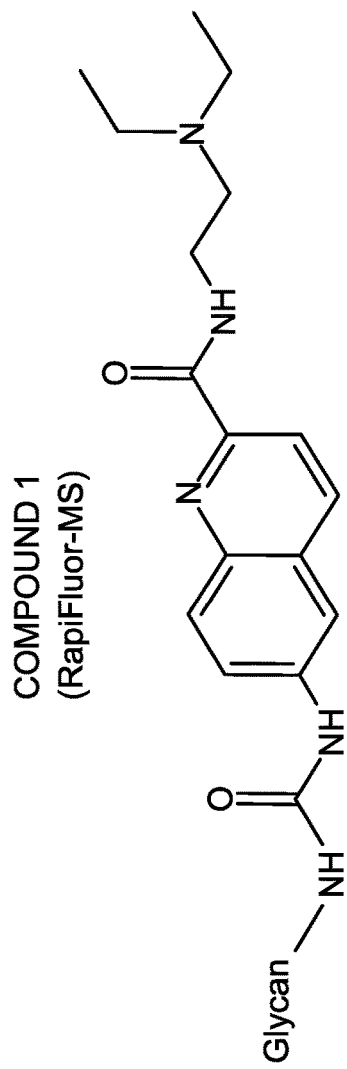
FIG. 4 shows a comparison of HILIC-MS Base Peak Intensity Chromatograms obtained for N-Glycans Labeled with Compounds 1, 2, and 3 of FIG. 3 using an Ion Mobility Capable of Mass Spectrometer (Waters Synapt G2-S, Milford, Mass.). N-glycans from 0.4 μg of anti-citrinin IgG1 monoclonal antibody were analyzed in each analysis.
Figure 4A:
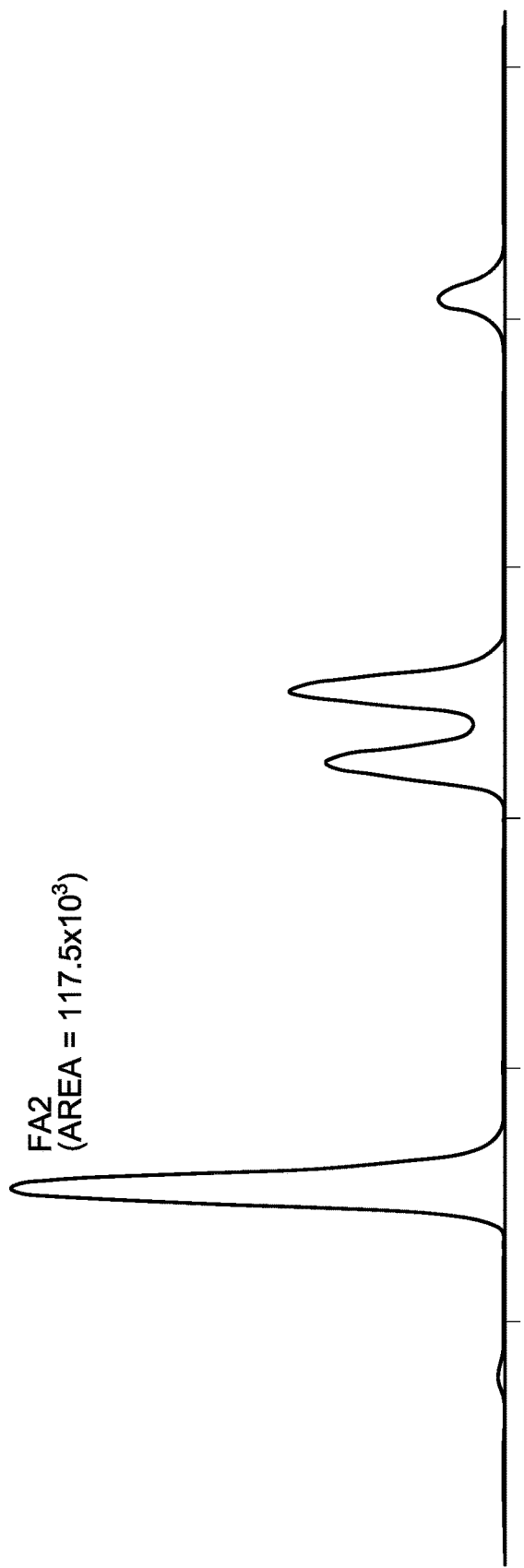
Figure 4B:
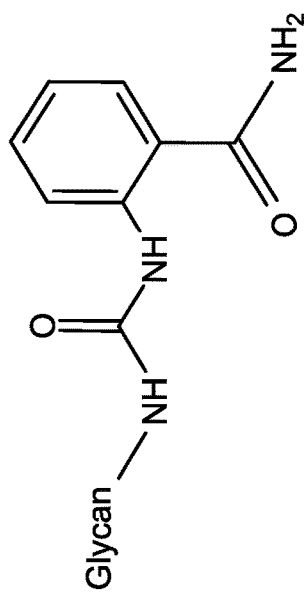
Figure 4B:
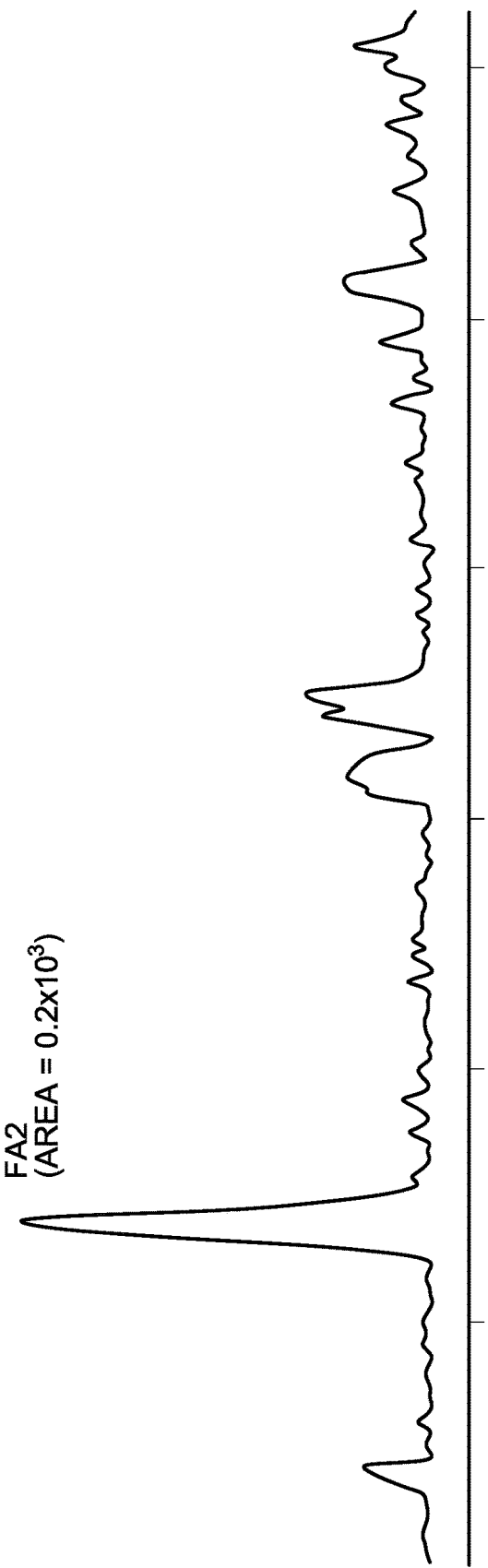
Figure 4C:
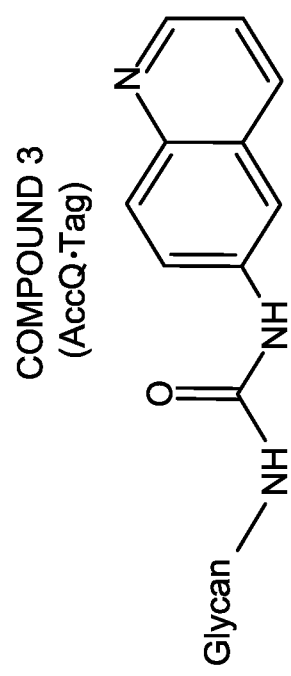
Figure 4C:
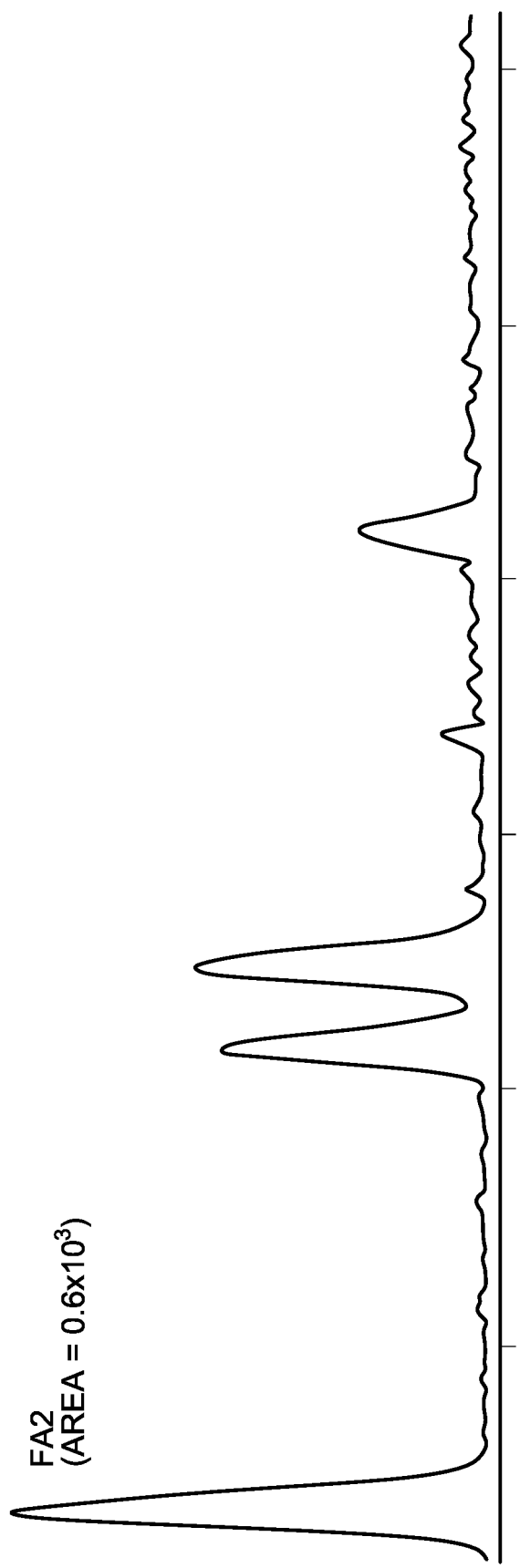

Glycans play a significant role in physiological and pathological processes. Tagging glycans (otherwise sometimes referred to herein as "labeling glycans") with MS fluorescent active compounds can improve detection via chromatographic methods including mass spectrum detection and allow for versatile analysis of glycans. Yang et. al., *Glycan Analysis by Isobaric Aldehyde Reactive Tags and Mass Spectrometry*, 85 ANAL CHEM. 8188 (2013).

Quantitative analysis of glycans from normal and disease specimens can provide insight into disease onset and progression. Relative glycan quantification can be accomplished through modification of the glycans with either chromogenic or fluorogenic tags for optical measurement or isotopic tags for mass spectrometric analysis. Yang, et al., Id. The ion abundance of N-linked glycans in electrospray ionization mass spectrometry (ESI MS) can be increased by derivatizing the glycans with neutral, hydrophobic reagents. Walker, et al., *Hydrophobic Derivatization of N-linked Glycans for Increased Ion Abundance in Electrospray Ionization Mass Spectrometry*, 22 J. AM. SOC. MASS SPECTROM. 1309 (2011).

Many peptides of biological and pharmaceutical interest are post-translationally modified and/or present at low abundance levels. Such analytes include N- and O-linked glycopeptides. Glycopeptide site microheterogeneity analysis by LC/MS is designed to characterize and quantify each glycoform of a peptide. However, glycopeptides lack appropriate chromophores on the glycan moiety and they ionize poorly by electrospray ionization ("ESI") in comparison with peptides of similar molecular weight. This deficiency leads to low signals in both MS and optical detection. Furthermore, the microheterogeneity of the glycopeptides causes the glycopeptides to be present in proteolytic digestion at very low relative abundances.

Provided herein are methods of tagging and analyzing glycans such as N-linked glycans, O-linked glycans and other aldehyde terminated saccharides. To analyze a glycan, the glycan can be labeled (also referred to herein as "tagged" or "derivatized") with one of the compounds described herein in a sample, and then subjected to liquid chromatography, mass spectrometry, and fluorescence detection. The methods provide the use of a labeling moiety for reductive amination of saccharides that is constructed to combine a high pKa (>7) basic residue with a functional group that affords a significant non-polar surface area in the labeled glycan.

In the methods presented herein, proteins, including glycoproteins, are first denatured and enzymatically digested into peptide fragments. A tagging reagent is then added to the peptide mixture. Compounds described herein can be used to label (tag) peptides, or analogous tags can be used. To derivatize the glycan, general conditions for the reductive amination reaction can be applied for tagging as described below.

Alternatively, in certain methods, rapid tagging can proceed via nucleophilic attack and substitution. In this instance, a nucleophile from a peptide attacks an NHS carbamate reactive group. The peptide is thereby derivatized via a urea linkage to be labeled with a tag containing a hydrophobic quinolone fluorescent group and tertiary amine charge tag. The moieties on a peptide that are targeted for derivatization include any residues containing primary or secondary amines. Peptides contain at least one such reside, namely an amino (N) terminus. In addition, a given peptide can contain one or more primary or secondary amines residues, most typically from containing one more lysine residues. Reactions can be optimized to minimize labeling of other potential, albeit significantly weaker, nucleophiles, including but not limited to hydroxyl and imidazole groups.

If rapid tagging reagents are utilized such as the compounds described herein, the reaction can be completed in minutes at room temperature. Yet, as described herein, molar excesses of reagent, pH, ionic strength, and buffer identity/composition can be selected. More specifically, conditions of the labeling reaction, including temperature, organic solvent composition, organic solvent concentration, buffer composition, pH, ionic strength, molar excess of reagent, and time are selected and controlled such that desired reaction selectivity between primary/secondary amines and hydroxyl groups is achieved. In turn, the yield of labeled reaction product is optimized and the generation of "overlabeled" species is minimized. In other words, the reaction product is optimized and the generation of species modified by any number of labels greater than the number of primary/secondary amines in minimized. However, sometimes overlabeling cannot be avoided.

Regardless of the type of labeling step employed, after the labeling reaction, excess labeling reagent and a significant proportion of non-glycopeptides can be removed by solid phase extraction, either in an offline or online format. As an example, to isolate and purify the labeled glycopeptides, a SepPak aminopropyl SPE sorbent in the form of a Elution plate can be conditioned with 200 µL of water. The wells can be equilibrated with 200 µL of 15:85 water/acetonitrile. Acetonitrile diluted samples can be then loaded. The well can be washed with two (2) 600 µL volumes of 1:9:90 (v/v/v) formic acid/water/acetonitrile. The labeled glycopeptides can then be eluted with three (3) 30 µL volumes of SPE Elution Buffer (200 mM ammonium acetate in 5% CAN). Alternatively, a diol bonded or hydrophilic-lipophilic balanced sorbent (containing a sufficiently hydrophilic moiety) could be used for accomplishing this step. In addition, ion pairing wash solvents can be used in the SPE cleanup of labeled glycopeptides to improve selectivity between retention of glycopeptides versus non-glycopeptides. Furthermore, solid phase extraction is an optional step. Alternatively, analyses can be directly performed on the labeling reaction mixture.

Regardless of the type of labeling step employed, tagged glycopeptides resulting from the above sample preparation are then subjected to LC/optical/MS analysis for structural characterization and glycan site microheterogeneity analysis. In these types of analyses, the labeled glycopeptides show higher optical and mass spectral signals. The gain in the enhanced signals offers higher confidence in peptide characterization and quantification. Also, MSMS fragmentation coverage is optimized in a way that benefits mass spectrometric structural investigations. A multitude of separations can be performed for the analysis, including but not limited to hydrophilic interaction chromatography (HILIC), reversed phase chromatography and mixed mode chromatography (i.e. anion exchange reversed phase). Labeled glycopeptides can be separated by HILIC using the materials and methods outlined in US Published Patent Application No. US2015/0316515, at ¶¶ [452] to [479], incorporated herein by reference. Similarly, the labeled glycopeptides can be separated using the charge surface reversed phase chromatographic materials described in US Patent Pub. No. 2013/0319086, ¶¶ [0008] to [0084], and [0347] to [0352], incorporated herein by reference. The chromatographic materials and glycan separation techniques described in U.S. Patent Application No. 62/326,783 filed Apr. 24, 2016 (unpublished) are also applicable. While the present methods are described for glycopeptide analyses, these methods can be applied generally to obtain any labeled peptides with enhanced detection properties.

As described herein, the terms "labeling" and "tagging" are used interchangeably through this specification. A "derivatized biomolecule refers to a molecule that has been labeled or tagged with the MS active, fluorescent compound.

The term "alkoxy," as used herein, alone or in combination, refers to an alkyl ether radical and the term alkyl is as defined herein. Examples of suitable alkyl ether radicals include methoxy, ethoxy, n-propoxy, iso-propoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups can be optionally substituted as defined herein without changing or affecting the fluorescent or mass spec properties of the molecule. Examples of alkyl radicals include methyl, ethyl, n-propyl, iso-propyl, n-butyl, iso-butyl, sec-butyl, tert-butyl, pentyl, iso-amyl, hexyl, octyl, nonyl and the like.

The term "alkylene," as used herein, alone or in combination, refers to a saturated aliphatic group derived from a straight or branched chain saturated hydrocarbon attached at two or more positions, such as methylene ($-CH_2-$).

The term "alkylamino," as used herein can be a mono- or dialkylated groups (also referred to "dialkylamino") such as, for example, N-methylamino, N-ethylamino, N,N-dimethylamino, N,N-ethylmethylamino and the like and combination, refers to $-NRR'$, wherein R is independently selected from the group consisting of hydrogen and alkyl, and R' is alkyl, any of which can themselves be optionally substituted and the dialkyamino group can further comprise a spacer (sometimes referred to as a linker or linker group). A molecular spacer or simply a "spacer" in chemistry is any flexible part of a molecule that provides a connection between two other parts of a molecule The term "parent molecular moiety" as used herein means and includes phenyl, quinoline, coumarin or rhodamine.

The term "amino," as used herein, alone or in combination, refers to $-NRR'$, wherein R and R' are independently selected from the group consisting of hydrogen, alkyl, acyl, heteroalkyl, aryl, cycloalkyl, heteroaryl, and heterocycloalkyl, any of which can themselves be optionally substituted.

The term "aryl," as used herein, alone or in combination, means a carbocyclic aromatic system containing one, two or three rings wherein such rings can be attached together in a pendent manner or can be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The terms "benzo" and "benz," as used herein, alone or in combination, refer to the divalent radical $C_6H_4=$derived from benzene. Examples include benzothiophene and benzimidazole.

The term "carbamate," as used herein, alone or in combination, refers to an ester of carbamic acid ($-NHCOO-$) which can be attached to the parent molecular moiety from either the nitrogen or acid end, and which can be optionally substituted as defined herein.

The term "O-carbamyl" as used herein, alone or in combination, refers to a $-OC(O)NRR'$, group-with R and R' as defined herein.

The term "N-carbamyl" as used herein, alone or in combination, refers to a ROC(O)NR'-group, with R and R' as defined herein.

The term "carbonyl," as used herein, when alone includes formyl [$-C(O)H$] and in combination is a $-C(O)-$ group.

The term "carboxy," as used herein, refers to $-C(O)OH$ or the corresponding "carboxylate" anion, such as is in a carboxylic acid salt. An "O-carboxy" group refers to a RC(O)O— group, where R is as defined herein. A "C-carboxy" group refers to a $-C(O)OR$ groups where R is as defined herein.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, can have an iodo, bromo, chloro or fluoro atom within the radical. Dihalo and polyhaloalkyl radicals can have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms can optionally be oxidized and the nitrogen heteroatom can optionally be quaternized. The heteroatom(s) O, N and S can be placed at any interior position of the heteroalkyl group. Up to two heteroatoms can be consecutive, such as, for example, —CH$_2$—NH—OCH$_3$.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom can be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the compounds are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups can be optionally substituted unless specifically prohibited.

The term "optionally substituted" means the anteceding group can be substituted or unsubstituted. When substituted, the substituents of an "optionally substituted" group can include, without limitation, one or more substituents independently selected from the following groups or a specific designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a moiety can be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which can be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups can be attached to a parent molecular moiety or can occupy a position in a chain of elements from either end as written. Thus, by way of example only, an unsymmetrical group such as —C(O)N(R)— can be attached to the parent molecular moiety at either the carbon or the nitrogen.

The term "bond" refers to a covalent linkage between two atoms, or two moieties when the atoms joined by the bond are considered to be part of larger substructure. A bond can be single, double, or triple unless otherwise specified. A dashed line between two atoms in a drawing of a molecule indicates that an additional bond can be present or absent at that position. The development and production of therapeutic proteins is becoming the fastest-growing segment of the pharmaceutical industry. The efficacy, stability and protein secretion of these large molecule drugs depend on their Post Translational Modifications ("PTMs"). Glycosylation is the most complex and common PTM and plays a vital role in the safety and efficacy of many therapeutic proteins such as recombinant antibodies. Several studies have shown the correlation between glycosylation variations caused by cell line selection and changes in culture medium parameters. Patrick Hossler et al., *Optimal and Consistent Protein Glycosylation in Mammalian Cell Culture*, 19 GLYCOBIOLOGY 926 (2009). These variations can have a profound effect on the biological activities of the mAb drugs, which leads to changes in drug potency in the final product. Regulatory agencies require monitoring of batch-to-batch recombinant antibody drug production quality and mandate detailed assessment of the protein glycosylation microheterogeneity and consistency.

The compounds described herein can also form hydrogen bonds with other compounds. A hydrogen bond is an electromagnetic attractive interaction between polar molecules, where hydrogen is bonded to an electronegative atom such as nitrogen or oxygen. The hydrogen bond represents a strong dipole-dipole attraction. These hydrogen-bond attractions can occur between molecules (intermolecular) or within different parts of a single molecule (intramolecular). When a hydrogen atom is attached to an electronegative atom, it is considered a hydrogen bond donor. The electronegative atom is considered a hydrogen bond acceptor, whether it is bonded to a hydrogen atom or not.

Asymmetric centers exist in the compounds presented herein. These centers are designated by the symbols "R" or "S," depending on the configuration of substituents around the chiral carbon atom. It should be understood that the compounds encompass all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of certain stereochemistry are either commercially available or can be made and resolved by techniques known in the art. Additionally, the compounds described can exist as geometric isomers and includes all cis, trans, syn, anti, entgegen (E), and zusammen (Z) isomers as well as the appropriate mixtures thereof. Additionally, compounds can exist as tautomers. All tautomeric isomers are provided. Additionally, the present compounds can exist in unsolvated as well as solvated forms with pharmaceutically acceptable solvents such as water, ethanol, and the like. In general, the solvated forms are considered equivalent to the unsolvated forms.

Hence, the compounds described herein can also be in the form of a salt or solvate, or acid addition salts. Through a reaction with either organic or inorganic acids, compounds presented herein or groups of compounds can form a salt. For example, in acid-base neutralization, an acid and a base react to form water and a salt. Basically, to react together, there must be the transfer of protons between acids and bases. Also, different acids can produce different ions. For example, an Arrhenius acid produces hydronium ions when it dissociates in water. Similarly, a Bronsted-Lowry acid is a proton donor that donates hydrogen ions to the base. Hence, proton acceptors and proton donors are the basis for the reaction and are referred to sometimes as a conjugate base or a conjugate acid. A conjugate pair refers to acids and bases with common features, where there is an equal loss/gain of protons between the pairs. For example, $NH_4^+$ is the conjugate acid to the base $NH_3$ because $NH_3$ gains a hydrogen ion to form $NH_4^+$ as $H_2O$ donates a hydrogen ion to form $OH^-$, the conjugate base. On the other hand, under a different theory, a Lewis acid accepts an electron pair and a Lewis base donates an electron pair donor. Accordingly, the proton $H^+$ can be an electron pair acceptor. Moreover, a compound can be both, a Lewis acid and a Lewis base, depending on the reaction. For example, methyl iodide can behave as both, a Lewis acid and a Lewis base, where the methyl group is donated to form a salt.

The compounds of the formulas described herein can have quaternary nitrogens. The quaternary nitrogens will have a positive charge on the nitrogen and can be associated with a counterion and include all quaternary amine-counterion complexes of compounds when a compound includes a quaternary amine group.

Examples of acids which can be employed to form a salt of any of the compounds provided herein include inorganic acids and organic acids as well known to those skilled in the art such as, but not limited to, N-hydroxysuccinimide, hydrochloric, hydrofluoric, hydroiodic, hydrobromic, sulfuric, hydrosulfuric, thiosulfuric, hydrocyanic, phosphoric, phosphorous, hydrochlorous, chlorous, nitrous, nitric, chloric, perchloric, sulfurous, oxalic, maleic, succinic, and citric. Salts can also be formed by coordination of the compounds with an alkali metal or alkaline earth ion. In addition, other acids can form a salt including, but not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+),camphor-10-sulfonic a cid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, isobutyric acid, lactic acid (DL), lactobionic acid, lauric acid, maleic acid, malic acid (–L), malonic acid, mandelic acid (DL), methanesulfonic acid, naphthalene-1,5, disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, tartaric acid (+L), thiocyanic acid, toluenesulfonic acid (p), undecylenic acid.

For the compounds described herein, the counterion can be the conjugate base formed after reacting a compound or groups of compounds with an acid. In other words, counterion holds the opposite charge to that of the compound or compounds it is associated with. Thus, with respect to possible salts of the compounds herein having a conjugate acid of $NH_4^+$, the counterion represents the anionic part of the salt. In addition, it can be possible to have four organic substituents on the nitrogen. These species are not amines but are quaternary ammonium cations having a charged nitrogen center. Quaternary ammonium salts can exist with many kinds of anions.

Hence, counterions of a salt compound described herein can include, but are not limited to, any of the following common anions and oxoanions: N-hydroxysuccinimidyl, hydride ($H^-$), fluoride ($F^-$), chloride ($Cl^-$), bromide ($Br^-$), iodide ($I^-$), oxide ($O^{2-}$), hydroxide ($OH^-$), peroxide ($O_2^{2-}$), sulfide ($S^{2-}$), hydrogen sulfide ($HS^-$), selenide ($Se^{2-}$), nitride ($N^{3-}$), azide ($N_3^-$), phosphide ($P^{3-}$), arsinide ($As^{3-}$), carbide ($C^{4-}$), cyanide ($CN^-$), hypochlorite ($ClO_1^-$), chlorite ($ClO_2^-$), chlorate ($ClO_3^-$), perchlorate ($ClO_4^-$), sulfite ($SO_3^{2-}$), sulfate ($SO_4^{2-}$), hydrogen sulfate ($HSO_4^-$), thiosulfate ($S_2O_3^{2-}$), nitrite ($NO_2^-$), nitrate ($NO_3^-$), phosphite ($PO_3^{2-}$), phosphate ($PO_4^{3-}$), (mono)hydrogen phosphate ($HPO_4^{2-}$), dihydrogen phosphate ($H2PO_4^-$), carbonate ($CO_3^{2-}$), hydrogen carbonate ($HCO_3^-$), oxalate ($C_2O_4^{2-}$), cyanate ($NCO^-$), isocyanate ($OCN^-$), thiocyanate ($SCN^-$), chromate ($CrO_4^{2-}$), dichromate ($Cr_2O_7^{2-}$), permanganate ($MnO_4^-$).

Reductive Amination

Methods for tagging glycans including N-linked glycans and O-linked glycans, with MS active fluorescent compounds of Formula I, as well as conjugates resulting therefrom are provided. In an embodiment, the glycan is tagged, derivatized or conjugated through an aldehyde or ketone with the amine of a compound provided herein via reductive amination.

New compounds (also referred herein to as "reagents" and/or "molecules") specific for N-linked and O-linked glycans amino acids and peptides, are provided for enhanced MS detection and fluorescence tagging of glycans and other biomolecules with enhanced MS signals. Using these reagents, the reaction times necessary to carry out the tagging process (or otherwise sometimes referred to herein as "labeling") can be performed efficiently and applied to a wider group of biopolymers. The described compounds are useful in a wide variety of processes that rely on glycan and amino acid/peptide analysis for essential information of a product, process, or protein. As such, the molecules described herein can be used in processes such as protein characterization, cell culture monitoring, synthetic peptide manufacturing, and food analysis.

More specifically, N-linked glycans are attached to asparagines via an N-acetylglucosamine ("GlcNAc") residue in an Asn-Xxx-(Ser, Thr) motif where Xxx can be any amino acid except proline. O-linked glycans are attached to either Serine or Threonine. N-linked glycans can be removed from the glycoprotein chemically or enzymatically. Examples of N-linked glycans include, but are not limited to, mannobiose (Man2), mannotriose (Man3), mannotetraose (Man4), mannopentaose (Man5), mannohexaose (Man6) and mannoheptaose (Man7). Other glycans include A2, FA2, M5, FA1G1, A2G1, FA2G1, FA2G2, FA2G1Ga1, FA2G2Ga1, FA2G2Sg1, FA2G1Ga2, FA2G2GaSg1

To derivatize the glycan, general conditions for the reductive amination reaction can be applied for tagging as described below. For example, the reaction can be conducted in the presence of reducing agents such as sodium cyanoborohydride, sodium triacetoxyborohydride, picoline borane. In an embodiment, the reductive amination is conducted in aqueous media. In an embodiment, the reductive amination reaction of aldehyde containing compounds can be conducted in non-aqueous solvents. Reagents that can facilitate reductive amination include $LiAlH_4$, $ZnCl_2$—$Zn(BH_4)_2$; $NiCl_2$—$NaBH_4$; $Ti(iPrO)_4$-polymethylhydrosiloxane; $Ti(i-PrO)_4$—$NaBH_4$; $Bu_3SnH$; $Bu_2SnClH$ and $Bu_2SnIH$; decaborane; silica gel-$Zn(BH_4)_2$; $Et_3SiH$-trifluoroacetic acid; pyridine-$BH_3$; phenylsilane-dibutyltin dichloride. Basu et. al., 4 SYNLETT 555 (2003). The reaction can be conducted in a mixture of citric acid and/or acetic acid with an organic solvent such as dimethylsulfoxide dimethylformamide, formamide, hexamethylphosphoramide, hexamethylphosphorus triamide, 1,3-dimethyl-3,4,5,6-tetrahydro-2(1H)-pyrimidinone or dimethylacetamide. The reaction can also be conducted in a solvent selected from tetrahydrofuran, dichloromethane, 1,2-dichloroethane, ethanol, methanol or isopropanol, toluene and xylene, and mixtures thereof.

The following schematic shows the tagging of a glycan using a compound of Formula I through reductive amination:

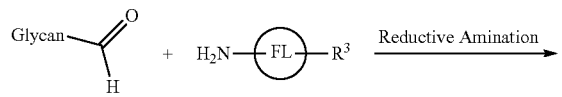

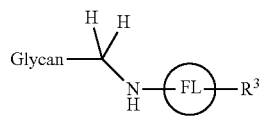

where FL and $R^3$ are as described above.

Quinoline Based MS Active Fluorescence Tagging Compounds

Methods for tagging and analyzing glycans can be accomplished by fluorescence and mass spectroscopy following reductive amination of glycans with MS active, fluorescence tagging quinoline derivatives of the structural Formula II:

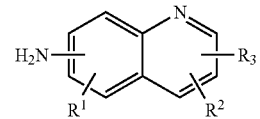

Formula II wherein each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

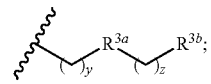

$R^{3a}$ is selected from ester, amide, amine, oxygen, urea, carbamate, carbonate, sulfur, thiourea, thiocarbamate, alkyl or carbonyl;

$R^{3b}$ is

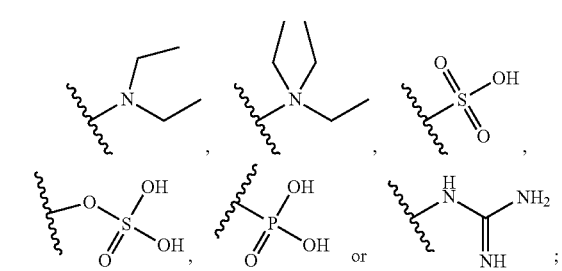

y=0-12;

z=1-12;

and salts or solvates thereof.

In an embodiment, methods include tagging glycans and other biomolecules with compounds of Formula IIA:

Formula IIA

[Structure: H₂N-substituted isoquinoline with R¹, R² substituents and C(O)NH-(CH₂)z-R³ᵇ group]

wherein
each of R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

[Structures: diethylamino, diethylamino variant, sulfonate; phosphate, phosphonate, guanidino groups]

$z=1-12$;
and salts or solvates thereof.

In an embodiment, methods for tagging glycans and other biomolecules with compounds of Formula IIB are provided:

Formula IIB

[Structure: H₂N-substituted isoquinoline with NH-C(O)-(CH₂)z-R³ᵇ group]

wherein
each of R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

[Structures: diethylamino, diethylamino variant, sulfonate; phosphate, phosphonate, guanidino groups]

$z=1-12$; and salts or solvates thereof.

In an embodiment, methods for tagging glycans and other biomolecules with compounds of Formula IIC are provided:

Formula IIC

[Structure: H₂N-substituted isoquinoline with NH-(CH₂)z-R³ᵇ group]

wherein
each R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

[Structures: diethylamino, diethylamino variant, sulfonate; phosphate, phosphonate, guanidino groups]

$z=1-12$;
and salts or solvates thereof.

In an embodiment, methods for tagging glycans and other biomolecules with compounds of Formula IID are provided:

Formula IID

[Structure: H₂N-substituted isoquinoline with O-(CH₂)z-R³ᵇ group]

wherein
each R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

[Structures: diethylamino, diethylamino variant, sulfonate; phosphate, phosphonate, guanidino groups]

$z=1-12$;
and salts or solvates thereof.

In an embodiment, methods for tagging glycans and other biomolecules with compounds of Formula IIE are provided:

Formula IIE

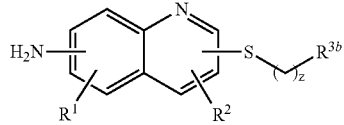

wherein
each $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

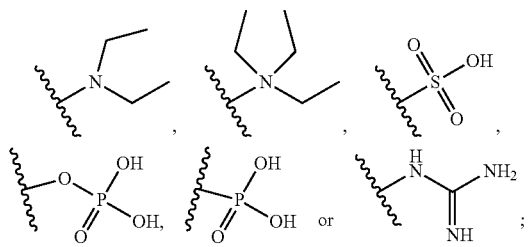

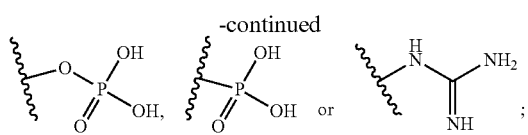

z=1-12;
and salts or solvates thereof.

In an embodiment, methods for tagging glycans and other biomolecules with compounds of Formula IIG are provided:

Formula IIG

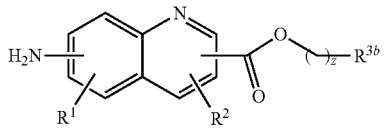

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

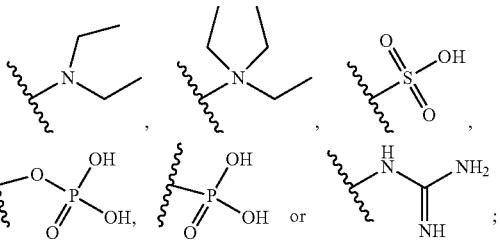

z=1-12;
and salts or solvates thereof.

In an embodiment, methods for tagging glycans and other biomolecules with compounds of Formula IIF are provided:

Formula IIF

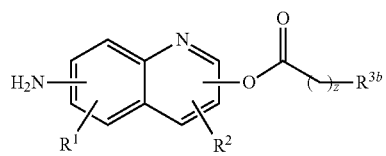

wherein
each $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

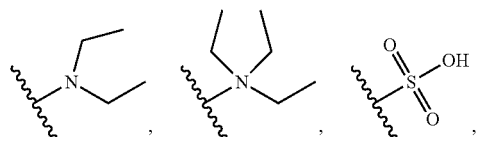

Provided herein are methods for tagging glycan wherein compounds are of Formula II, IIA, IIB, IIC, IID, IIE, IIF or IIG wherein $R^1$ is hydrogen. In an embodiment, further provided are methods wherein compounds are of Formula II, IIA, IIB, IIC, IID, IIE, IIF or IIG wherein $R^2$ is hydrogen. Methods are provided wherein compounds are of Formula II, IIA, IIB, IIC, IID, IIE, IIF or IIG wherein $R^1$ and $R^2$ are hydrogen.

In addition, provided below are exemplary compounds (Table A) of the structural Formulas II, IIA, IIB, IIC, IID, IIE, IIF or IIG which can be used in the methods described herein for fluorescent labeling of glycans and for subsequent analysis by means of liquid chromatography and mass spectrometry. The compounds of structural Formulas II, IIA, IIB, IIC, IID, IIE, IIF or IIG could be optionally substituted with any group that does not substantially reduce the fluorescence of the compound.

TABLE A

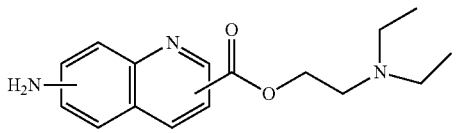

TABLE A-continued
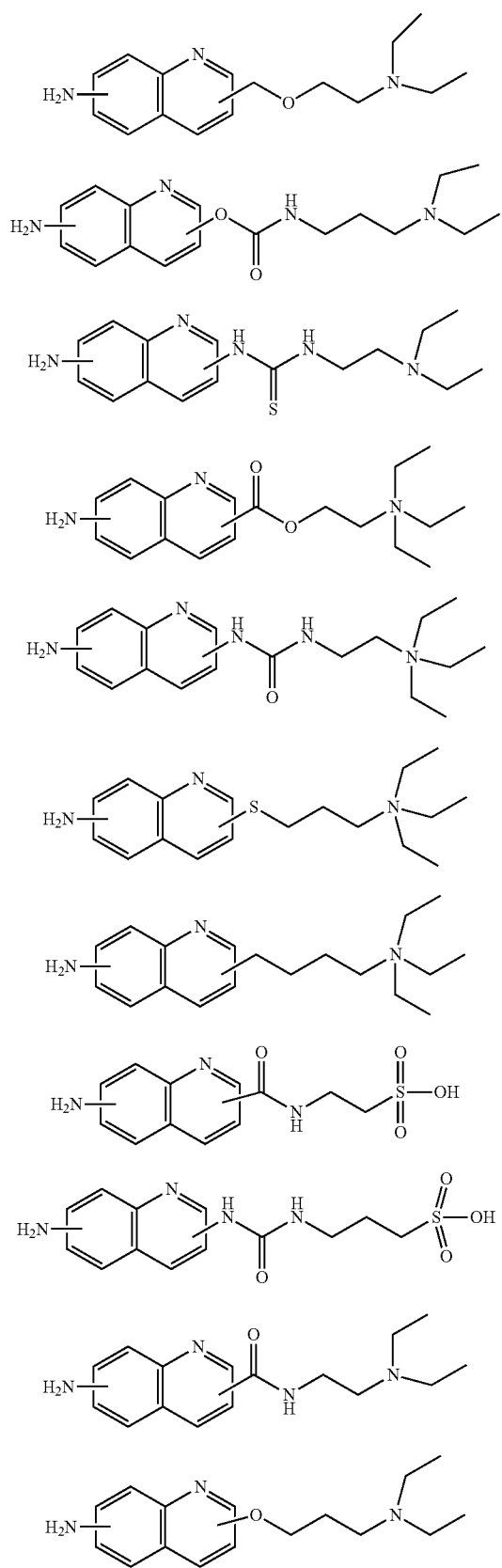
TABLE A-continued
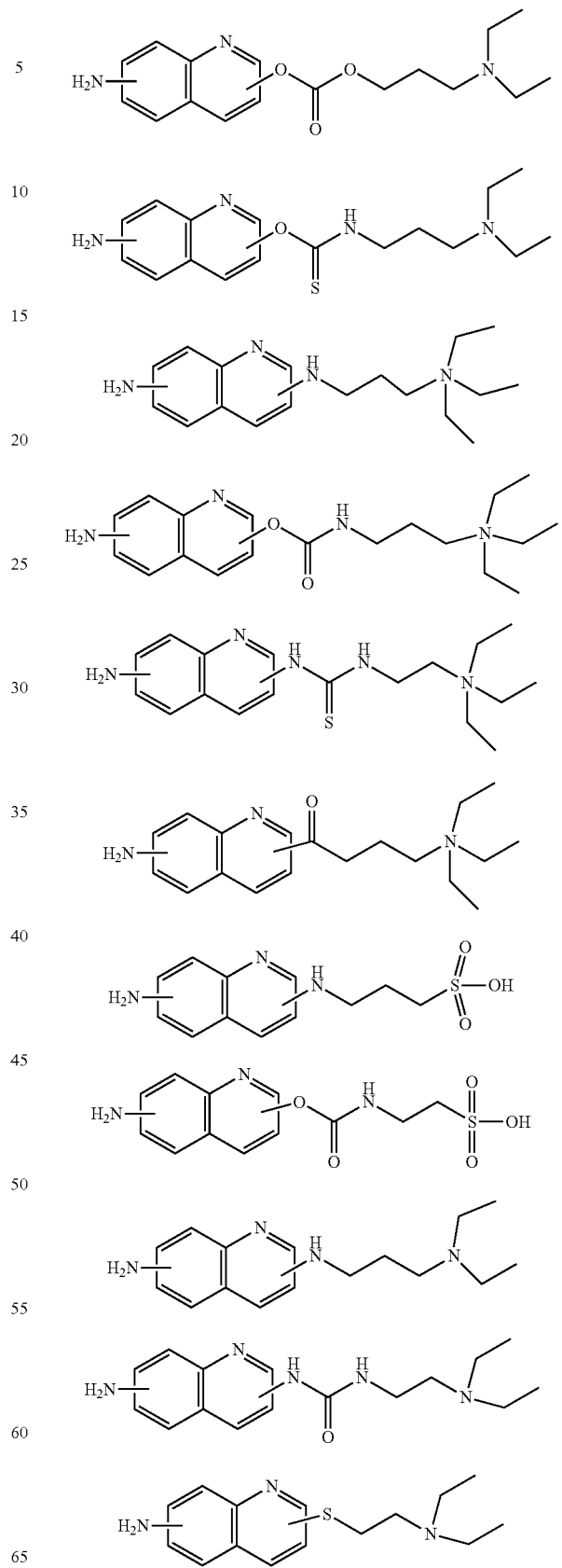

TABLE A-continued
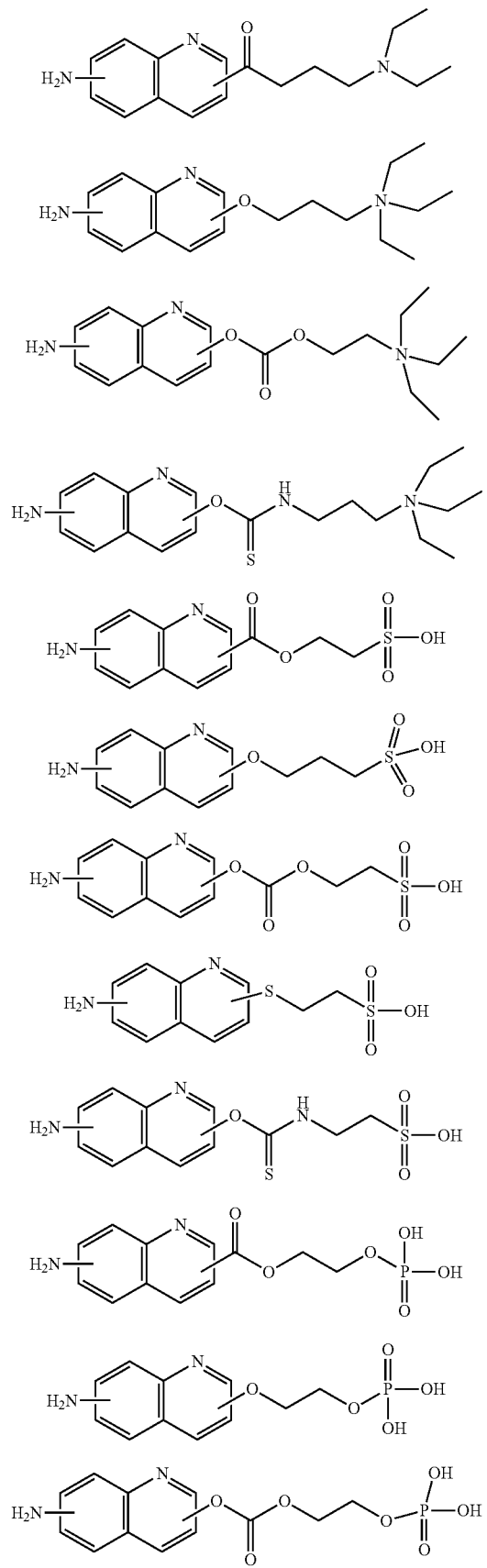
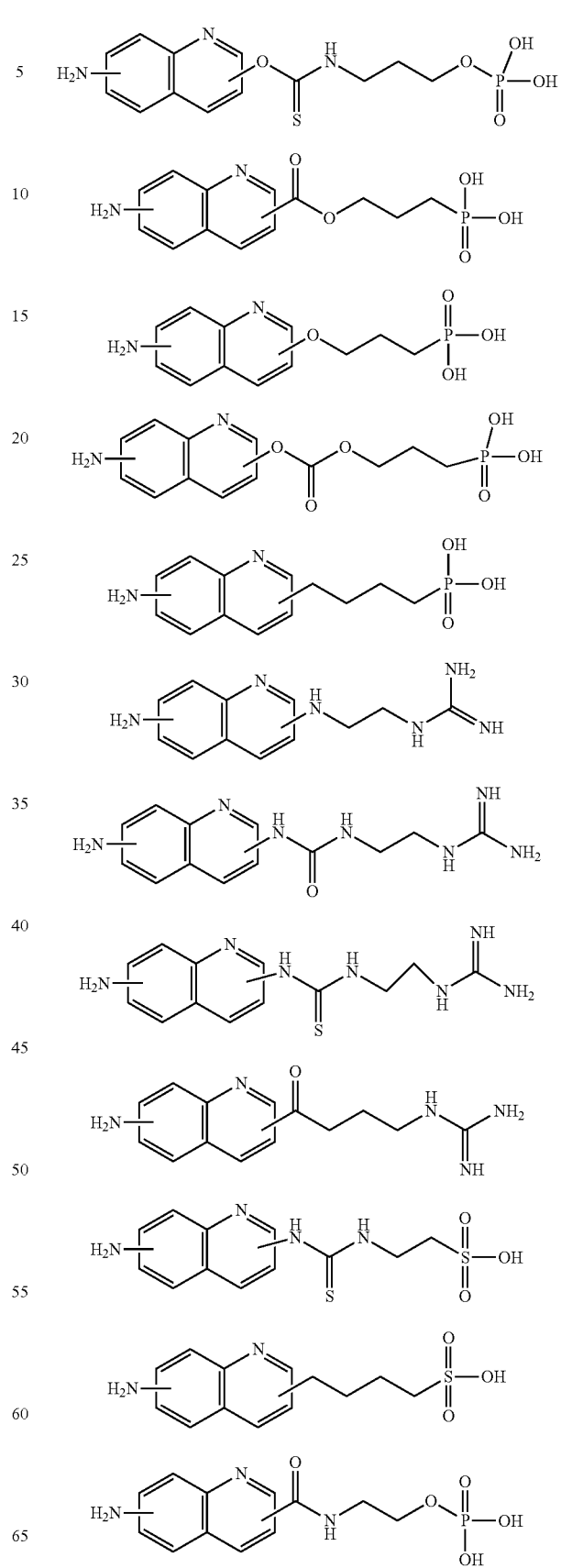

TABLE A-continued

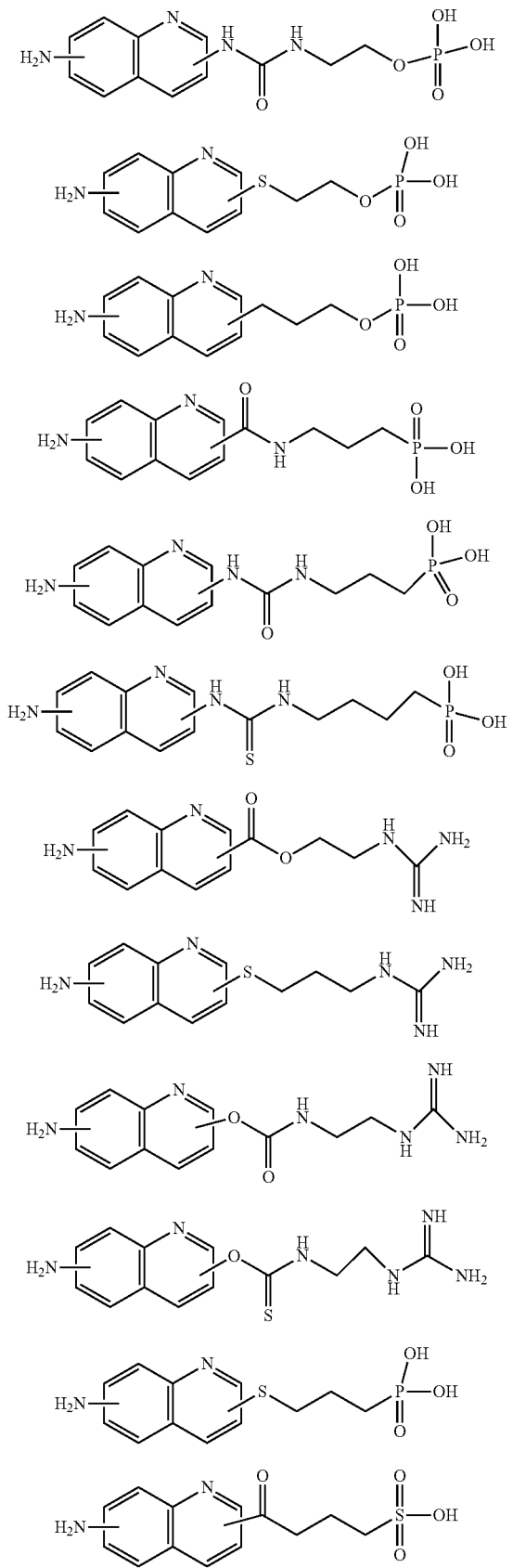

TABLE A-continued

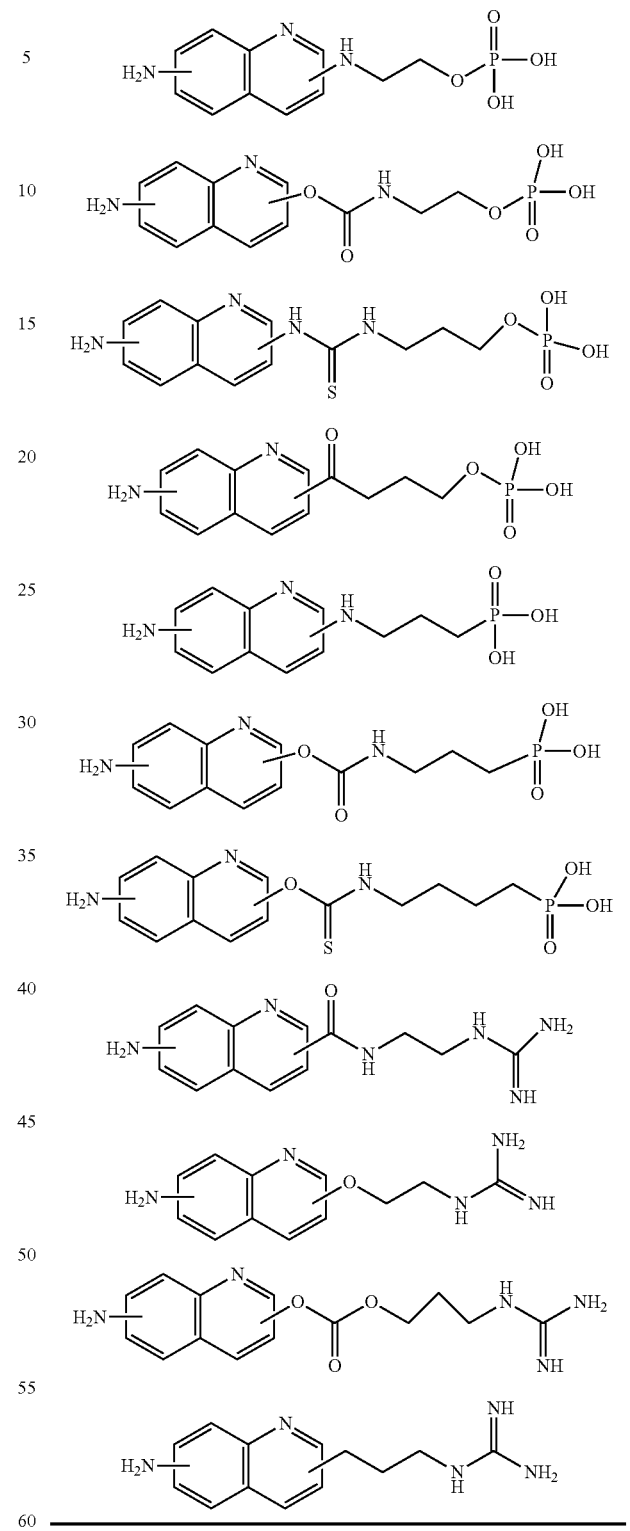

Methods for tagging, derivatizing or conjugating glycans containing at least one ketone group or an aldehyde group with a compound of Formula II, IIA, JIB, IIC, IID, IIE, IIF or IIG, or a compound of Table A by reductive amination reaction are further provided. This reaction between any one or more of the compounds and the glycan can be conducted under conditions that facilitate reductive amination in the presence of a reducing agent, such as from sodium cyanoborohydride or sodium triacetoxyborohydride. The reaction can be carried out in a solution or suspension of a compound of Formula II, IIA, IIB, IIC, IID, IIE, IIF or IIG, or a compound of Table A in an acidic media, for example in citric acid or acetic acid, and by mixing with a solution or suspension of a reducing agent such as cyanoborohydride or sodium triacetoxyborohydride in an organic solvent, for example, tetrahydrofuran or dimethylsulfoxide.

Methods for analyzing a glycan and other biomolecules containing an aldehyde group in a sample by means of liquid chromatography and mass spectrometry are provided. These methods comprise the step of labeling the glycan in a sample by reacting with one or more of the compounds of Formula II, IIA, IIB, IIC, IID, IIE, IIF or IIG, or compound of Table A for a time and under conditions suitable to facilitate the labeling through reductive amination; and subjecting the labeled conjugate to liquid chromatography and mass spectrometry.

Glycans and other biomolecules can be conjugated to MS active fluorescent compounds of Formula II and salts or solvates thereof. The following schematic shows the tagging of a glycan using a compound of Formula II through reductive amination:

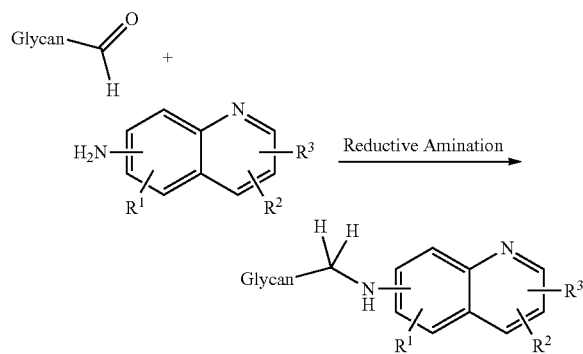

wherein FL $R^1$, $R^2$ and $R^3$ are as described herein.

Coumarin Based MS Active Fluorescence Tagging Compounds

Methods for tagging and analyzing glycans can be accomplished by fluorescence and mass spectroscopy following reductive amination of glycans with compounds of the structural Formula III:

Formula III

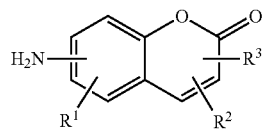

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

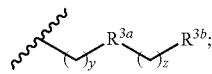

$R^{3a}$ is selected from ester, amide, amine, oxygen, urea, carbamate, carbonate, sulfur, thiourea, thiocarbamate, alkyl or carbonyl;
$R^{3b}$ is

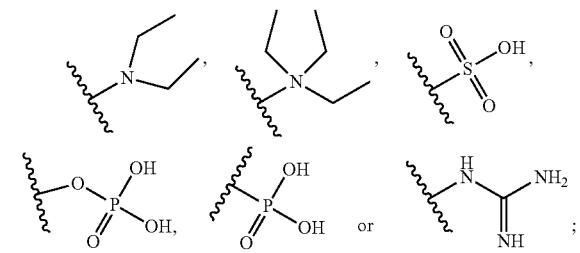

y=0-12;
z=1-12;
and salts or solvates thereof.

In an embodiment, methods for tagging glycans with compounds of Formula IIIA are provided:

Formula IIIA

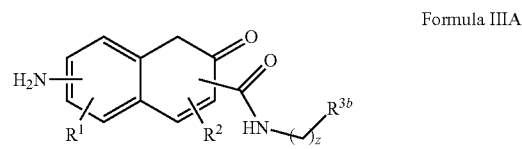

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

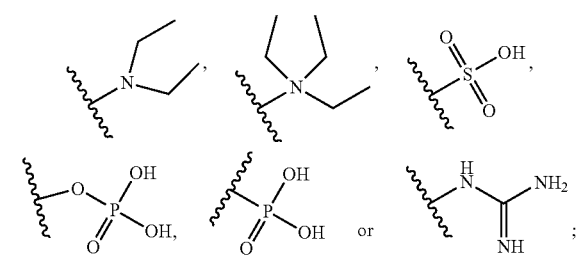

z=1-12;
and salts or solvates thereof.

In an embodiment, methods for tagging glycans and other biomolecules with compounds of Formula IIIB are provided:

Formula IIIB

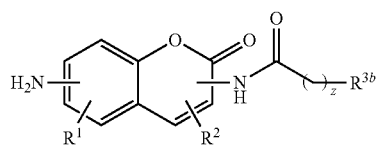

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

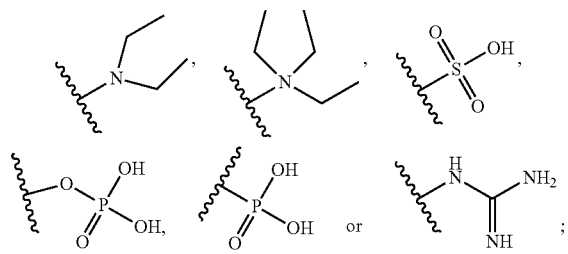

z=1-12;
and salts or solvates thereof.

In an embodiment, methods for tagging glycans and other biomolecules with compounds of Formula IIIC are provided:

Formula IIIC

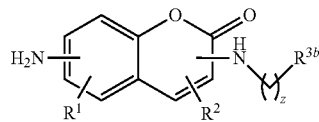

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

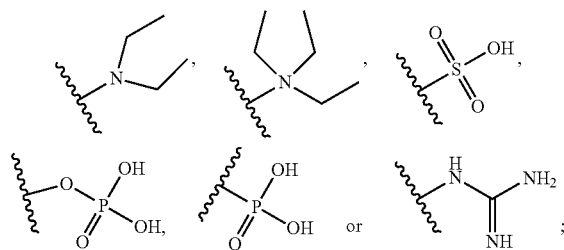

z=1-12;
and salts or solvates thereof.

In an embodiment, methods for tagging glycans with compounds of Formula IIID are provided:

Formula IIID

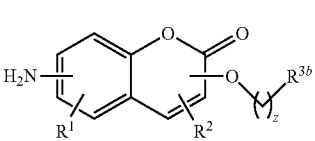

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

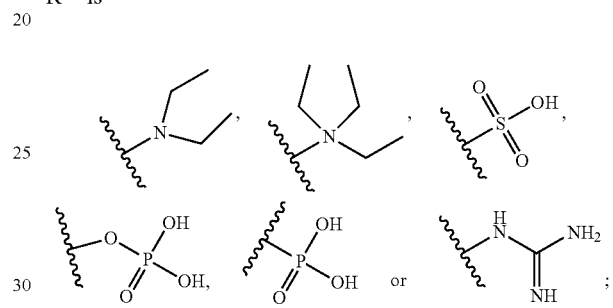

z=1-12;
and salts or solvates thereof.

In an embodiment, methods are provided for tagging glycans with compounds of Formula IIIE:

Formula IIIE

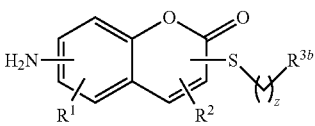

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

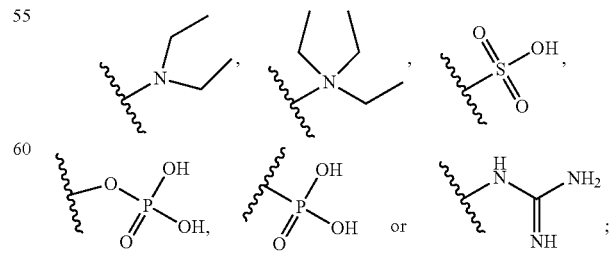

z=1-12;
and salts or solvates thereof.

In an embodiment, methods for tagging glycans with compounds of Formula IIIF are provided:

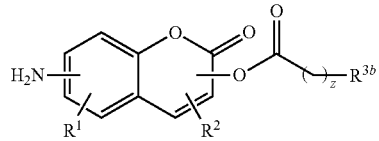

Formula IIIF wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

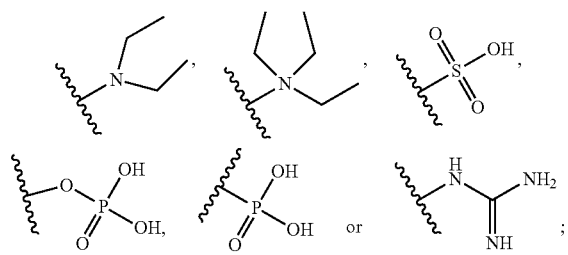

$z=1-12$;
and salts or solvates thereof.

In an embodiment, methods for tagging glycans with compounds of Formula IIIG are provided:

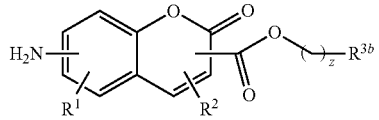

Formula IIIG wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

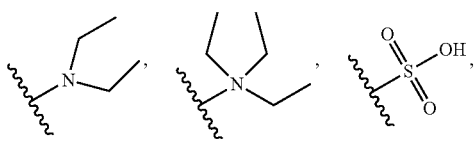

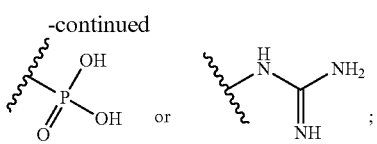

$z=1-12$;
and salts or solvates thereof.

In an embodiment, provided are compounds of Formula III, IIIA, IIIB, IIIC, IIID, IIIE, IIIF or IIIG wherein $R^1$ is hydrogen. In an embodiment, the compounds of Formula III, IIIA, IIIB, IIIC, IIID, IIIE, IIIF or IIIG include compounds wherein $R^2$ is hydrogen. In an embodiment, the compounds of Formula III, IIIA, IIIB, IIIC, IIID, IIIE, IIIF or IIIG include compounds wherein $R^1$ and $R^2$ are hydrogen.

In addition, provided below are exemplary compounds (Table B) of the structural Formulas III, IIIA, IIB, IIIC, IIID, IIIE, IIIF or IIIG which can be useful for labeling glycans and subsequent analysis by means of liquid chromatography and mass spectrometry. The compounds of structural Formulas III, IIIA, IIIB, IIIC, IIID, IIIE, IIIF or IIIG could be optionally substituted with any group that does not substantially reduce the fluorescence of the compound.

TABLE B

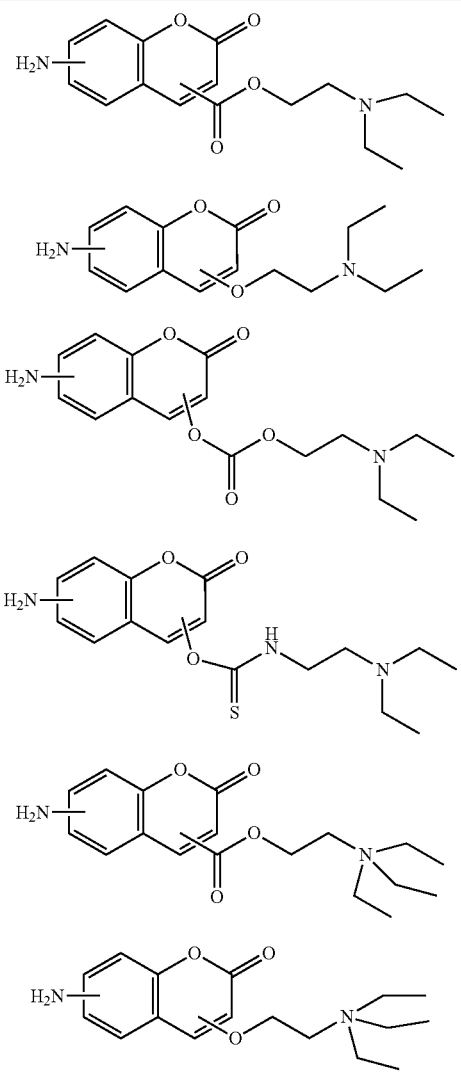

TABLE B-continued
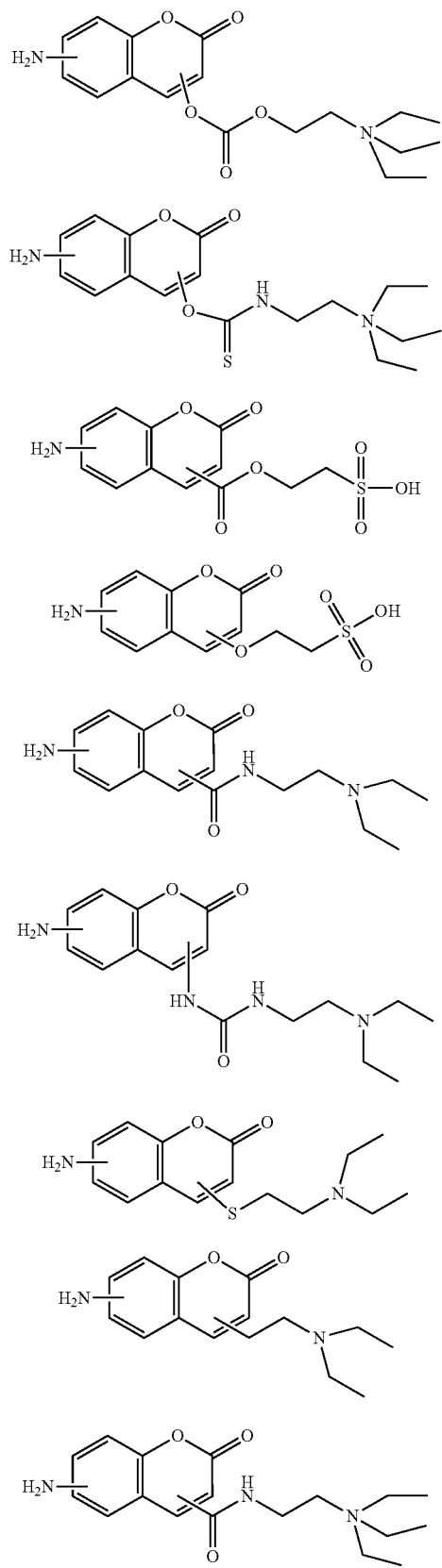
TABLE B-continued
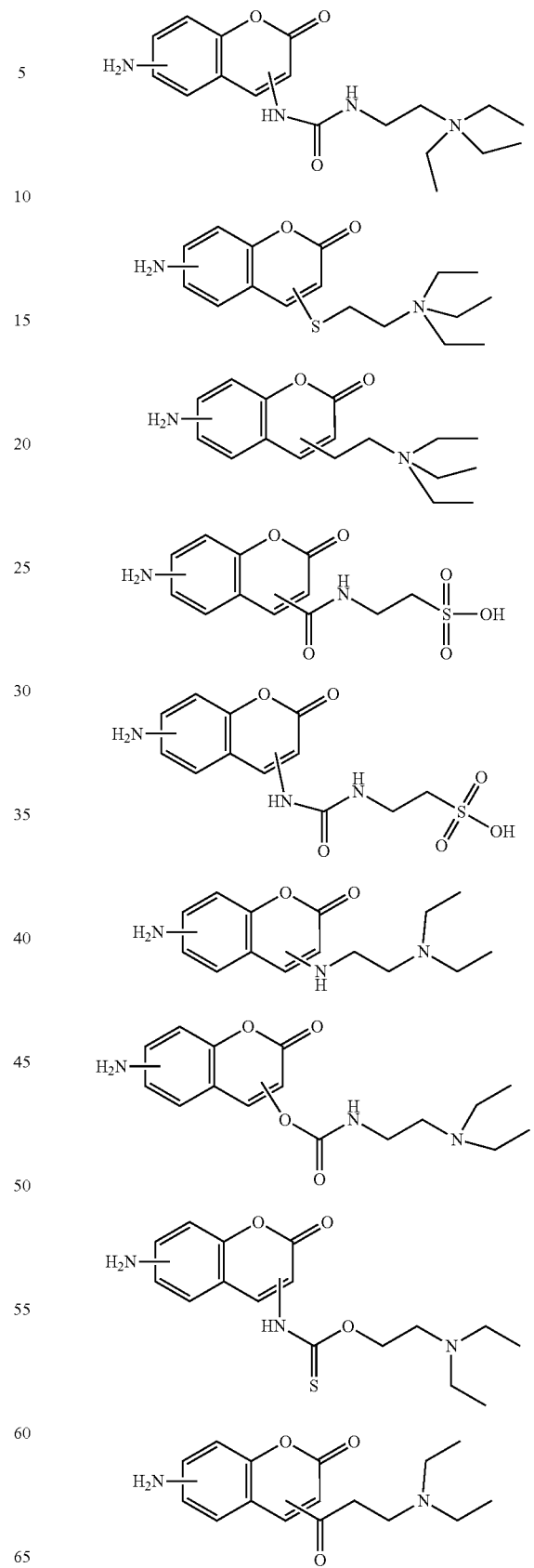

TABLE B-continued
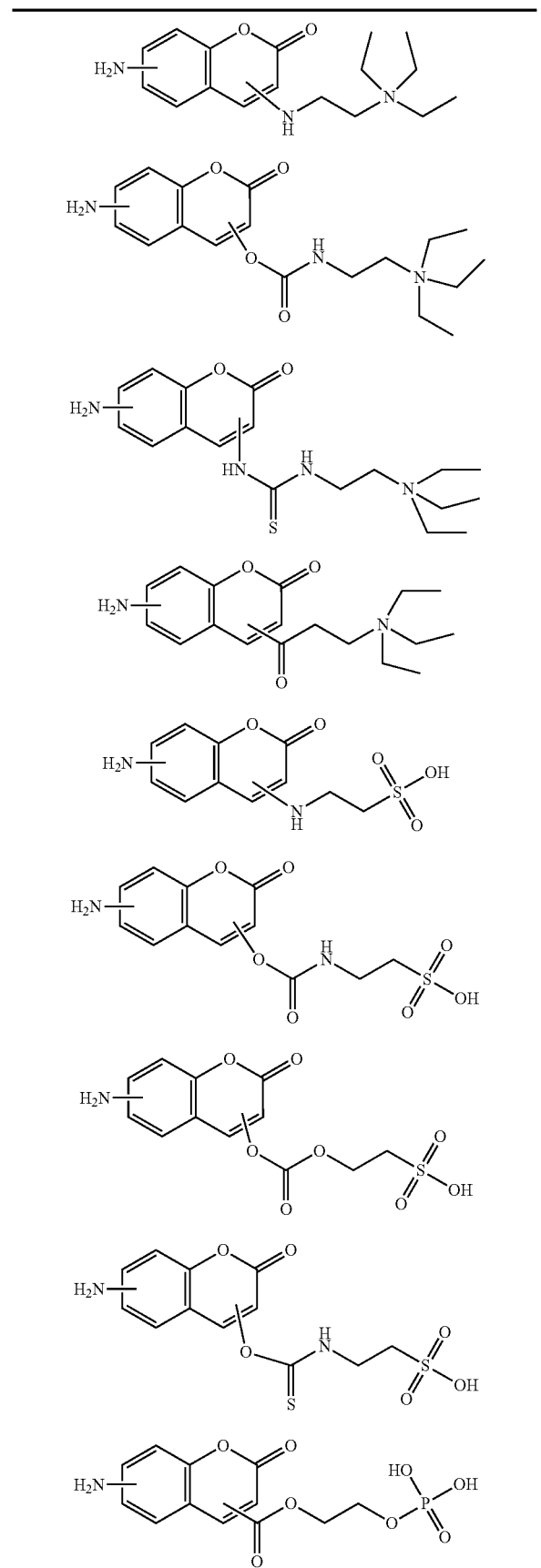
TABLE B-continued
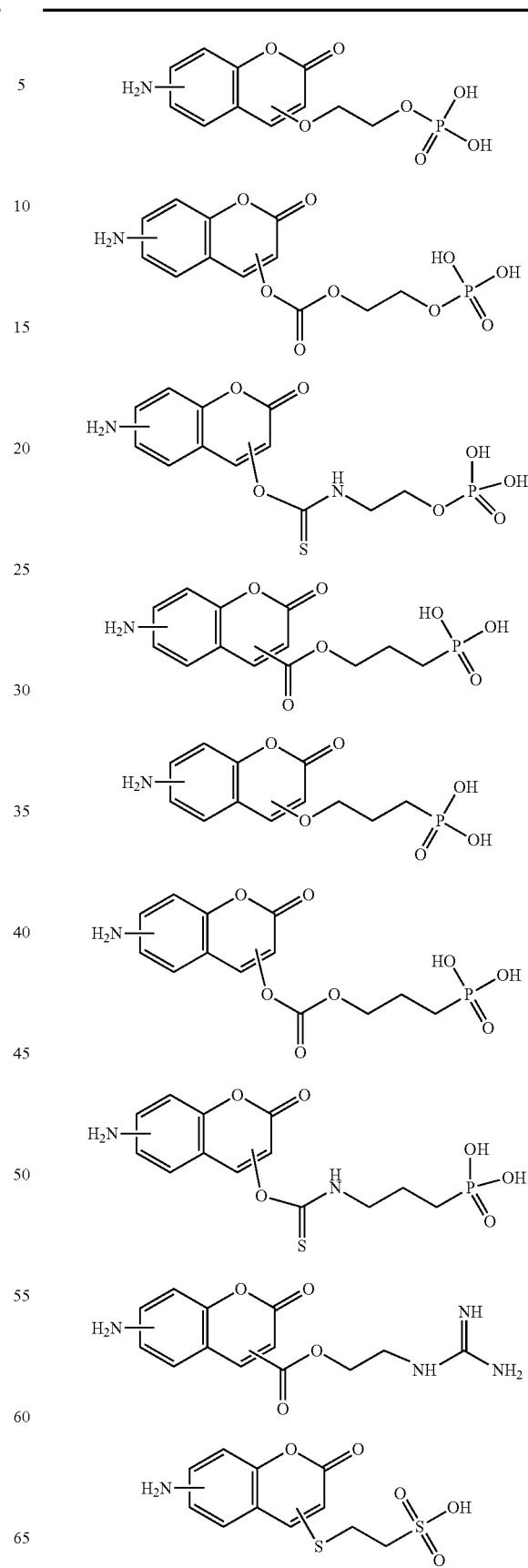

TABLE B-continued
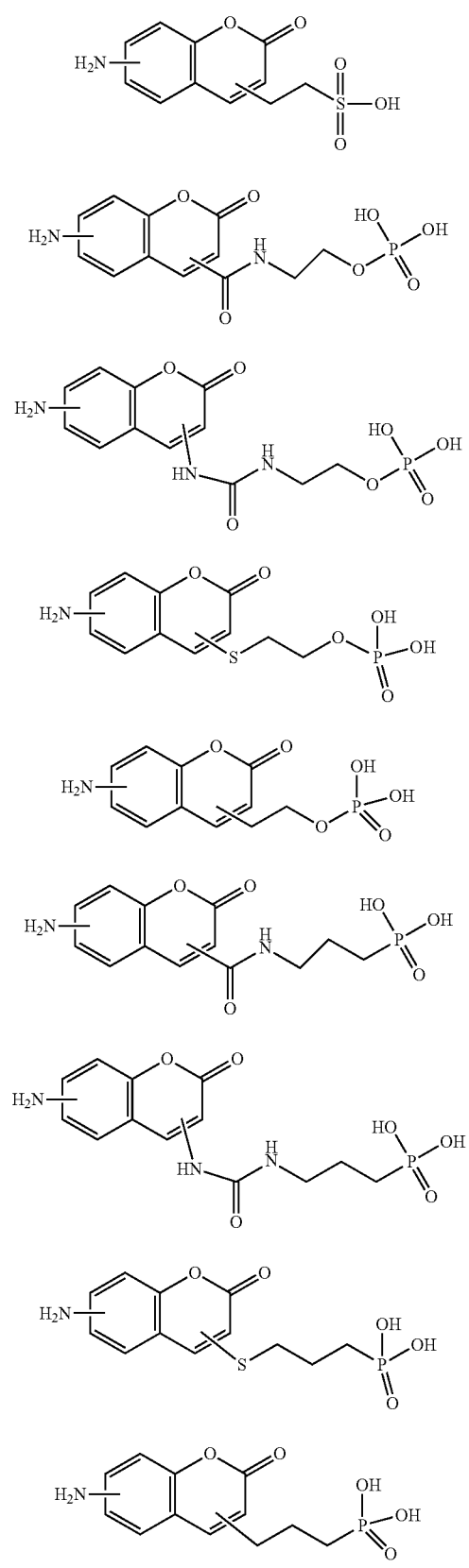
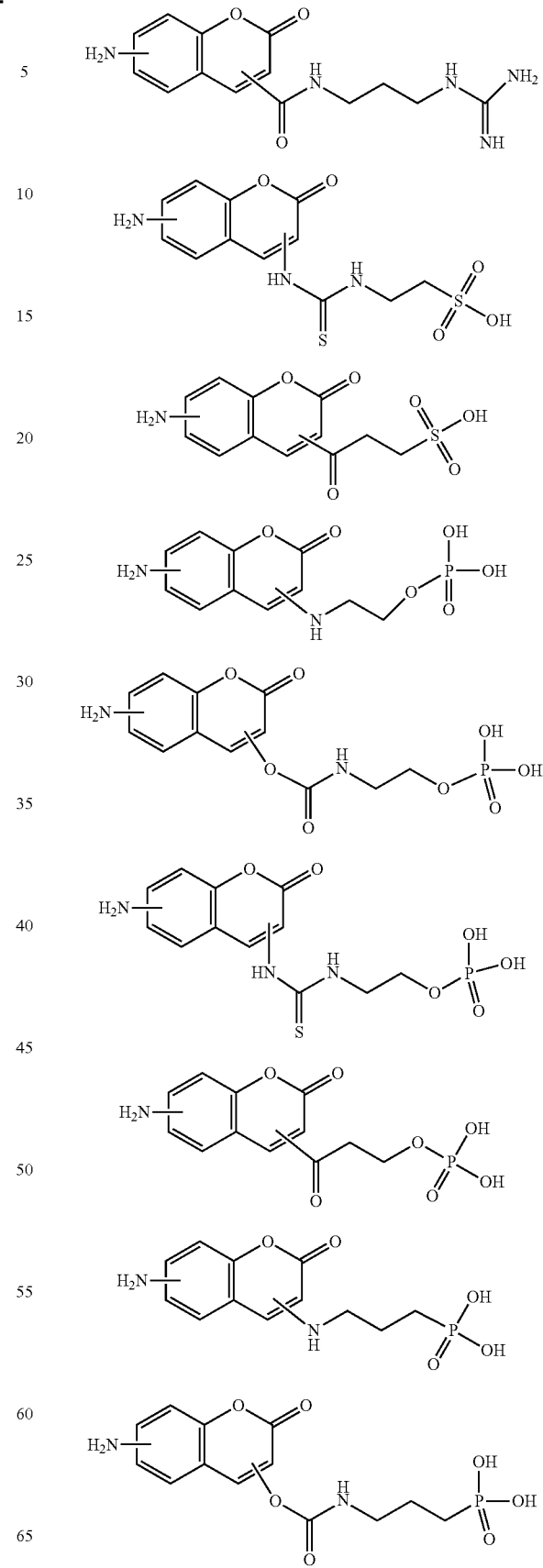

TABLE B-continued

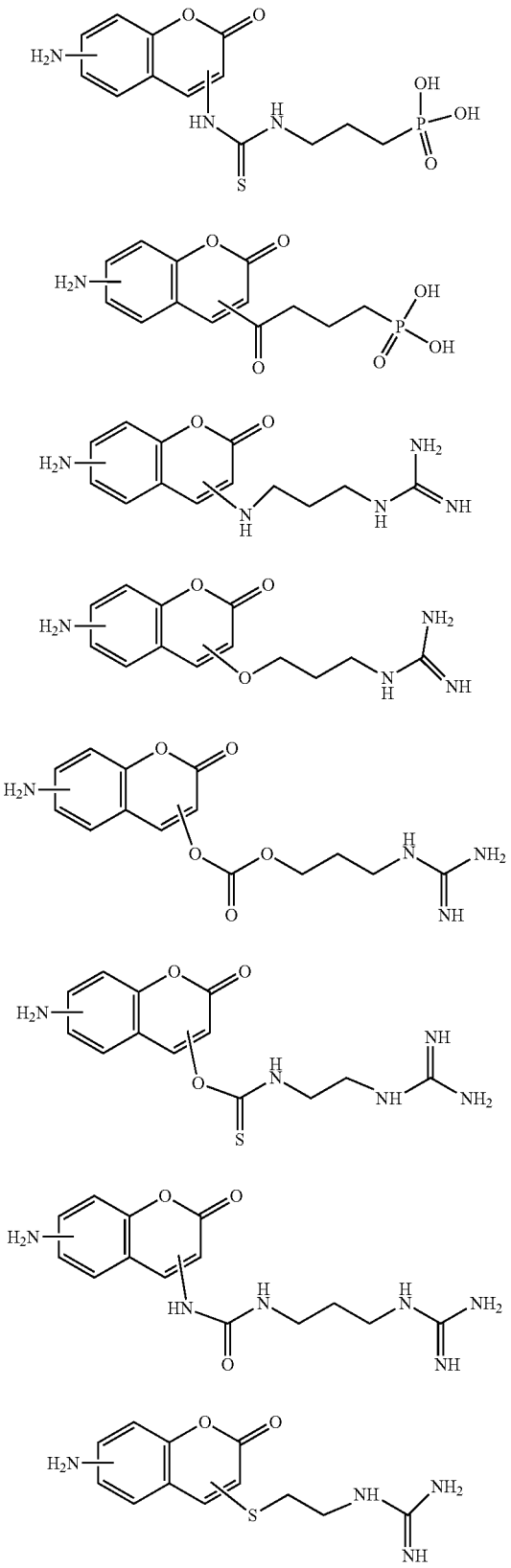

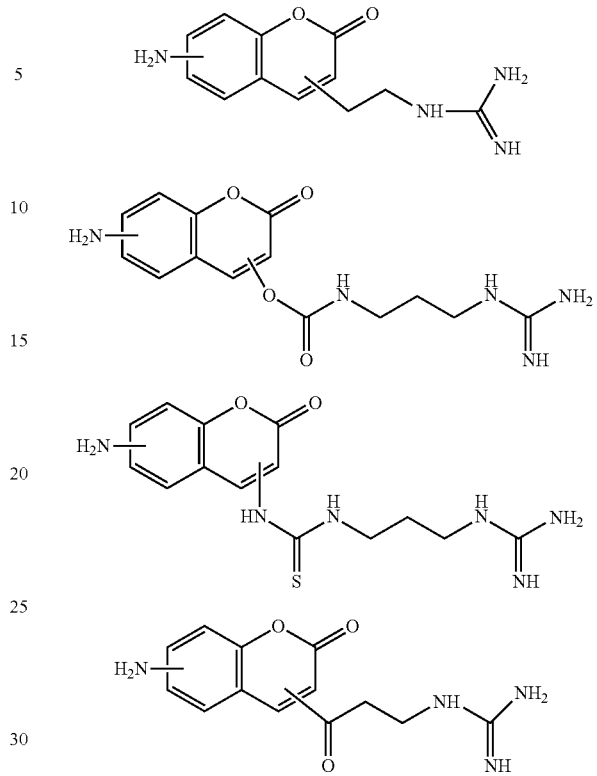

The methods for tagging, derivatizing or conjugating glycans containing at least one ketone group or an aldehyde group with a compound of Formula III, IIIA, IIIB, IIIC, IIID, IIIE, IIIF or IIIG or a compound of Table B by reductive amination reaction are provided. The reaction between a compound of Formula III and an aldehyde containing biopolymer, such as a glycan can be conducted under conditions that facilitate reductive amination in the presence of a reducing agent selected from sodium cyanoborohydride or sodium triacetoxyborohydride. The reaction can be carried out in a solution or suspension of a compound of Formula III, IIIA, IIIB, IIIC, IIID, IIIE, IIIF or IIIG or a compound of Table B in an acidic media, for example in citric acid or acetic acid, and mixing with a solution or suspension of a reducing agent such as cyanoborohydride or sodium triacetoxyborohydride in an organic solvent, for example, tetrohydrofuran or dimethylsulfoxide.

Methods for analyzing a glycan and other biomolecules containing an aldehyde group in a sample by means of liquid chromatography and mass spectrometry are provided. The analytical method comprises the steps of labeling the glycan in the sample by reacting with a compound of Formula III, IIIA, IIIB, IIIC, IIID, IIIE, IIIF or IIIG or a compound of Table B for a time and under conditions suitable to facilitate the labeling through reductive amination; and subjecting the labeled conjugate to liquid chromatography and mass spectrometry.

Glycans can be conjugated to MS active fluorescent compounds of Formula III and salts or solvates thereof. The following general schematic shows the tagging of a glycan using a compound of Formula III through reductive amination:

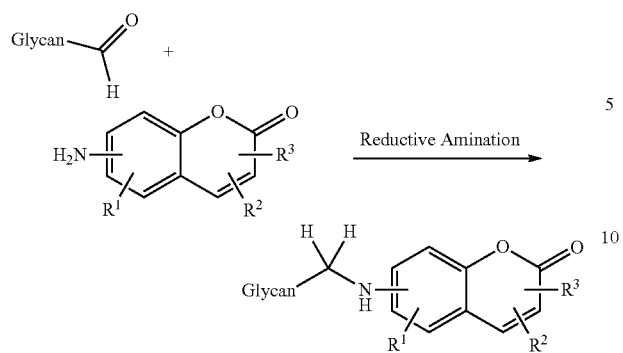

wherein FL $R^1$, $R^2$ and $R^3$ are as described above.

Naphthalene Based MS Active Fluorescence Tagging Compounds

Methods for tagging and analyzing glycans can be accomplished by fluorescence and mass spectroscopy following reductive amination of glycans with MS active, fluorescence tagging reagents of the structural Formula IV:

Formula IV

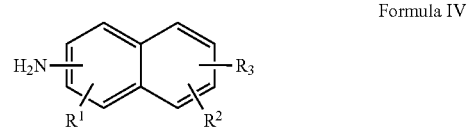

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^3$ is

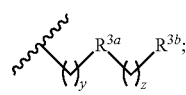

$R^{3a}$ is selected from ester, amide, amine, oxygen, urea, carbamate, carbonate, sulfur, thiourea, thiocarbamate, alkyl or carbonyl;
$R^{3b}$ is

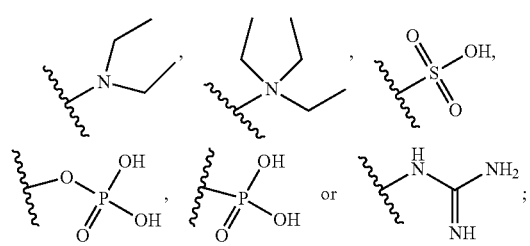

y=0-12;
z=1-12;
and salts or solvates thereof.

In an embodiment, methods for tagging glycans and other biomolecules with compounds of Formula IVA are provided:

Formula IVA

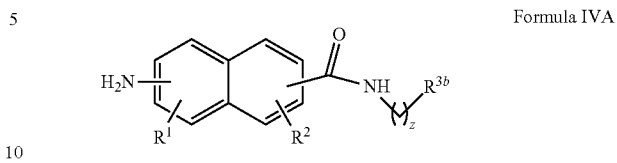

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

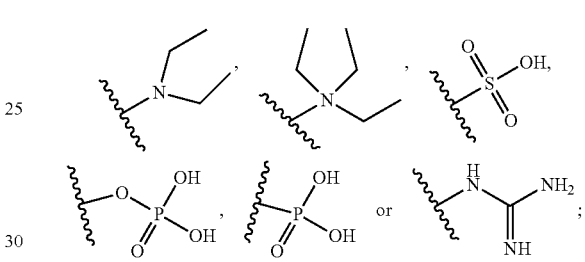

z=1-12; and salts or solvates thereof.

In an embodiment, methods for tagging glycans and other biomolecules with compounds of Formula IVB are provided:

Formula IVB

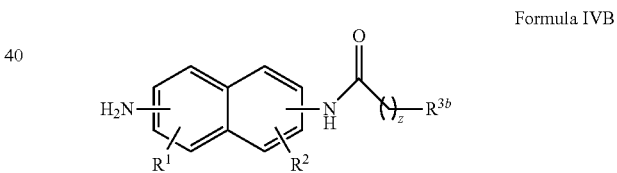

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

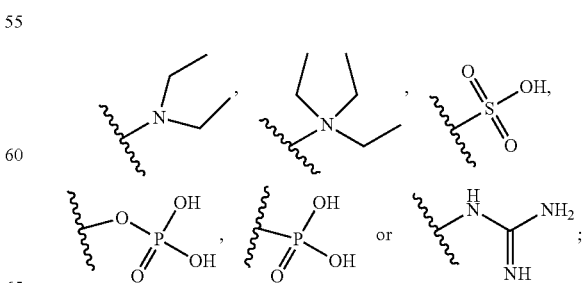

z=1-12; and salts or solvates thereof.

In an embodiment, methods for tagging glycans with compounds of Formula IVC are provided:

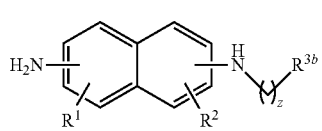

Formula IVC wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

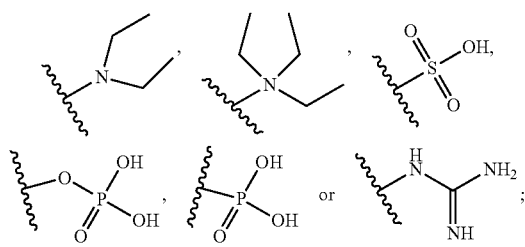

z=1-12;
and salts or solvates thereof.

In an embodiment, methods for tagging glycans with compounds of Formula IVD are provided:

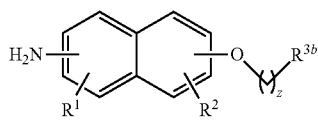

Formula IVD wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

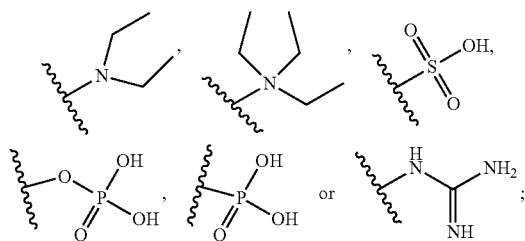

z=1-12;
and salts or solvates thereof.

In an embodiment, methods for tagging glycans with compounds of Formula IVE are provided:

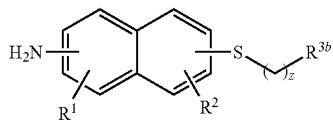

Formula IVE wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

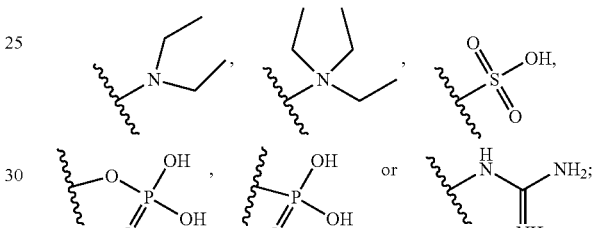

z=1-12;
and salts or solvates thereof.

In an embodiment, methods for tagging glycans with compounds of Formula IVF are provided:

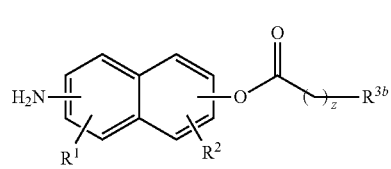

Formula IVF wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

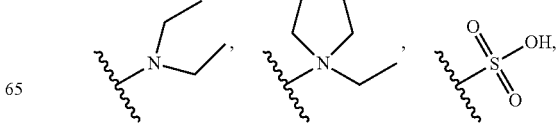

-continued

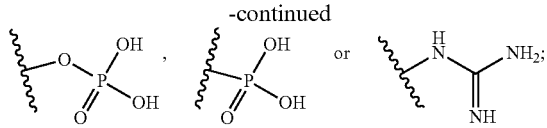

z=1-12;
and salts or solvates thereof.

In an embodiment, methods for tagging (labeling) glycans and other biomolecules with compounds of Formula IVG are provided:

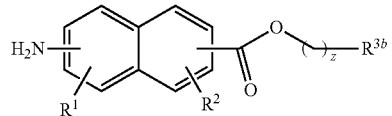

Formula IVG wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

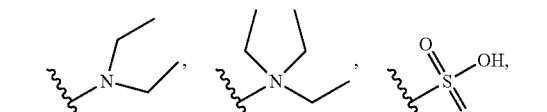

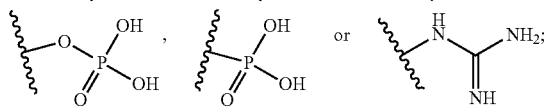

z=1-12;
and salts or solvates thereof.

In addition, provided below are exemplary compounds (Table C) of the structural Formulas IV, IVA, IVB, IVC, IVD, IVE, IVF or IVG which can be useful for fluorescent labeling of glycans and subsequent analysis by means of liquid chromatography and mass spectrometry. The compounds of structural Formulas IV, IVA, IVB, IVC, IVD, IVE, IVF or IVG could be optionally substituted with any group that does not substantially reduce the fluorescence of the compound.

The compounds of Formula IV, IVA, IVB, IVC, IVD, IVE, IVF or IVG include compounds wherein $R^1$ is hydrogen. In an embodiment, further provided are compounds of Formula IV, IVA, IVB, IVC, IVD, IVE, IVF or IVG including compounds wherein $R^2$ is hydrogen. In an embodiment, compounds of Formula IV, IVA, IVB, IVC, IVD, IVE, IVF or IVG include compounds wherein $R^1$ and $R^2$ are hydrogen.

TABLE C

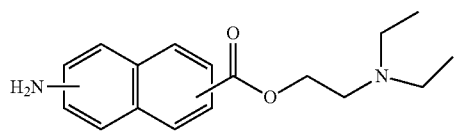

TABLE C-continued

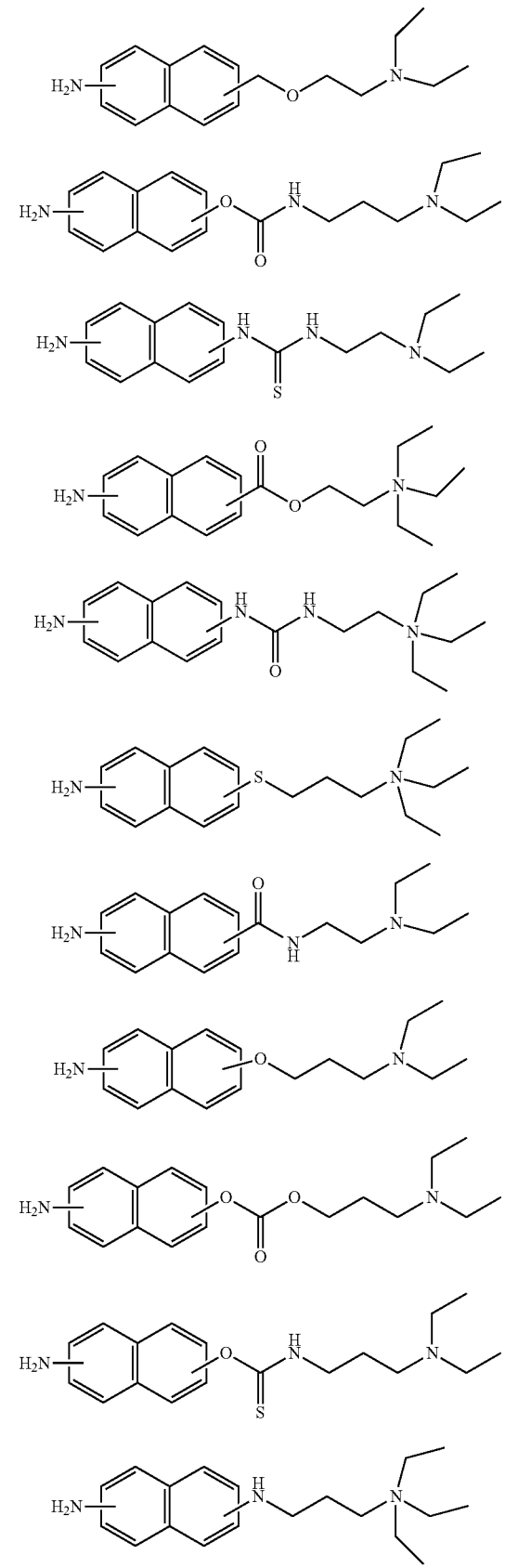

TABLE C-continued
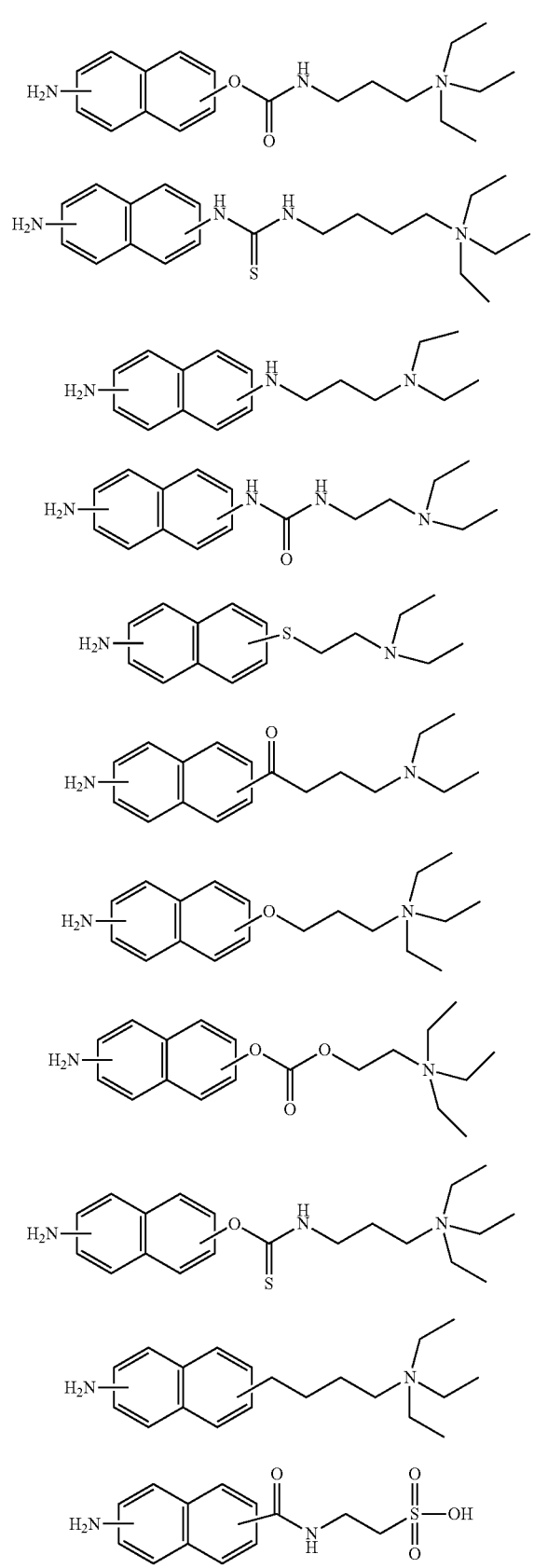
TABLE C-continued
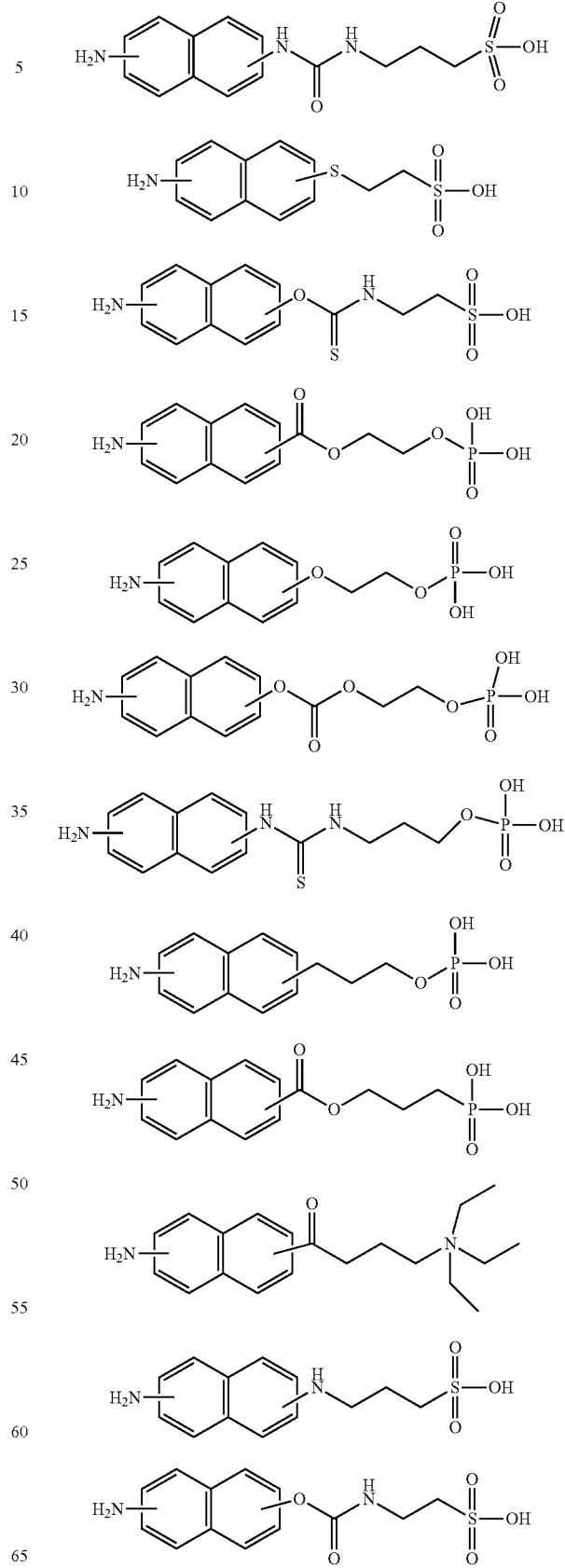

TABLE C-continued
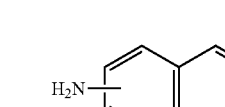

TABLE C-continued

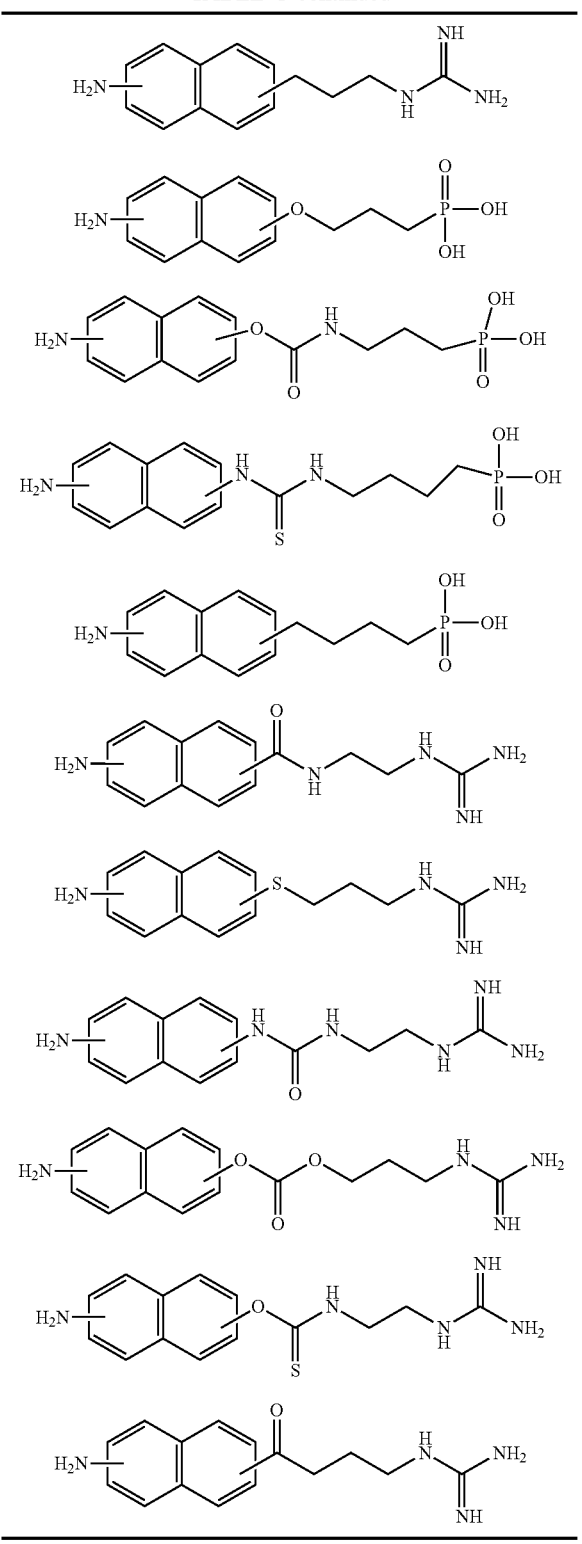

Methods for tagging, derivatizing or conjugating glycans and other biopolymers containing at least one ketone group or an aldehyde group with a compound of Formula IV, IVA, IVB, IVC, IVD, IVE, IVF or IVG or a compound of Table C by reductive amination reaction are further provided. The reaction between a compound of Formula II and an aldehyde containing biopolymer, such as a glycan can be conducted under conditions that facilitate reductive amination in the presence of a reducing agent, such as from sodium cyanoborohydride or sodium triacetoxyborohydride. The reaction can be carried out in a solution or suspension of a compound of Formula IV, IVA, IVB, IVC, IVD, IVE, IVF or IVG or a compound of Table B in an acidic media, for example in citric acid or acetic acid, and by mixing with a solution or suspension of a reducing agent such as cyanoborohydride or sodium triacetoxyborohydride in an organic solvent, for example, tetrohydrofuran or dimethylsulfoxide.

Methods for analyzing a glycan and other biomolecules containing an aldehyde group in a sample by means of liquid chromatography and mass spectrometry are provided. The analytical method comprises the steps of labeling the biomolecule, such as a glycan, in the sample by reacting with a compound of Formula IV, IVA, IVB, IVC, IVD, IVE, IVF or IVG for a time and under conditions suitable to facilitate the labeling through reductive amination; and subjecting the labeled conjugate to liquid chromatography and mass spectrometry.

Glycans can be conjugated to MS active fluorescent compounds of Formula IV and salts or solvates thereof. The following general schematic shows the tagging of a glycan using a compound of Formula IV through reductive amination:

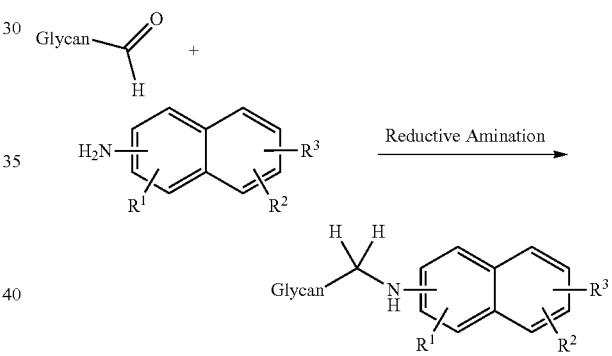

wherein FL $R^1$, $R^2$ and $R^3$ are as described above.

Rhodamine Based MS Active Fluorescence Tagging Compounds

Methods for labeling (tagging) and analyzing glycans can be accomplished by fluorescence and mass spectroscopy following reductive amination of glycans with compounds of the structural Formula V, VI, VII, VIII or IX:

Formula V

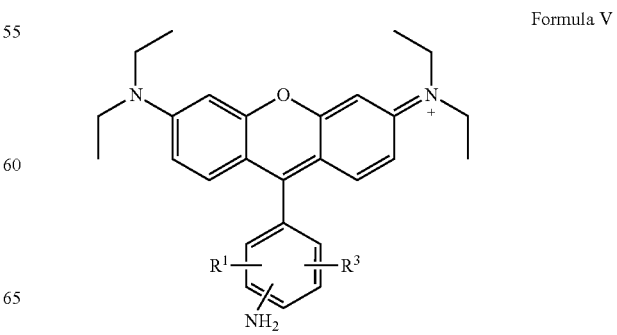

-continued

Formula VI

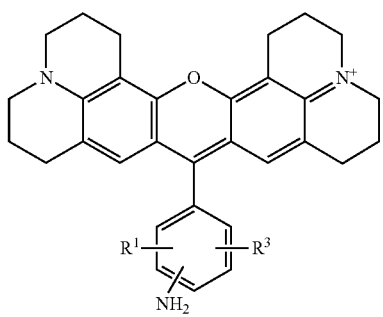

Formula VII

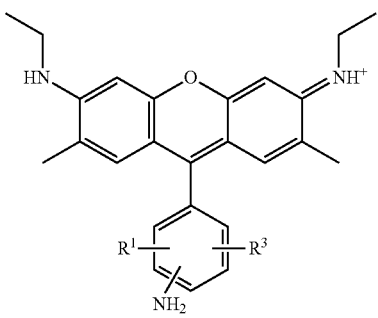

Formula VIII

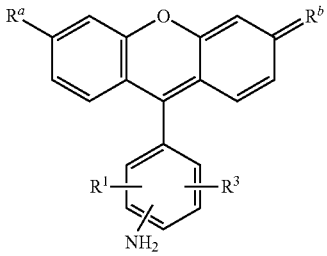

Formula IX

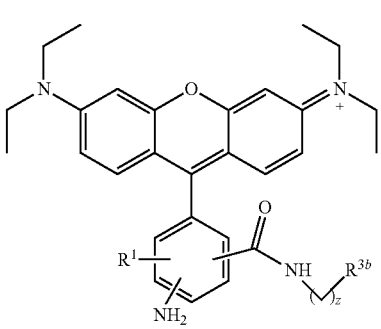

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^3$ is

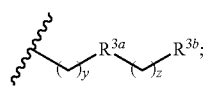

$R^{3a}$ is selected from ester, amide, amine, oxygen, urea, carbamate, carbonate, sulfur, thiourea, thiocarbamate, alkyl or carbonyl;
$R^{3b}$ is

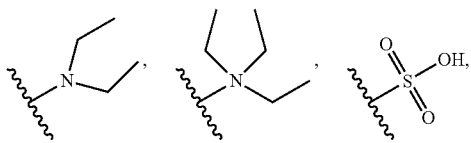

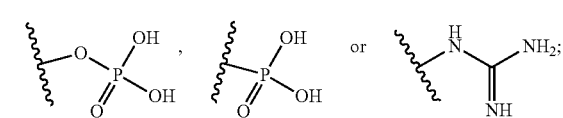

$y=0-12$;
$z=1-12$;
$R^a$ is selected from

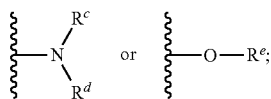

$R^b$ is oxo or

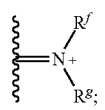

$R^c$, $R^d$, $R^e$, $R^f$ and $R^g$ are independently selected from hydrogen and optionally substituted alkyl; and salts or solvates thereof.

In an embodiment, methods for tagging glycans and other biomolecules with compounds of Formula VA, VIA, VIIA, VIIIA or IXA, and salts or solvates thereof, are provided.

Formula VA

-continued

Formula VIA

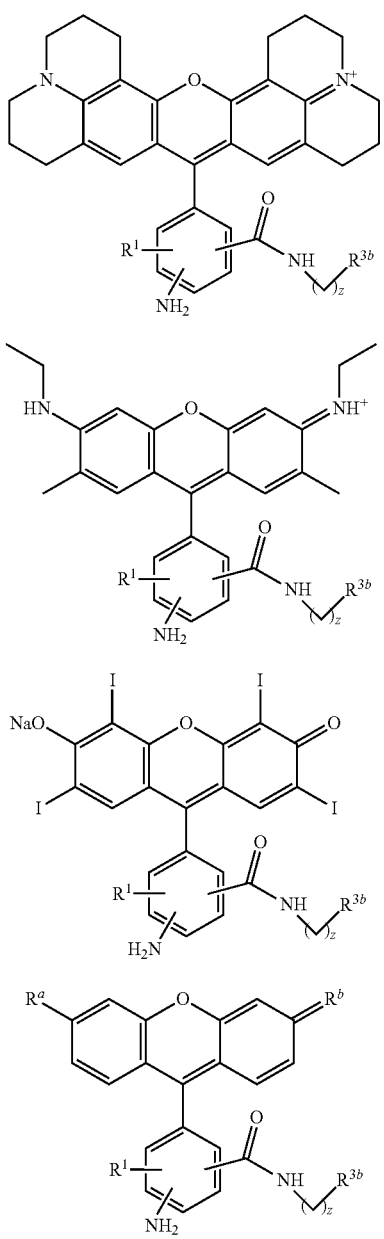

Formula VIIA

Formula VIIIA

Formula IXA wherein
each of R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

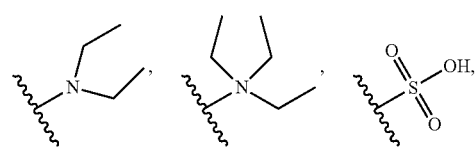

-continued

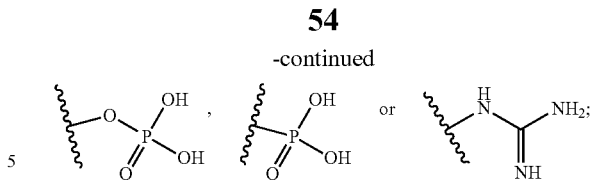

$z = 1-12$;

$R^a$ is selected from

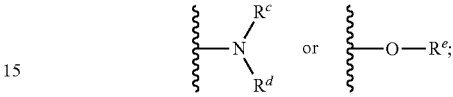

$R^b$ is oxo or

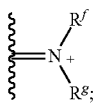

and $R^c$, $R^d$, $R^e$, $R^f$ and $R^g$ are independently selected from hydrogen and optionally substituted alkyl.

In an embodiment, methods for tagging glycans and other biomolecules with compounds of Formula VB, VIB, VIIB, VIIIB or IXB or salts and solvates thereof, are provided wherein each of R¹ and R² is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

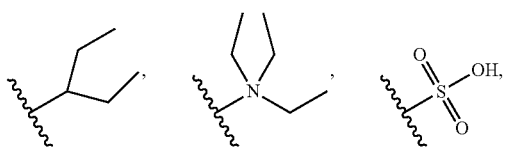

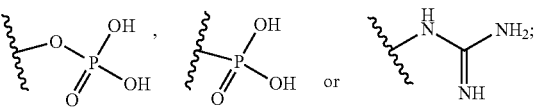

$z = 1-12$;

$R^a$ is selected from

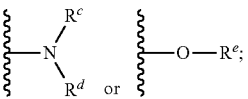

$R^b$ is oxo or

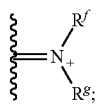

$R^c$, $R^d$, $R^e$, $R^f$ and $R^g$ are independently selected from hydrogen and optionally substituted alkyl; and salts or solvates thereof.

In an embodiment, methods for tagging glycans and other biomolecules with compounds of Formula VC, VIC, VIIC, VIIIC or IXC, or salts and solvates thereof are provided:

Formula VC

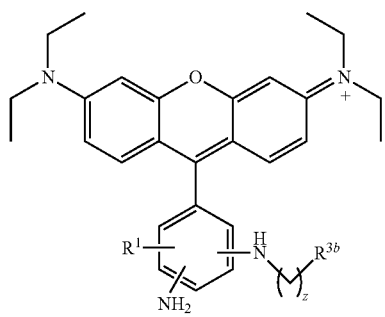

Formula VIC

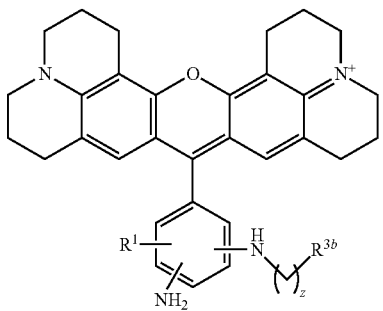

Formula VIIC

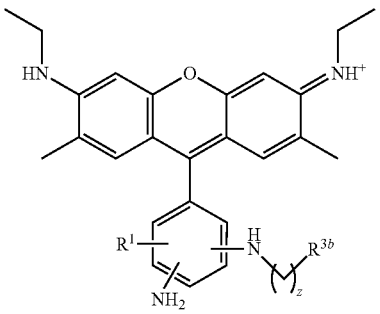

Formula VIIIC

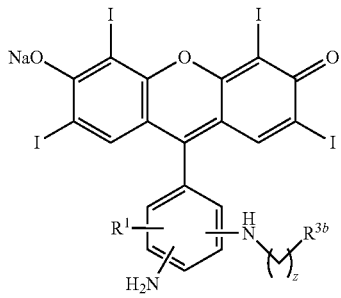

Formula IXC

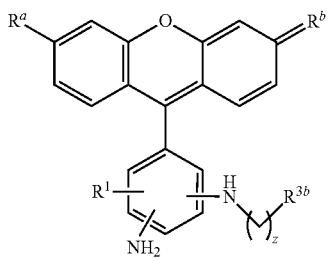

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $R^{3b}$ is

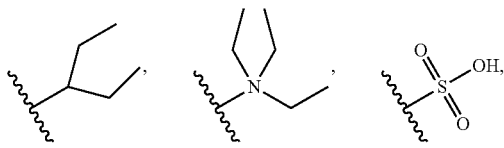

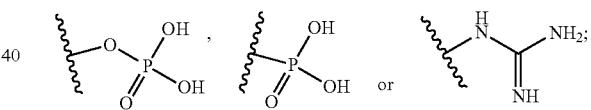

$R^a$ is selected from

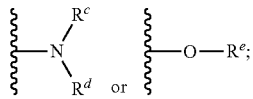

$R^b$ is oxo or

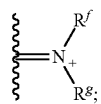

$R^c$, $R^d$, $R^e$, $R^f$ and $R^g$ are independently selected from hydrogen and optionally substituted alkyl; and salts or solvates thereof.

In an embodiment, methods for tagging glycans and other biomolecules with compounds of Formula VD, VID, VIID, VIIID or IXD, or salts or solvates, are provided.

Formula VD
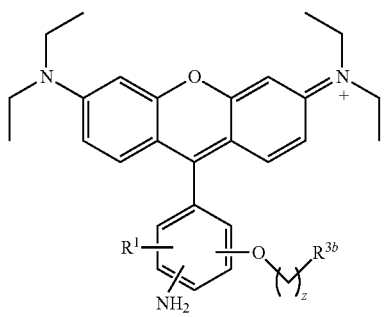

Formula VID
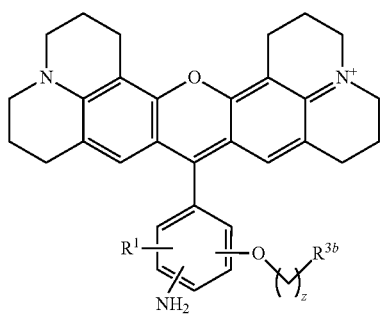

Formula VIID
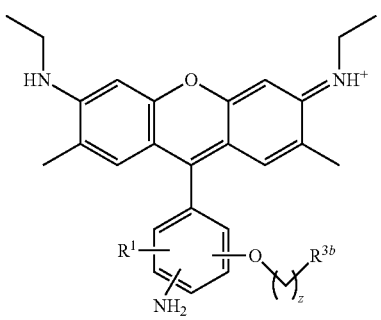

Formula VIIID
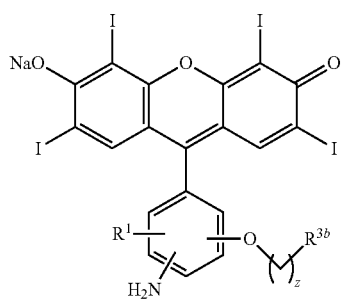

Formula IXD
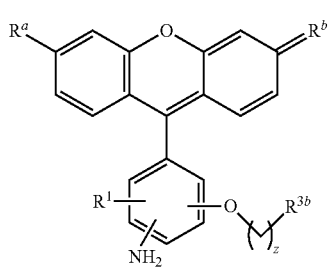

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

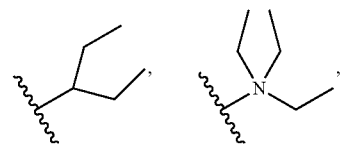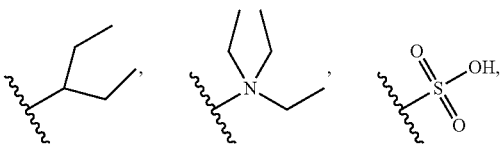

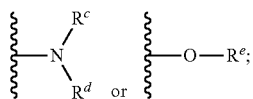

z=1-12;

$R^a$ is selected from

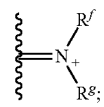

$R^b$ is oxo or;

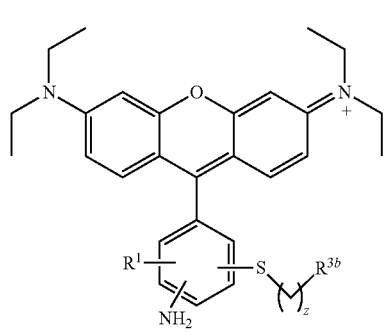

$R^c$, $R^d$, $R^e$, $R^f$ and $R^g$ are independently selected from hydrogen and optionally substituted alkyl; and salts or solvates thereof.

In an embodiment, methods for tagging glycans and other biomolecules with compounds of Formula VE, VIE, VIIE, VIIIE or IXE are provided:

Formula VE

Formula VIE

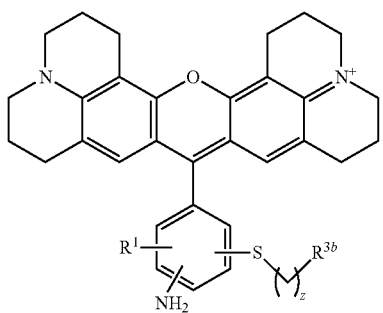

Formula VIIE

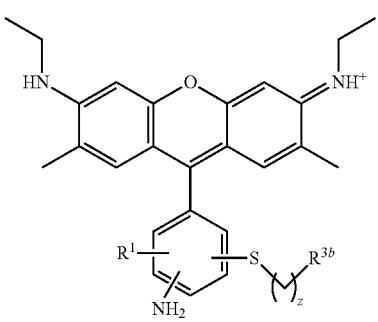

Formula VIIIE

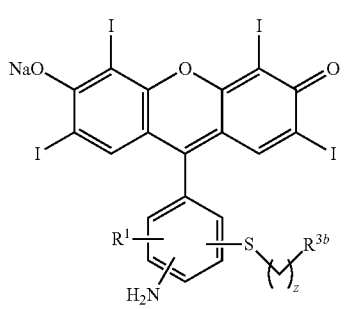

Formula IXE

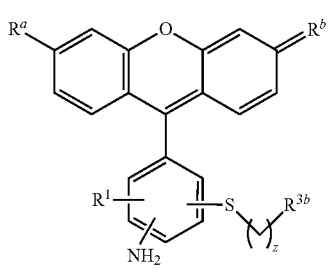

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

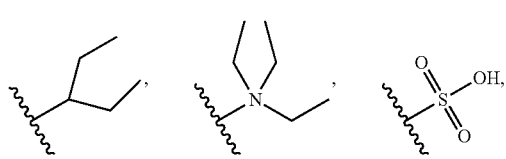

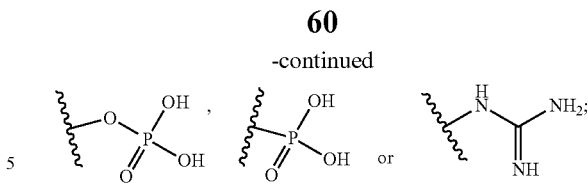

z=1-12;

$R^a$ is selected from

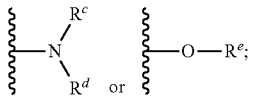

$R^b$ is oxo or;

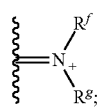

$R^c$, $R^d$, $R^e$, $R^f$ and $R^g$ are independently selected from hydrogen and optionally substituted alkyl; and salts or solvates thereof.

In addition, provided below are exemplary compounds (Table D) of the structural Formulas V, VI, VII, VIII and IX which can be useful for fluorescent labeling of glycans and subsequent analysis by means of liquid chromatography and mass spectrometry. The compounds of structural Formulas V, VI, VII, VIII and IX could be optionally substituted with any group that does not substantially reduce the fluorescence of the compound.

TABLE D

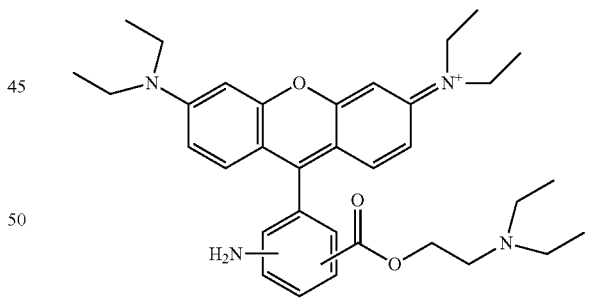

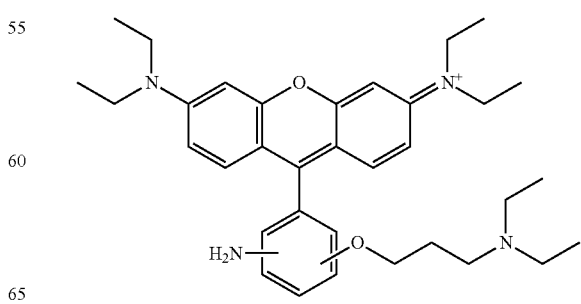

TABLE D-continued
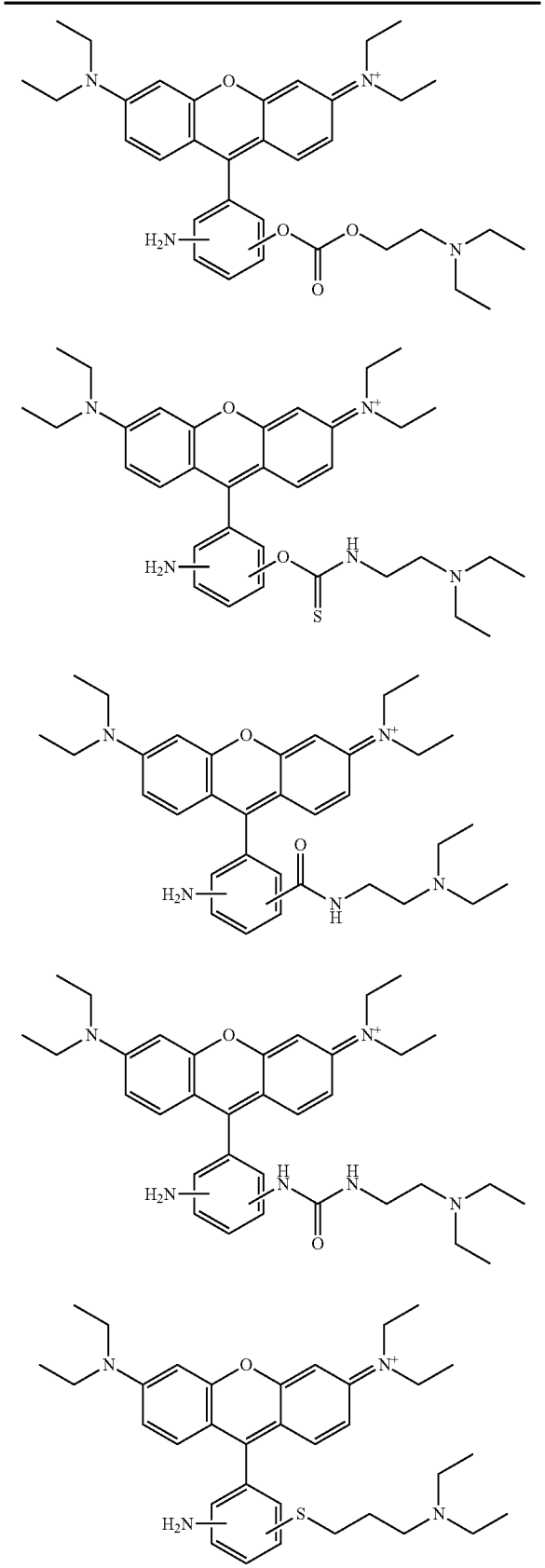
TABLE D-continued
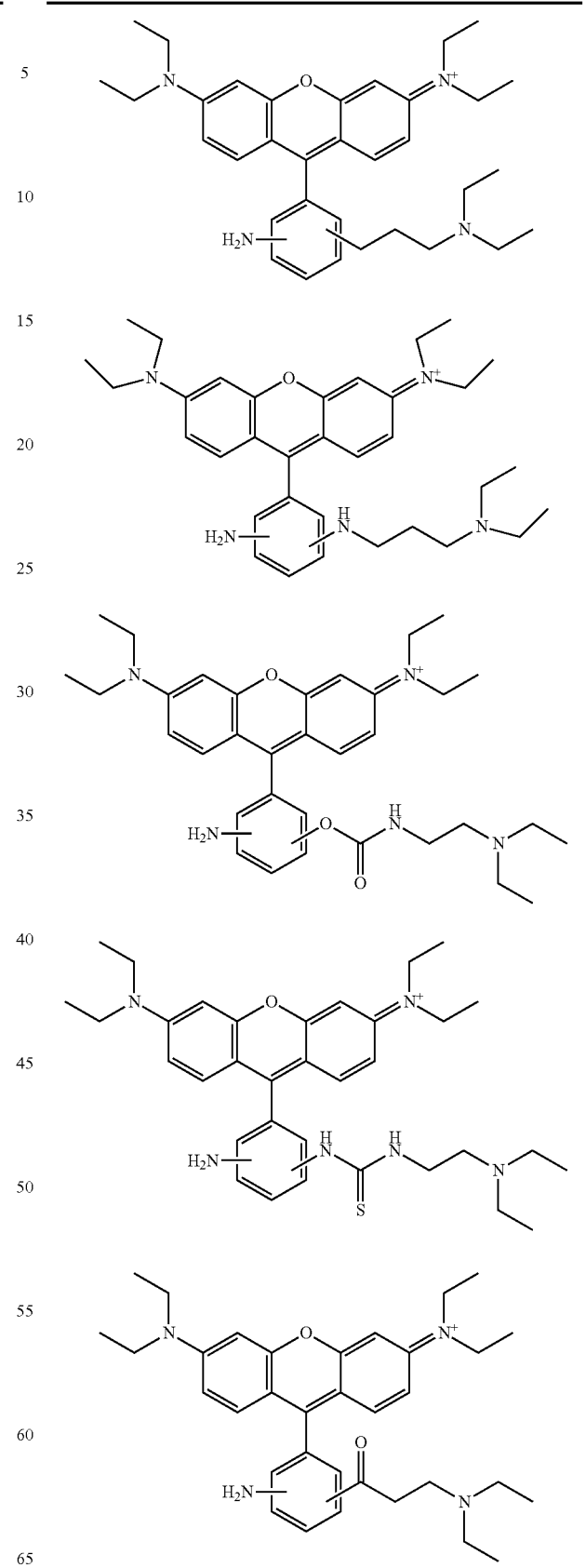

TABLE D-continued
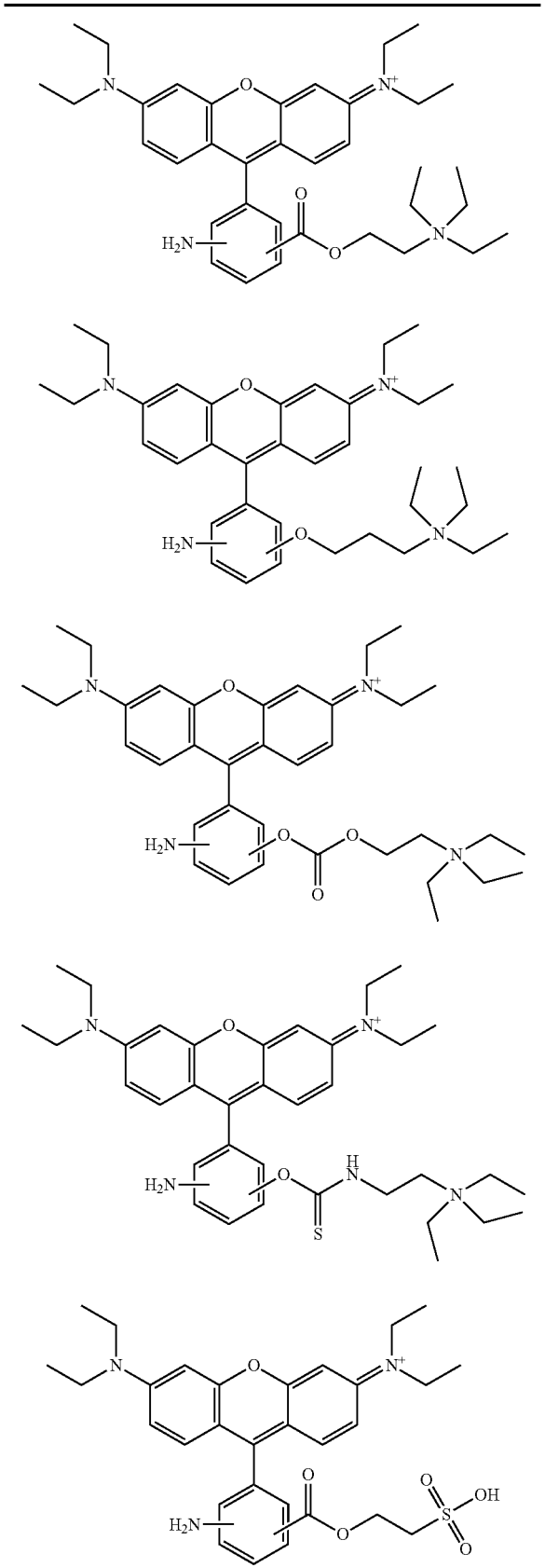
TABLE D-continued
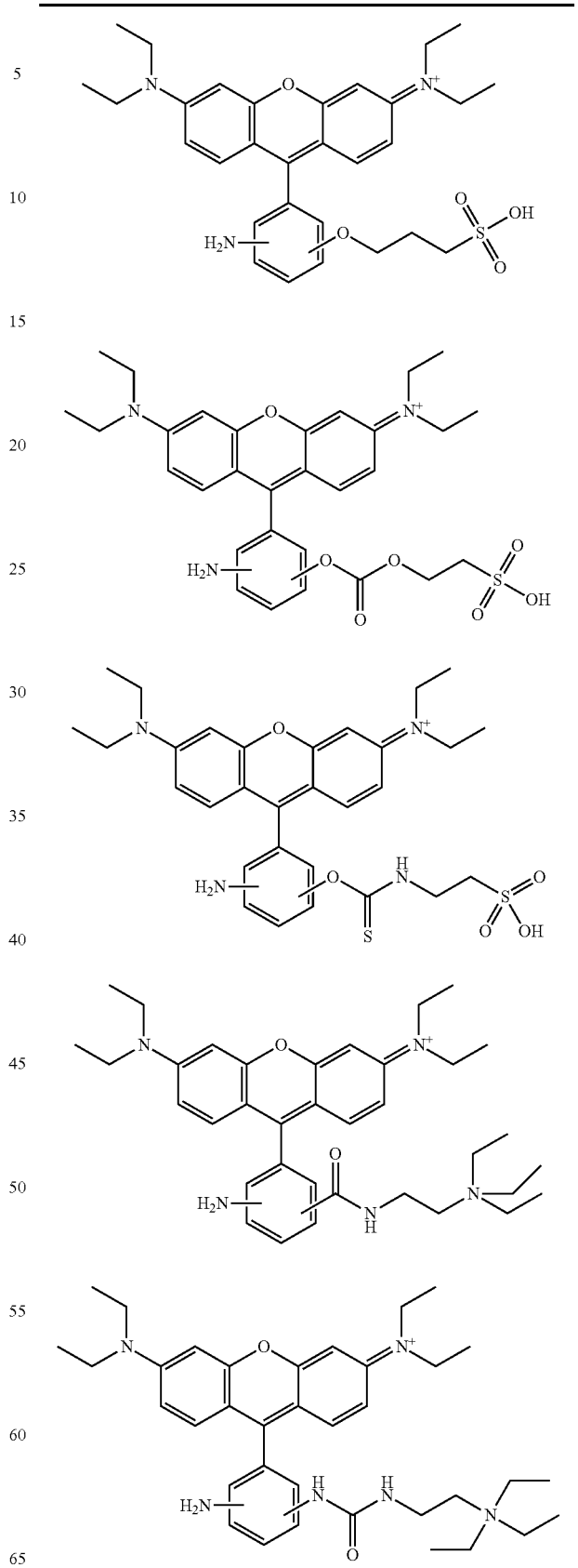

TABLE D-continued
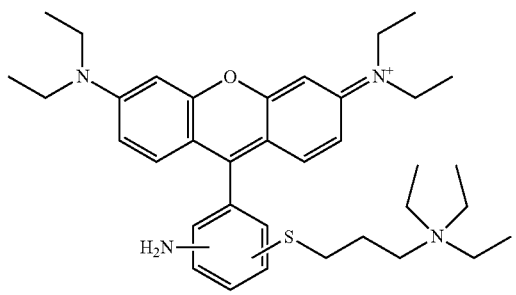
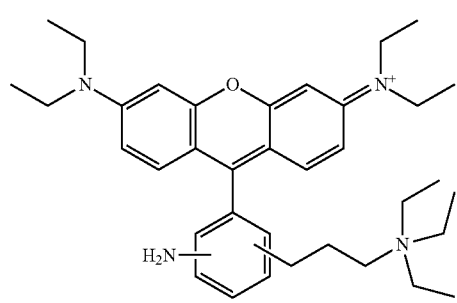
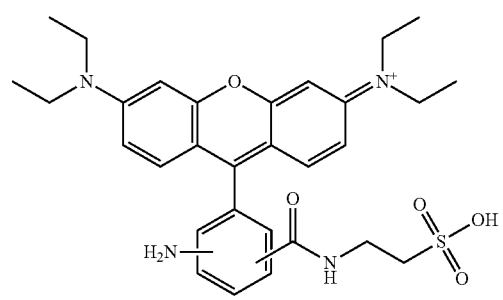
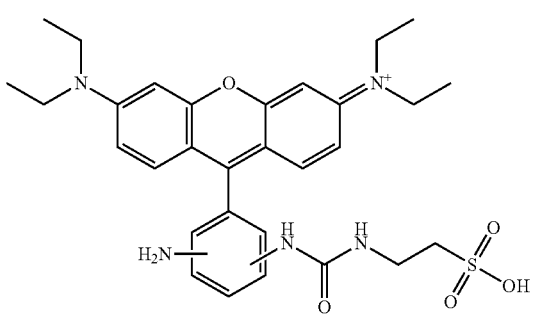
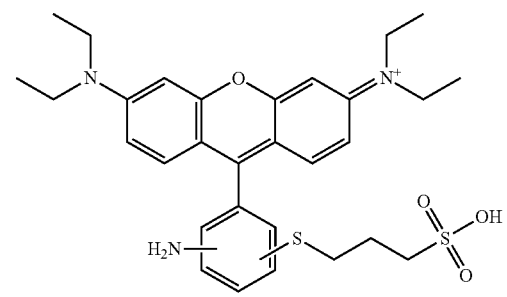
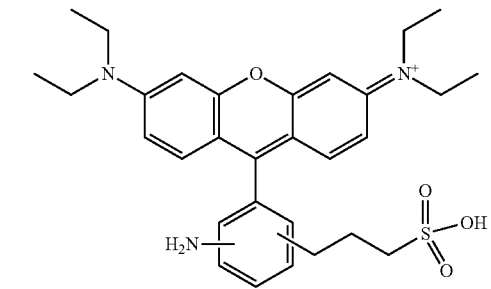
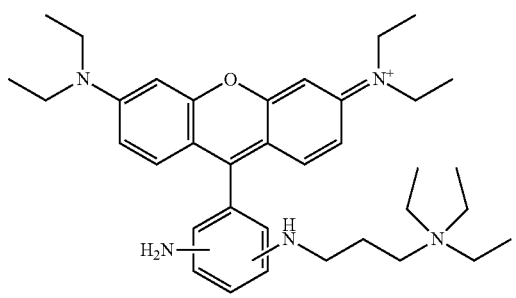
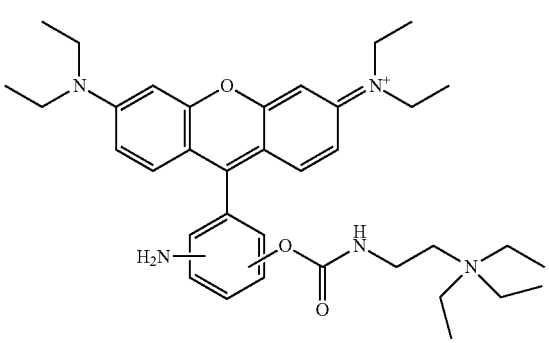
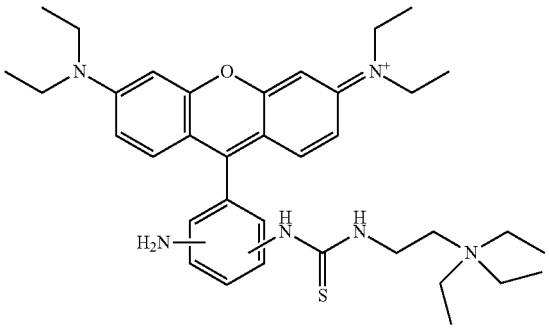
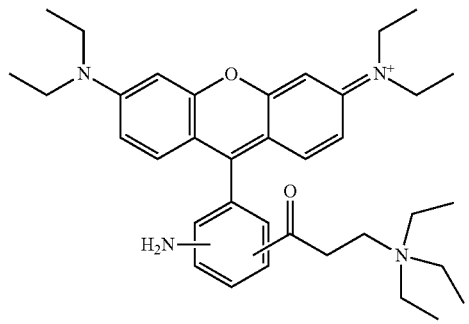

TABLE D-continued
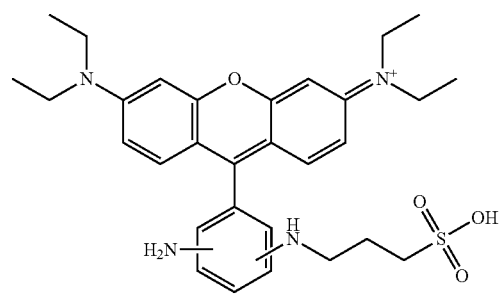
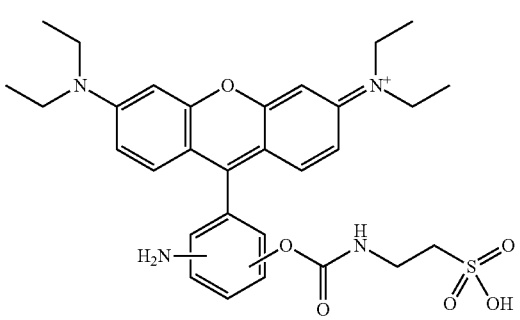
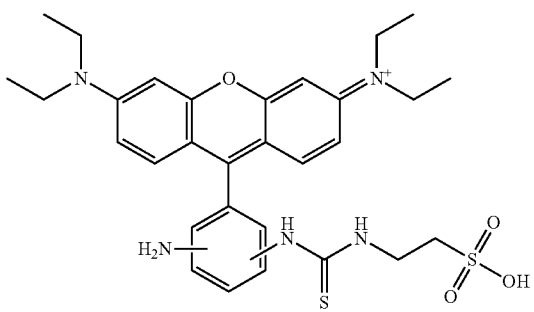
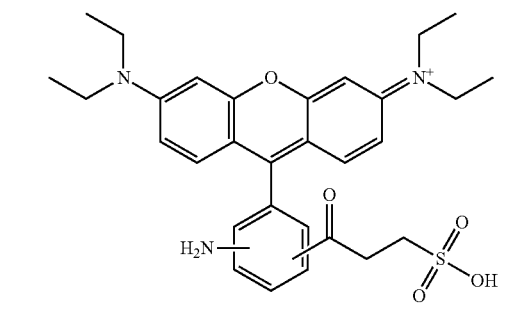
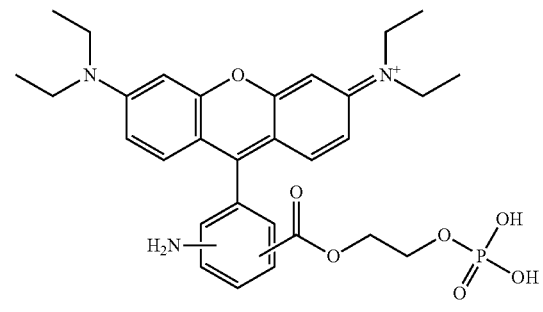
TABLE D-continued
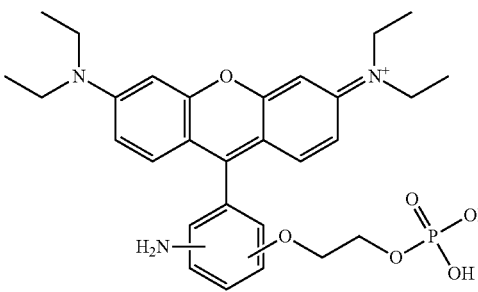
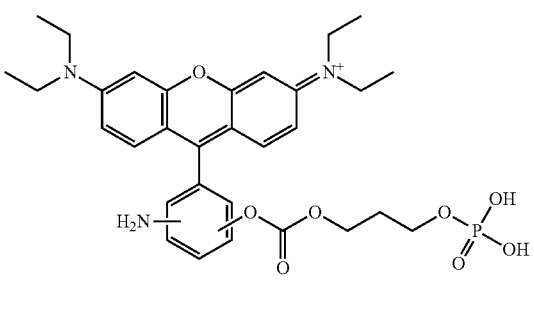
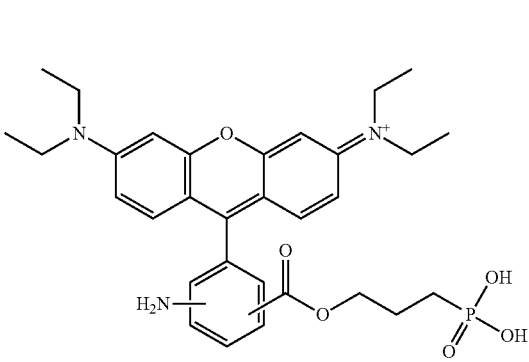
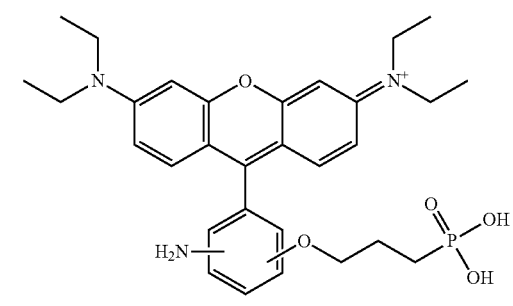

TABLE D-continued
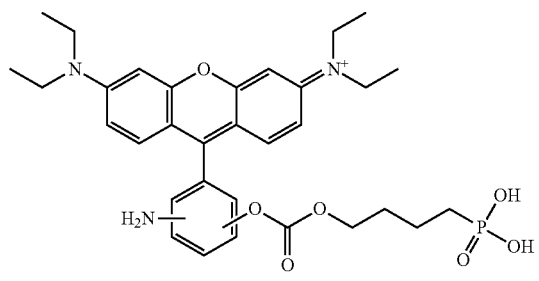
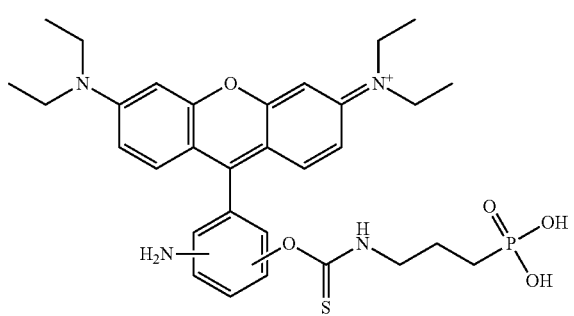
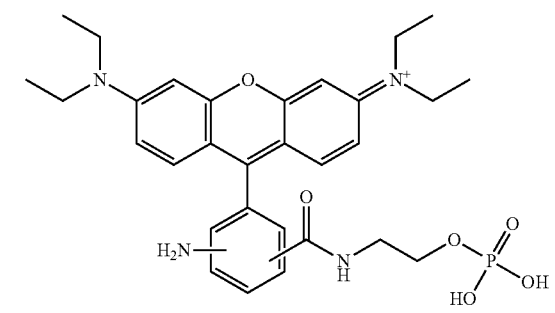
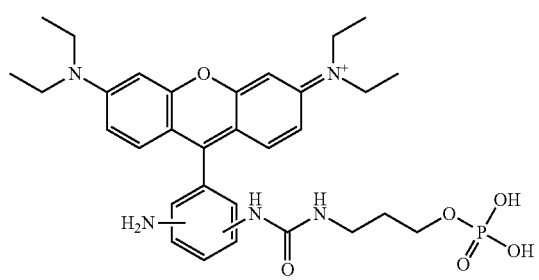
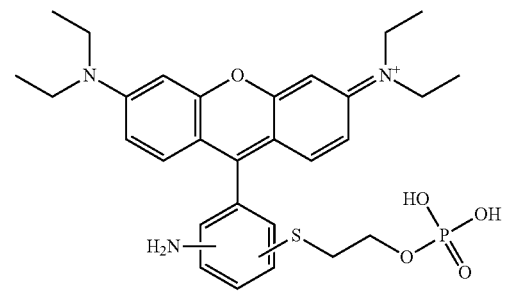
TABLE D-continued
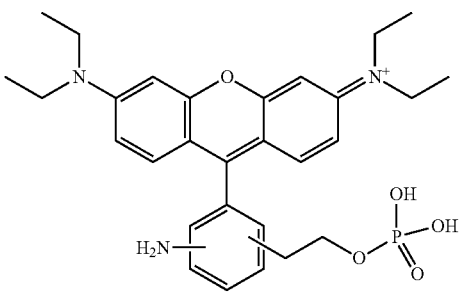
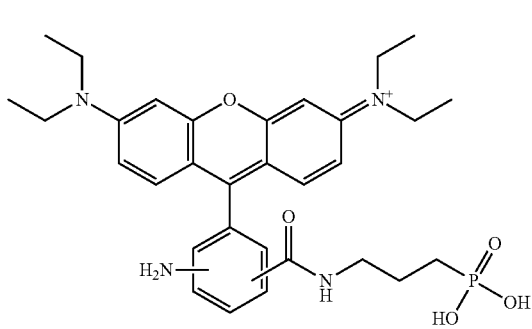
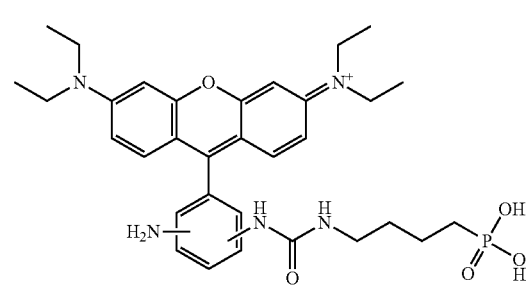
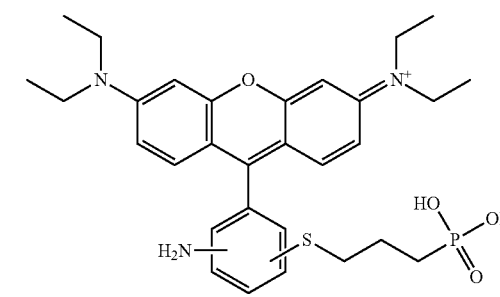
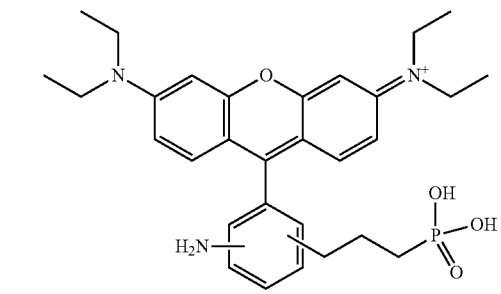

TABLE D-continued
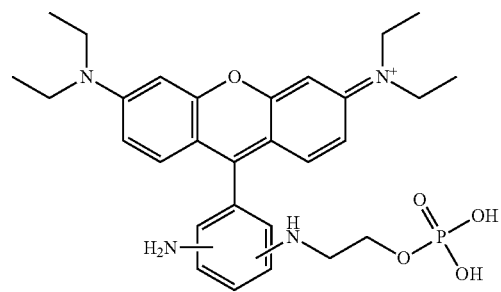
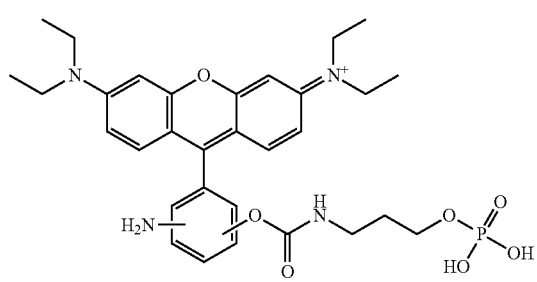
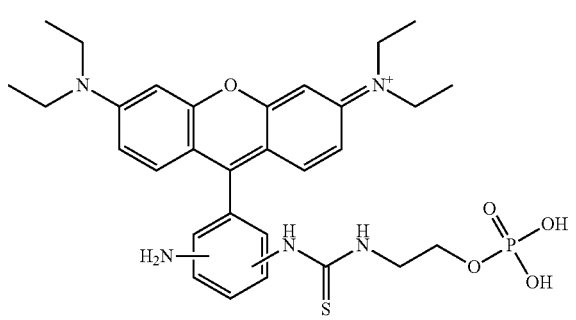
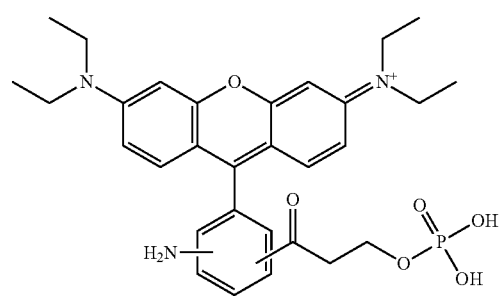
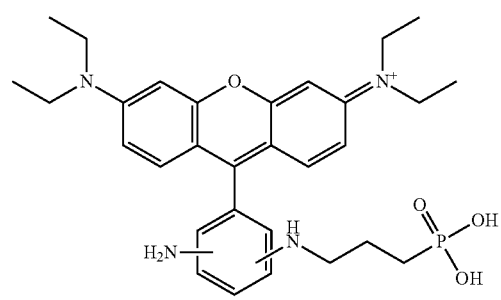
TABLE D-continued
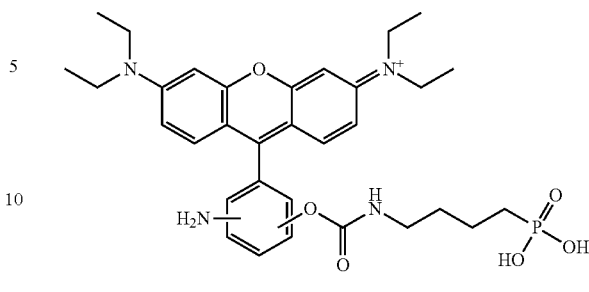
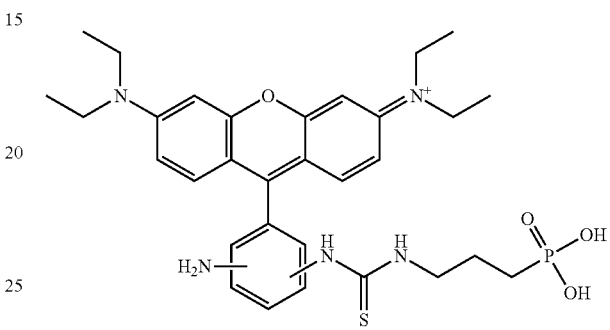
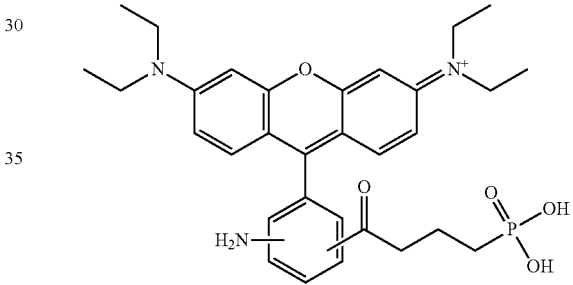
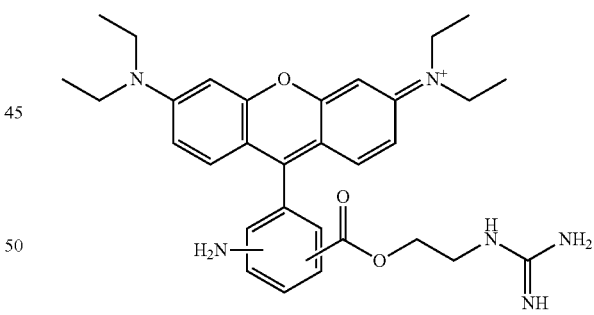
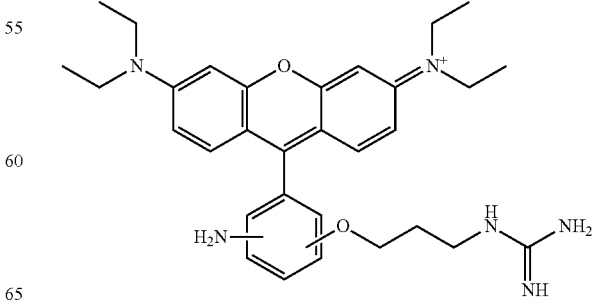

TABLE D-continued
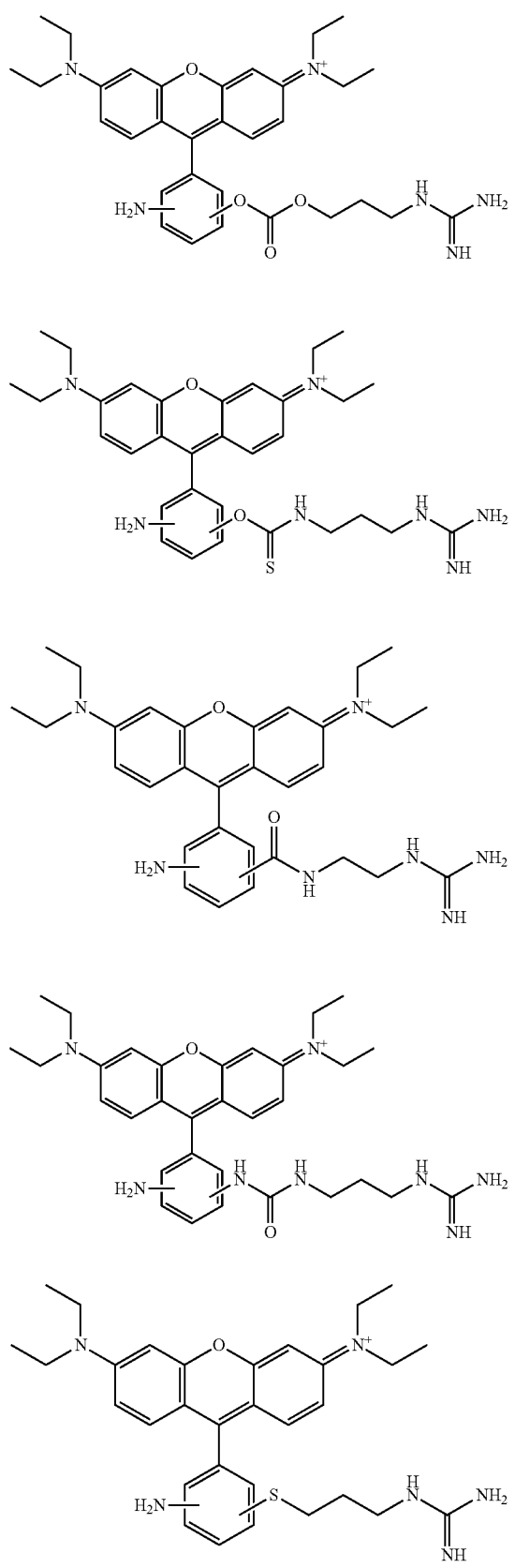
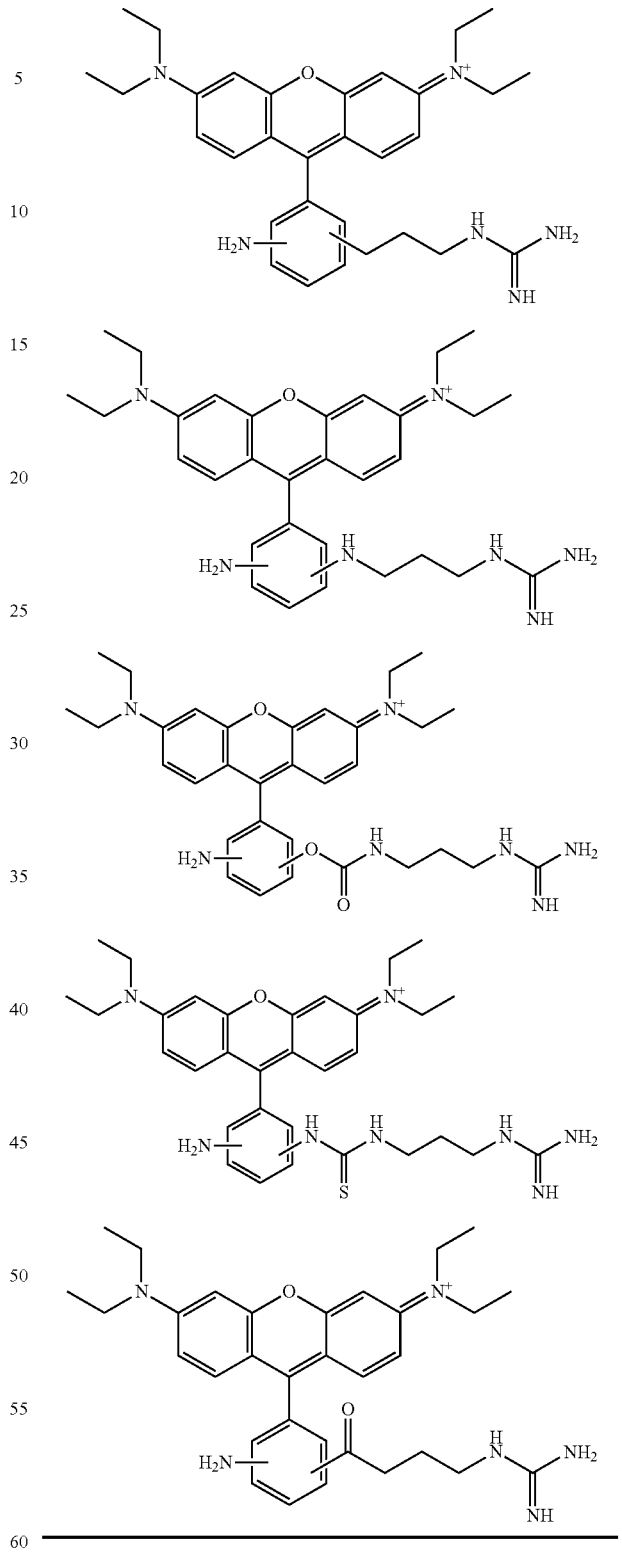
In an embodiment, provided herein are compounds of V, VI, VII, VIII or IX wherein $R^1$ is hydrogen. In an embodiment, further provided are compounds of Formula V, VI, VII, VIII or IX wherein $R^2$ is hydrogen. In an embodiment, compounds of Formula V, VI, VII, VIII or IX include compounds wherein $R^1$ and $R^2$ are hydrogen.

Methods for tagging, derivatizing or conjugating glycans and other biopolymers containing at least one ketone group or an aldehyde group, with a compound of Formula V, VI, VII, VIII, IX or a compound of Table D by reductive amination reaction are further provided. The reaction between a compound of Formula V, VI, VII, VIII or IX and an aldehyde containing biopolymer, such as a glycan can be conducted under conditions that facilitate reductive amination in the presence of a reducing agent, such as from sodium cyanoborohydride or sodium triacetoxyborohydride. The reaction can be carried out in a solution or suspension of a compound of Formula V, VI, VII, VIII or IX or a compound of Table D in an acidic media, for example in citric acid or acetic acid, and by mixing with a solution or suspension of a reducing agent such as cyanoborohydride or sodium triacetoxyborohydride in an organic solvent, for example, tetrohydrofuran or dimethylsulfoxide.

Methods for analyzing a glycan and other biomolecules containing an aldehyde group in a sample by means of liquid chromatography and mass spectrometry are provided. The analytical method comprises the steps of labeling the biomolecule, such as a glycan, in the sample by reacting with a compound of Formula V, VI, VII, VIII or IX or a compound of Table D for a time and under conditions suitable to facilitate the labeling through reductive amination; and subjecting the labeled conjugate to liquid chromatography and mass spectrometry.

Phenyl Based MS Active Fluorescence Tagging Compounds

Methods for tagging glycans can be accomplished by reductive amination of glycans with MS active, fluorescence tagging phenyl derivatives of Formula X:

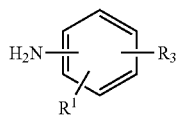

Formula X wherein
$R^1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^3$ is

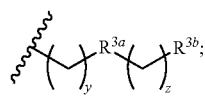

$R^{3a}$ is selected from ester, amide, amine, oxygen, urea, carbamate, carbonate, sulfur, thiourea, thiocarbamate alkyl or carbonyl;
$R^{3b}$ is

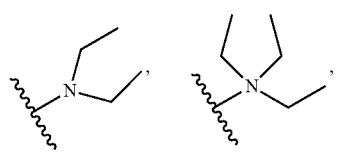

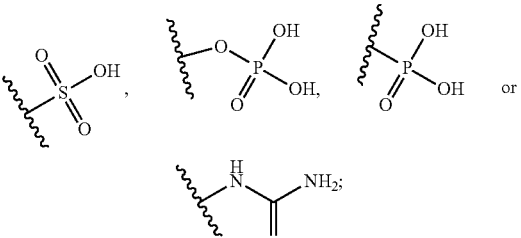

y=0-12;
z=1-12;
and salts or solvates thereof.

In yet another embodiment, methods for tagging biomolecules, such as glycans, with a compound of Formula XA is provided as follows:

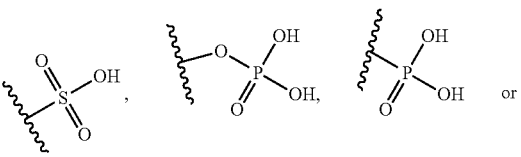

Formula XA wherein
$R^1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

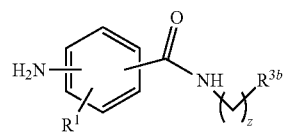

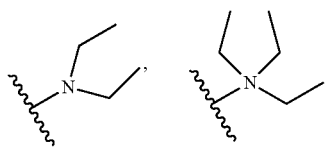

z=1-12;
and salts or solvates thereof.

In yet another embodiment, methods for tagging biomolecules, such as glycans, with a compound of Formula XB is provided as follows:

Formula XB

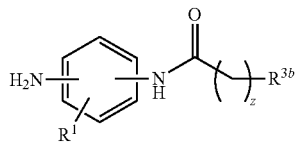

wherein
R[1] is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

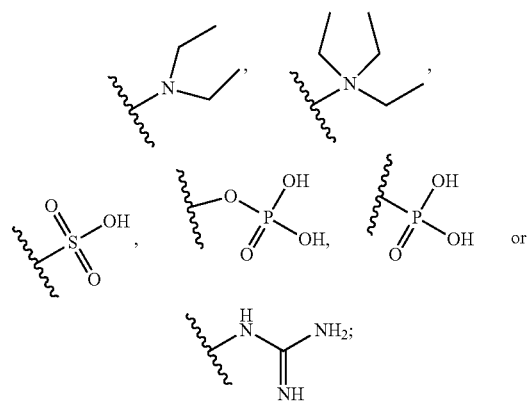

z=1-12;
and salts or solvates thereof.

In yet another embodiment, methods for tagging biomolecules, such as glycans, with a compound of Formula XC is provided as follows:

Formula XC

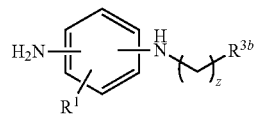

wherein
R[1] is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

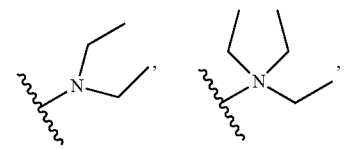

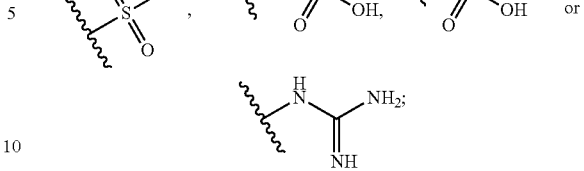

z=1-12;
and salts or solvates thereof.

In yet another embodiment, methods for tagging biomolecules, such as glycans, with a compound of Formula XD is provided as follows:

Formula XD wherein
R[1] is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

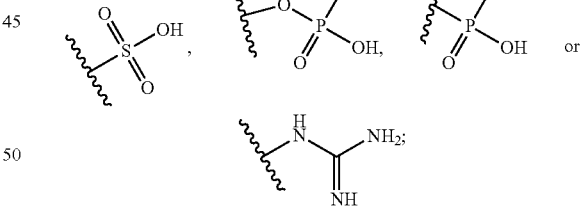

z=1-12;
and salts or solvates thereof.

In yet another embodiment, methods for tagging biomolecules, such as glycans, with a compound of Formula XE is provided as follows:

Formula XE

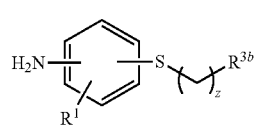

wherein
R¹ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

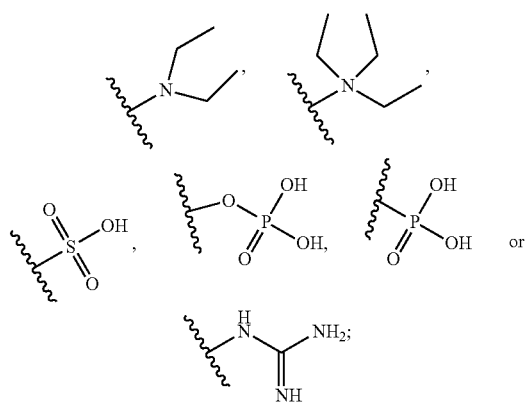

z=1-12;
and salts or solvates thereof.

In yet another embodiment, methods for tagging biomolecules, such as glycans, with a compound of Formula XF is provided as follows:

Formula XF

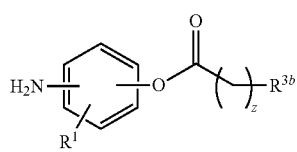

wherein
R¹ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

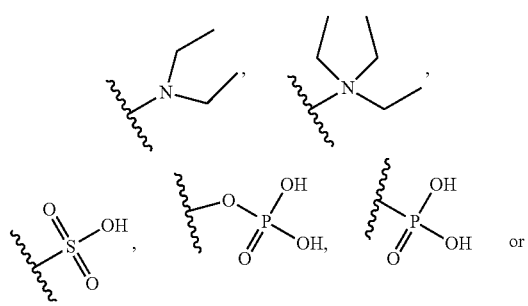

-continued

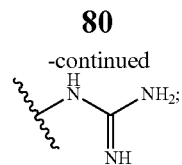

z=1-12;
and salts or solvates thereof.

In yet another embodiment, methods for tagging biomolecules, such as glycans, with a compound of Formula XG is provided as follows:

Formula XG

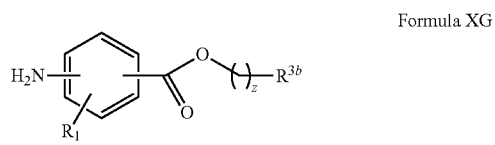

wherein
R¹ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

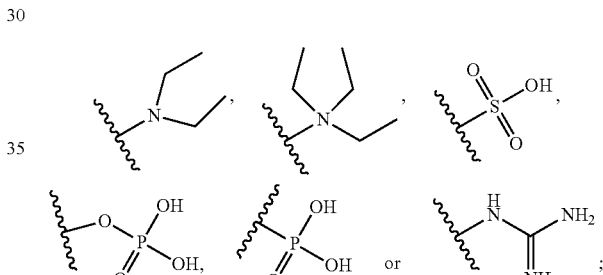

z=1-12;
and salts or solvates thereof.

In addition, provided below are exemplary compounds (Table E) of the structural Formulas X, XA, XB, XC, XD, XE, XF or XG which can be useful for fluorescent labeling of glycans and subsequent analysis by means of liquid chromatography and mass spectrometry. The compounds of structural Formulas X, XA, XB, XC, XD, XE, XF or XG could be optionally substituted with any group that does not substantially reduce the fluorescence of the compound.

In an embodiment, provided herein are compounds of X, XA, XB, XC, XD, XE, XF or XG wherein R¹ is hydrogen. In an embodiment, further provided are compounds of Formula X, XA, XB, XC, XD, XE, XF or XG wherein R² is hydrogen. In an embodiment, compounds of Formula X, XA, XB, XC, XD, XE, XF or XG include compounds wherein R¹ and R² are hydrogen.

TABLE E

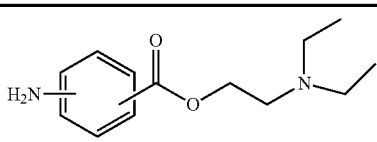

TABLE E-continued
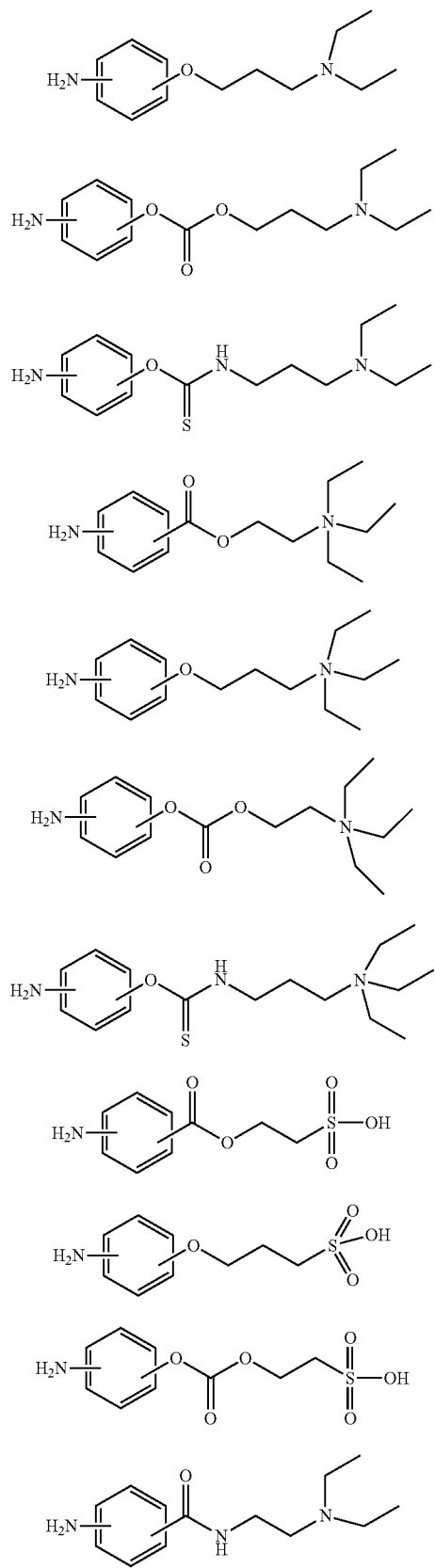
TABLE E-continued
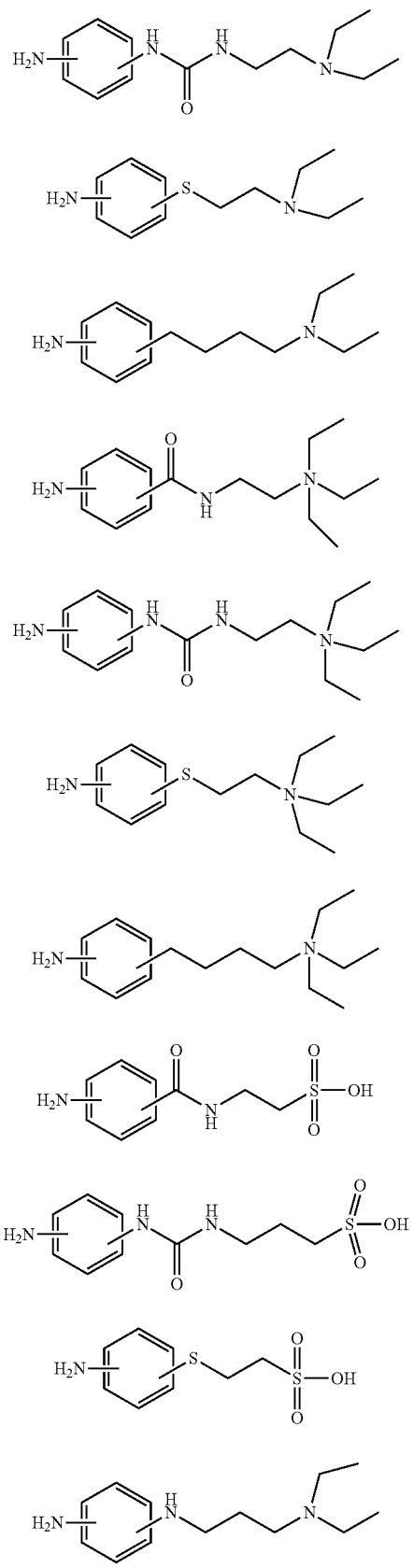

TABLE E-continued
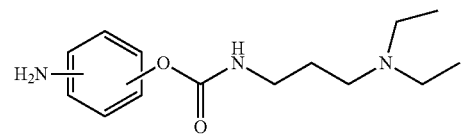
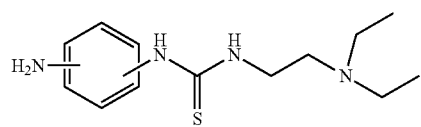
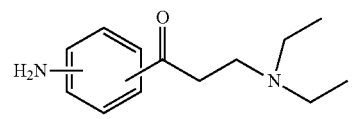
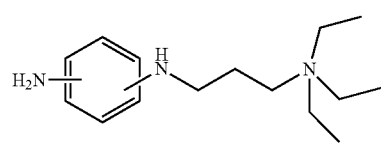
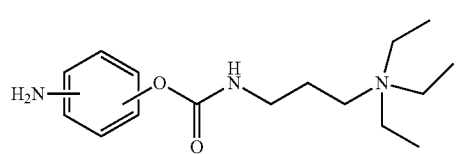
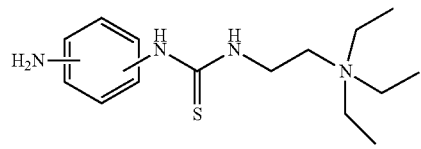
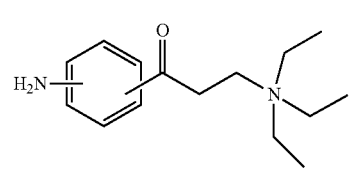
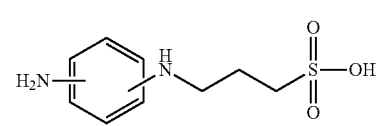
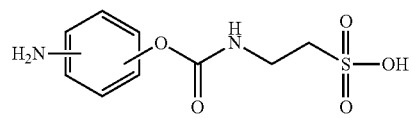
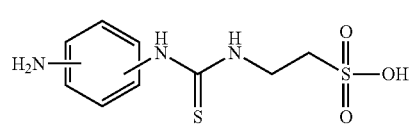
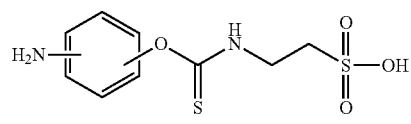
TABLE E-continued
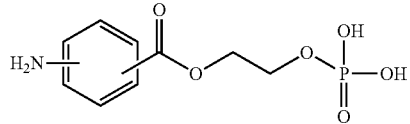
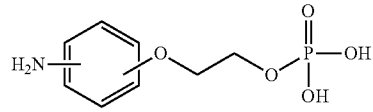
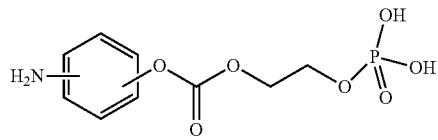
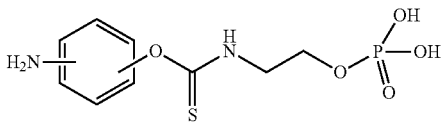
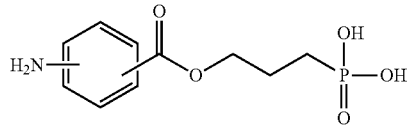
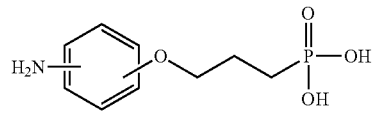
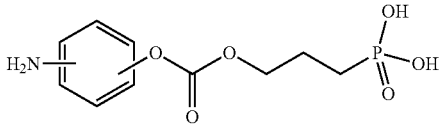
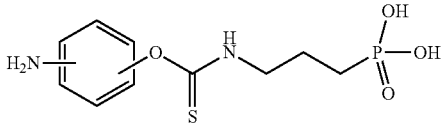
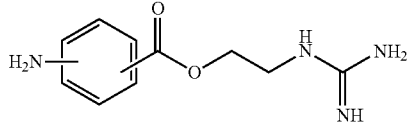
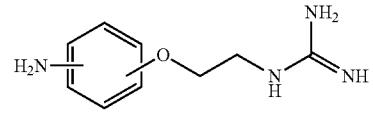
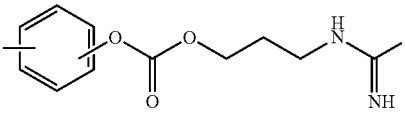

TABLE E-continued
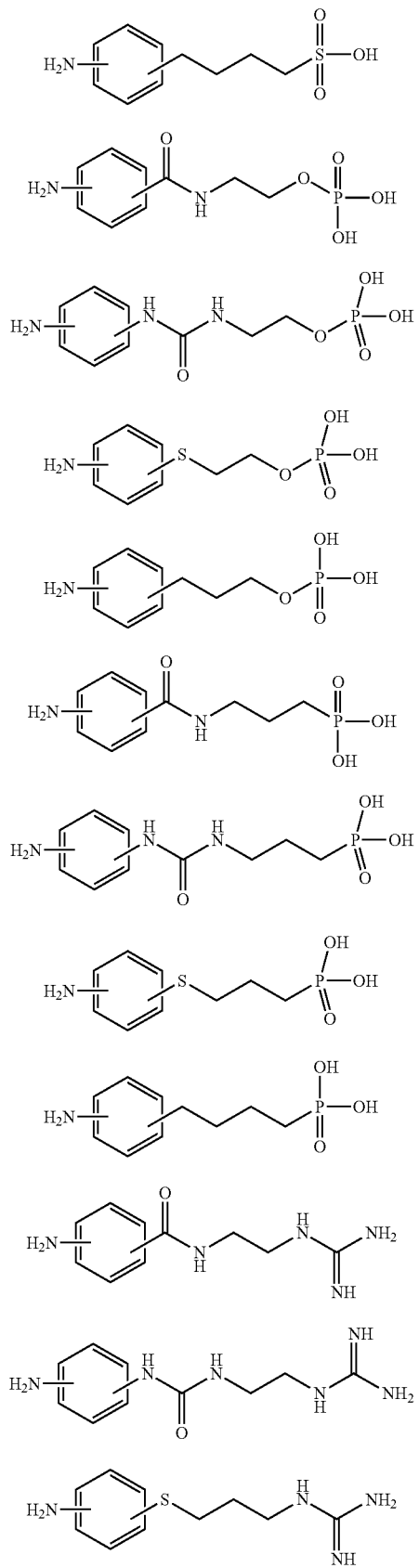
TABLE E-continued
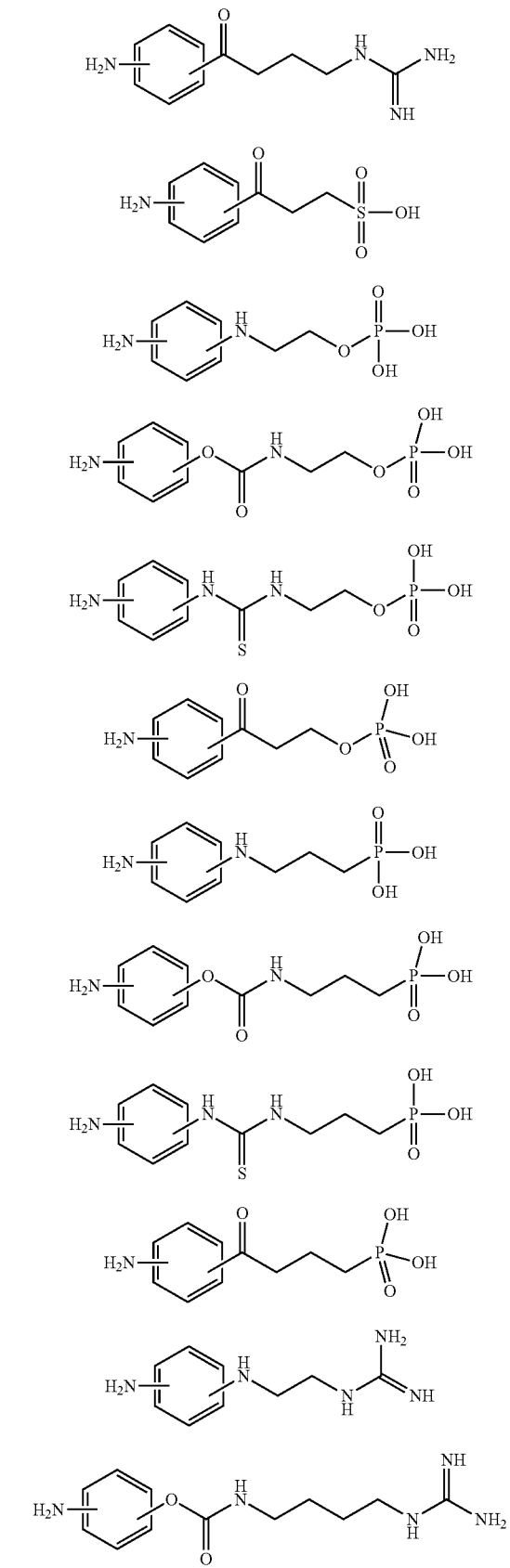

TABLE E-continued

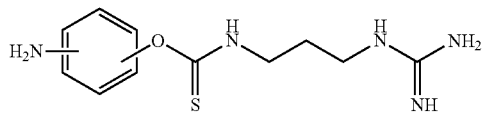

Methods for tagging, derivatizing or conjugating glycans and other biopolymers containing at least one ketone group or an aldehyde group with a compound of Formula X, XA, XB, XC, XD, XE, XF or XG or a compound of Table E by reductive amination reaction are further provided. The reaction between a compound of Formula X, XA, XB, XC, XD, XE, XF or XG and an aldehyde containing biopolymer, such as a glycan can be conducted under conditions that facilitate reductive amination in the presence of a reducing agent, such as from sodium cyanoborohydride or sodium triacetoxyborohydride. The reaction can be carried out in a solution or suspension of a compound of Formula X, XA, XB, XC, XD, XE, XF or XG or a compound of Table D in an acidic media, for example in citric acid or acetic acid, and by mixing with a solution or suspension of a reducing agent such as cyanoborohydride or sodium triacetoxyborohydride in an organic solvent, for example, tetrahydrofuran or dimethylsulfoxide.

Methods for analyzing a glycan and other biomolecules containing an aldehyde group in a sample by means of liquid chromatography and mass spectrometry are provided. These analytical methods include the step of labeling the biomolecule, such as a glycan, in the sample by reacting with a compound of Formula X, XA, XB, XC, XD, XE, XF or XG for a time and under conditions suitable to facilitate the labeling through reductive amination; and subjecting the labeled conjugate to liquid chromatography and mass spectrometry.

As provided herein, glycans can be conjugated to MS active fluorescent compounds of Formula X and salts or solvates thereof. The following general schematic shows the tagging of a glycan using a compound of Formula X through reductive amination:

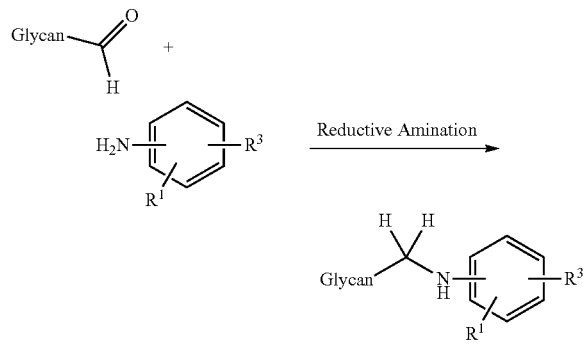

wherein FL $R^1$, $R^2$ and $R^3$ are as described above.

The process of reductive amination can be used to label aldehyde containing glycans and other biomolecules with compounds described herein. Further these compounds like other compounds presented in U.S. patent application Ser. No. 14/458,760 (published as US2014/0350263) and Ser. No. 15/005,619 (unpublished) might be used to rapidly label glycans under certain conditions.

Synthetic Methods

The following schemes I and II can be used to make the compounds described herein.

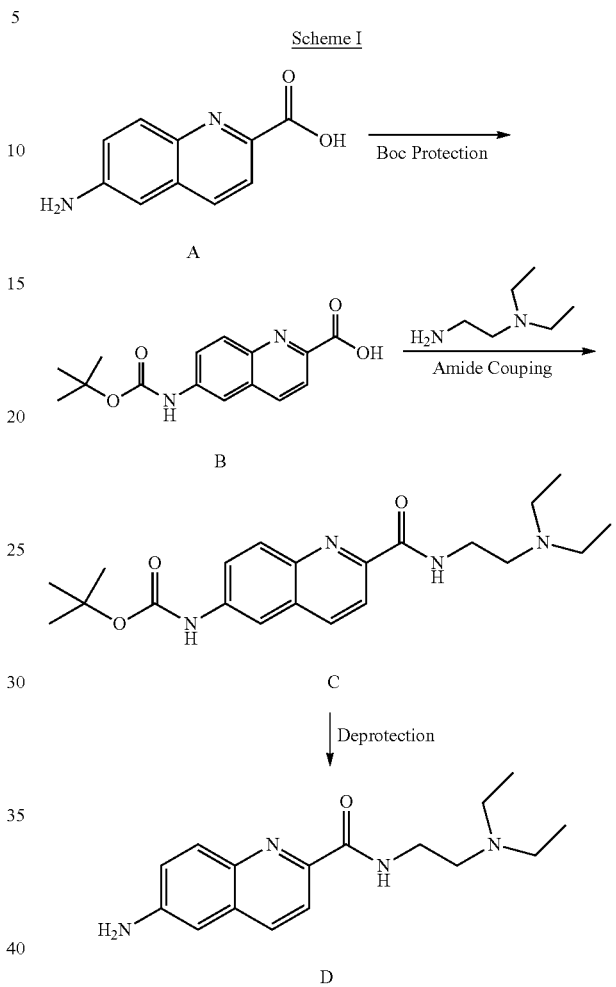

Preparation of 6-amino-N-[2-(diethylamino) ethyl]-2-quinolinecarboxamide (D)

40 mg of B was dissolved in 2.5 mL of a 1:4 mixture of dimethylformamide:dichloromethane in a 10 mL flask equipped with a stir bar and purged with $N_2$. 1.7 mg of dimethyl aminopyridine and 181 μL of dicyclohexylcarbodiimide were then added to the flask. After stirring for 10 min, 2-(diethylamino) ethylamine (57 mg) in 3 mL of dichloromethane was added to the flask. This was then stirred at room temperature for 20 hours. After this time, 3 mL of water was added to the reaction flask. The organic layer was separated and the aqueous layer was extracted with 2 mL of dichloromethane. The organic phases were combined, dried, and then evaporated to dryness to provide the crude material. This was subjected to standard organic chemistry purification techniques to provide the desired material C in >95% purity.

1.8 g of C was dissolved in a mixture of 5.3 g of trifluoroacetic acid in 30 mL of dichloromethane. The reaction mixture was stirred at room temperature for 48 hours. After removal of the solvent under reduced pressure, the crude material was dissolved in 30 mL of 0.5 N HCl. This mixture was then extracted with 50 mL aliquots of ethyl acetate. The organic phases were combined, dried, and then evaporated to dryness to yield 1.2 gram of the crude product. This was subjected to standard organic chemistry purification techniques to provide the desired material D in >98% purity.

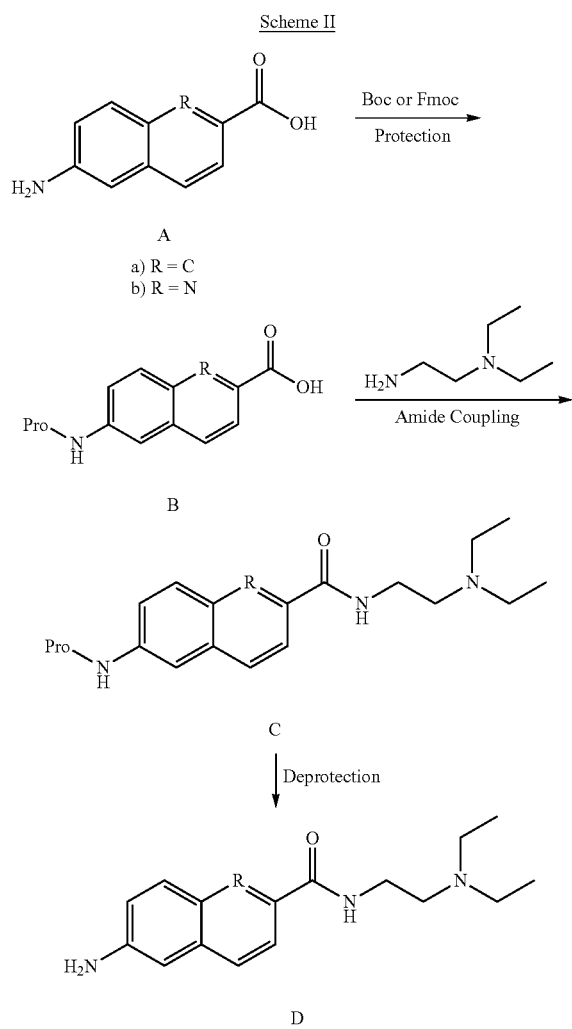

Scheme II a) R = C
b) R = N

The method used for Scheme I is applicable to Scheme II for making the compounds presented herein.

Other Derivatization Methods

A few alternative derivatization procedures have been developed to permit the assay of glycans by high performance liquid chromatographic and electrophoretic separations. Under certain conditions, the compounds presented herein can be subject to rapid tagging processes where reagent solution is added to released glycans at room temperature for four or five minutes, and then lyophilized and subsequently reconstituted in acetonitrile/water solution. Other possible derivatization methods that might be utilized to tag glycans with the reagents described herein include:

(1) The o-phthalaldehyde ("OPA")/mercaptan method. The OPA procedure can detect amino acids with a typical detectable level in the order of about 100 femtomole (fmol). Here, an adduct can be unstable and, therefore, should be prepared shortly before the detection step. Also, the reagent may not form a derivative with secondary amino acids.

(2) The 9-fluorenylmethylchloroformate ("FMOC") method. The FMOC procedure provides for stable derivatives having a minimum detectable level in the order of a few hundred fmol. Free tryptophan and cystine are sometimes difficult to quantitate. The derivatizing reagent is preferably removed from the reaction mixture by an extraction step because it is itself fluorescent. The reagent has also been reported to form multiple derivatives with histidine. The reagent can be hazardous to work with, because it is corrosive and is a lachrymator.

(3) The phenylisothiocyanate ("PITC") method. The PITC procedure yields stable derivatives which are formed rapidly. It can be used for both primary and secondary amino acids, as well as cysteine. The method uses absorbance as the detection procedure, and can provide a minimum detection limit of 1 pmol. However, the derivatives are not fluorescent and detection must be performed at 254 nm, which does not allow for good detection selectivity.

(4) The dansyl chloride method. The dansyl chloride method provides stable derivatives with a minimum detectability in the order of about 1.5 pmol. It is able to detect secondary amines and cysteine, but it results in multiple derivatives.

(5) Fluorescent succinimidocarbamates are useful as derivatizing agents for amines, amino acids, peptides, phosphates and other classes of compounds. When the succinimidocarbamate reagent is used to tag a compound with a fluorescent group, a detection limit of about 1 pmol can be achieved. These reagents can be used in conjunction with modern separation techniques such as high performance liquid chromatography, thin layer chromatography or capillary electrophoresis.

The present methods are not restricted to any specific linkage chemistry or attachment mechanism.

Detection of Derivatized Glycans by MS and Fluorescence

Most amino acids and/or glycans are not readily detectable in the absence of a strong chromophore or fluorophore or MS active moiety. The absorbance and fluorescence response are quite weak. One tactic used to maximize the sensitivity of an assay is to convert the compound of interest into a derivative that exhibits a better response for the detection method being utilized. The selection of a derivatizing agent is an important choice in the development of an analytical procedure. The derivatizing agent affects the ultimate sensitivity and accuracy of the analysis by maximizing the sensitivity, yield and stability of the derivatized molecules.

Basically, the following determinations can be performed separately: (1) the glycosylated sites; (2) the glycosylated site occupancy; (3) the structure and amount of each glycan at each site: and (4) the number of glycoforms. Harvey, D. J., *Identification of Protein-Bound Carbohydrates by Mass Spectrometry*, 1 PROTEOMICS 311-319 (2001) at 312, incorporated herein by reference. In most situations, MS can provide the answers to each of these steps. Hence the need for enhanced MS signals. Because of the branched nature of the glycan, however, structural determination of the glycan is complicated. Here, the monosaccharide unit, the anomericity and ring size of each monosaccharide, the monosaccharide sequence and ring conformation together with identification of other groups must be determined. With the exception of ring conformation, MS can be used directly or indirectly to make these determinations using MALDI and/or ESI as the preferred MS technique. Id. at 313-316, incorporated herein by reference.

Compounds described herein are useful for derivatizing glycans because they can form stable, highly fluorescent MS derivative compounds and conjugate glycans. The general methodology for an analysis of a glycan or amino acid derivatized by these compounds include three closely related processes: (1) formation of derivatives in the sample; (2) separation of the derivatives; and (3) detection of the separated derivatives. The first step is generally performed by reacting a mixture with one of the present compounds as a reagent to yield a derivatized compound. The derivatives provide a fluorescent signal which can then be detected in the detection stage of the analysis.

The separation step is based upon the differences in the chemical structure of the derivatives. The derivatized compounds can differ from each other in the same way that the chemical structures of the precursor compounds differ. The derivatives must be separated so that the detector signal can be correctly related to the concentration of each derivative. The derivatized glycans can be separated and detected by chromatography, e.g., by high performance liquid chromatography ("HPLC") or capillary zone electrophoresis ("CZE").

The detection step is generally carried out using either an absorbance or fluorescence detector. As each derivative is eluted from the chromatographic column after separation, its presence and quantity is detected by a mass spectrometer and/or by the absorbance or emission of light. The sensitivity of the assay depends upon the strength of the signal produced.

Analytical methods of analyzing glycans have become considerably sophisticated. Exemplary analytical instrumentation includes CE-, HPAEC-PAD, HILIC-LC/FLR, RPLC/MS, and MALDI-MS. Liquid chromatography ("LC") separation with fluorescence detection is frequently used in the pharmaceutical industry for the characterization of enzymatically/chemically released glycan, typically tagged with a fluorescent dye at the reducing end of a glycan. Kalyan R. Anumula & Shirish T. Dhume, *High Resolution and High Sensitivity Methods for Oligosaccharide Mapping and Characterization by Normal Phase High Performance Liquid Chromatography Following Derivatization with Highly Fluorescent Anthranilic Acid,* 8 GLYCOBIOLOGY 685 (1998); Karina Mariiio et al., *A Systematic Approach to Protein Glycosylation Analysis: A Path Through the Maze,* 6 NATURE CHEMICAL BIOLOGY 713 (2010).

Fluorescent measurements are sensitive and quantitative; the low detection limit is in the low femtomoles. With recent advancements in mass spectrometry instrumentation, the combination of liquid chromatography, fluorescence and MS has gained more popularity as an analytical instrument platform for routine characterization of fluorescently labeled N-linked glycans. Therefore, relative quantitation and molecular weight measurements can be done in a single analysis. Shigeo Suzuki et al., *Comparison of the Sensitivities of Various Derivatives of Oligosaccharides in LC/MS with Fast Atom Bombardment and Electrospray Ionization Interfaces,* 1006 ANAL CHEM 2073 (1996). However, a challenge has been that glycans do not ionize efficiently via electro-spray-ionization ("ESI").

Additional Uses for the Compounds Presented Herein

Absorbance detection is generally used in protein mapping work. Two different detection processes which are often used for this purpose are: a) detection at 210-215 nm using a single wavelength detector; and b) broadband spectral detection using a photodiode array (PDA) detector. In the first method, all peptides absorb at that wavelength, thus the user can ensure that all peptides eluted from the column are detected. One difficulty with this technique is that a wide variety of compounds absorb in this region of the spectrum, and extreme care must be taken to ensure that all reagents, eluents, glassware, etc. are scrupulously clean to ensure that the observed signal is solely from the peptides. In the second method, the PDA detector collects the spectra of the eluent at specific time intervals (e.g. a spectrum between 200 and 350 nm is collected every second). This provides more information than a single wavelength and thus can assist in distinguishing between peptides which can elute with similar retention times.

Sample Preparation

To obtain high quality mass spectra, the condition of the sample is important. Compounds other than analyte will generally have an adverse effect on ion yield and are preferably removed. Indeed, while small amounts of sodium are essential for ionization by MALDI, carbohydrates are particularly susceptible to the effects of salts. Moreover, many carbohydrates occur as mixtures. Therefore, it is important to ensure that isolation and purification techniques do not cause fractionation of the sample with a loss of quantitative information.

Reagents with Basicity and Hydrophobicity

In addition, we have discovered that the compounds described herein can enhance ionization efficiency of the reductively aminated saccharides, particularly O-linked glycans, when the tagged glycan is subsequently electrosprayed in positive ion mode to create protonated ions. This phenomenon can be attributed to two attributes of the reagent: its high gas phase basicity and hydrophobicity that produces non-polar surface area.

For example, a compound referred to herein as 6-ADEQ is shown structurally below.

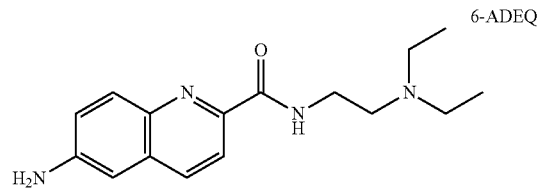 [SMILES: CCN(CC)CCNC(=O)c1ccc2cc(N)ccc2n1]

See, WO2013/049622 A1 at page 32. 6-ADEQ can be used to enhance the fluorescence and ionization efficiency of aldehyde containing molecules, such as saccharides or oligosaccharides. As described below, in comparison with oligosaccharides labeled with 2-aminobenzamide ("2-AB"),

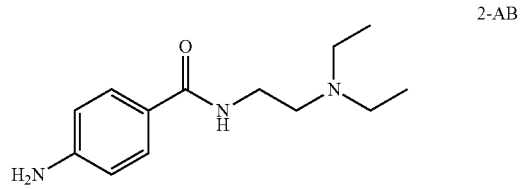 [SMILES: CCN(CC)CCNC(=O)c1ccc(N)cc1]

the 6-ADEQ labeled oligosaccharide has been found to yield six (6) times greater fluorescence signal and approximately 250 times greater positive ion mode MS signal when analyzed by hydrophilic interaction liquid chromatography. (Example 1, FIG. 2). The 6-ADEQ label has a unique ability to enhance the ionization efficiency of reductively aminated saccharides when they are electrosprayed in positive ion mode to create protonated ions. This can be attributed to two attributes of the 6-ADEQ label: its high gas phase basicity and its hydrophobicity.

While labeling compounds bearing high pKa, basic residues have previously been used for reductive amination of saccharides, previous studies showed procainamide to be most effective at improving MS response. See e.g., Klapoetke, S. et al., *The Evaluation of a Novel Approach for the Profiling and Identification of N-linked Glycan With a Procainamide Tag by HPLC With Fluorescent and Mass Spectrometric Detection.* J Pharm Biomed Anal, 53 (3), 315-24 (2010). While procainamide has a tertiary amine side chain that is identical to 6-ADEQ, it has a non-polar surface area of only 181 Å$^2$. The larger non-polar surface area of 207 Å$^2$ contributes to the ability of 6-ADEQ to more effectively increase MS response factors.

Analysis of glycans by ESI has been hampered by the hydrophilicity of the sugar functional groups that create a higher free energy of solvation and are more difficult to desorb from the electrospray droplet in the generation of gas-phase ions. See, Walker, H. S., et al., *Hydrophobic Derivatization of N-linked Glycans for Increased Ion Abundance in Electrospray Ionization Mass Spectrometry*, J. Am. Soc. Mass Spectrom. 22, 1039-1317 (2011) Imparting additional hydrophobic functions onto glycan molecules allows the glycans to be less solvated and have a higher surface activity in the precursor electrospray droplet. Id. As this droplet is desolvated, a series of Coulombic fission events occur where smaller droplets are ejected from the surface of the original droplet. Id. As reported, in comparison with native glycans, the more hydrophobic derivatized glycans are the more likely they will have higher surface activity and are then significantly enriched in the progeny droplets which further desolvated and eventually produce gas-phase ions.

Hence, to increase the ion abundance of analytes in mass spectrometry, the present methods combine the benefits of non-polar surface area with a pKa greater than 7 to provide enhanced MS signaling. In an embodiment, the pKa is between about 7 to 10 or between about 10 to 13. The non-polar surface areas of these labeling compounds are, at a minimum, 10% greater than procainamide as shown and described herein.

Positive Ion Versus Negative Ion Mode

The reagents described herein can enhance positive ion mode MS analyses of peptides and/or glycopeptides. In the present methods, amine residues are modified by the introduction of a tag (label) having high non-polar surface area combined with a high pKA basic residue. As shown in Example IV below, this combination improves the ionization of peptides during positive ion mode MS analyses. Peptides are routinely separated by chromatography under acidic conditions where acidic groups present on a peptide or glycopeptide (aspartic and glutamic amino acids and the groups of monosaccharides known as sialic acids) are protonated. The peptide or glycopeptide once modified adopts higher charge states because of the enhanced basicity.

Conversely, certain reagents have been designed to alter the basicity of a peptide or glycopeptide. For example, in one method, a sulfonate anion is added to the fluorescent group for detection in UHPLC and to improve the sensitivity of matrix-assisted laser desorption/ionization ("MALDI") measurements made in the negative ion mode. Hendel, J. H., et al., *A Fluorescent Labeling and Enrichment System for Glycopeptides Generated from Proteolytic Digestion of IgG mAbs; A System That Can Be Used as Part of the Peptide Mapping Workflow*, USP Workshop on Glycosylation Analysis for Biopharmaceuticals, Rockville, Md., August 25-26; Rockville, Md., 2015. With this type of modification targeted to amine residues, the reagent is designed to convert the N-terminus or the side chains of lysine residues into an acidic functionality containing the label that is linked to the peptide through a neutral urea bond to improve the analysis sensitivity in the negative ion mode of MALDI. The change in chemical properties of the reagent, however, can compromise an analytical technique for peptides in measured in the positive ion mode MS.

Analyses of peptides and glycopeptides by MALDI are different than the LC/MS analysis. MALDI is a soft ionization technique used in mass spectrometry, allowing the analysis of biomolecules (biopolymers such as DNA, proteins, peptides/glycopeptides, and glycans) and large organic molecules including polymers, dendrimers, and other macromolecules which tend to be fragile and fragment when ionized by more conventional ionization methods. MALDI is similar in character to electrospray ionization ("ESI") in that both techniques are relatively soft ways of obtaining intact ions of large molecules in the gas phase, though MALDI produces far fewer multiple charged ions.

MALDI methodologies are typically a three-step processes. First, the sample is mixed with a suitable matrix material and applied to a metal plate. Second, a pulsed laser irradiates the sample, triggering ablation and desorption of the sample and matrix material. Finally, analyte molecules are ionized by being protonated or deprotonated in the hot plume of ablated gases, and can then be accelerated into a mass analyzer.

On the other hand, LC-MS analysis is an analytical chemistry technique that combines the physical separation capabilities of liquid chromatography and the mass analysis capabilities of mass spectrometry ("MS"). LC-MS is a powerful technique that has a very high measurement sensitivity, making it useful in many applications. Its application is oriented towards the separation, general detection, and potential identification of analytes having a specific mass in the presence of other compounds (i.e., in complex mixtures), e.g., natural products from natural-products extracts and pure substances from mixtures of chemical intermediates. Preparative LC-MS systems can be used for rapid mass-directed purification of specific substances from such mixtures that are important in basic research, and pharmaceutical, agrochemical, food, and other industries. Like gas chromatography-mass spectrometry, it allows analysis and detection even of minute amounts of a substance.

Figure 10:
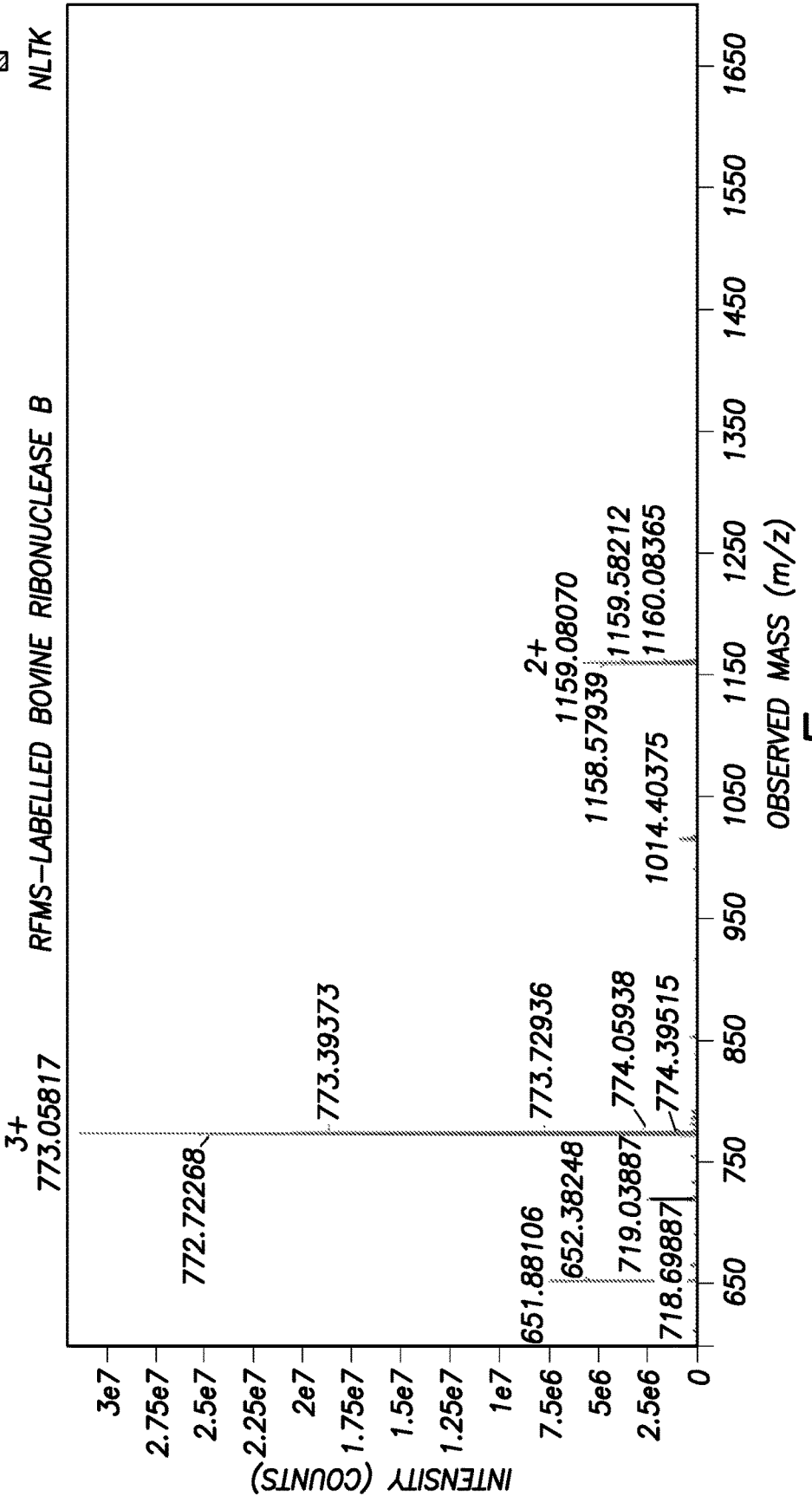
FIG. 10 shows an ESI mass spectrum of a derivatized bovine ribonuclease B tryptic glycopeptide tagged with a compound presented herein where generated ions were 2+ and 3+.
Figure 12:
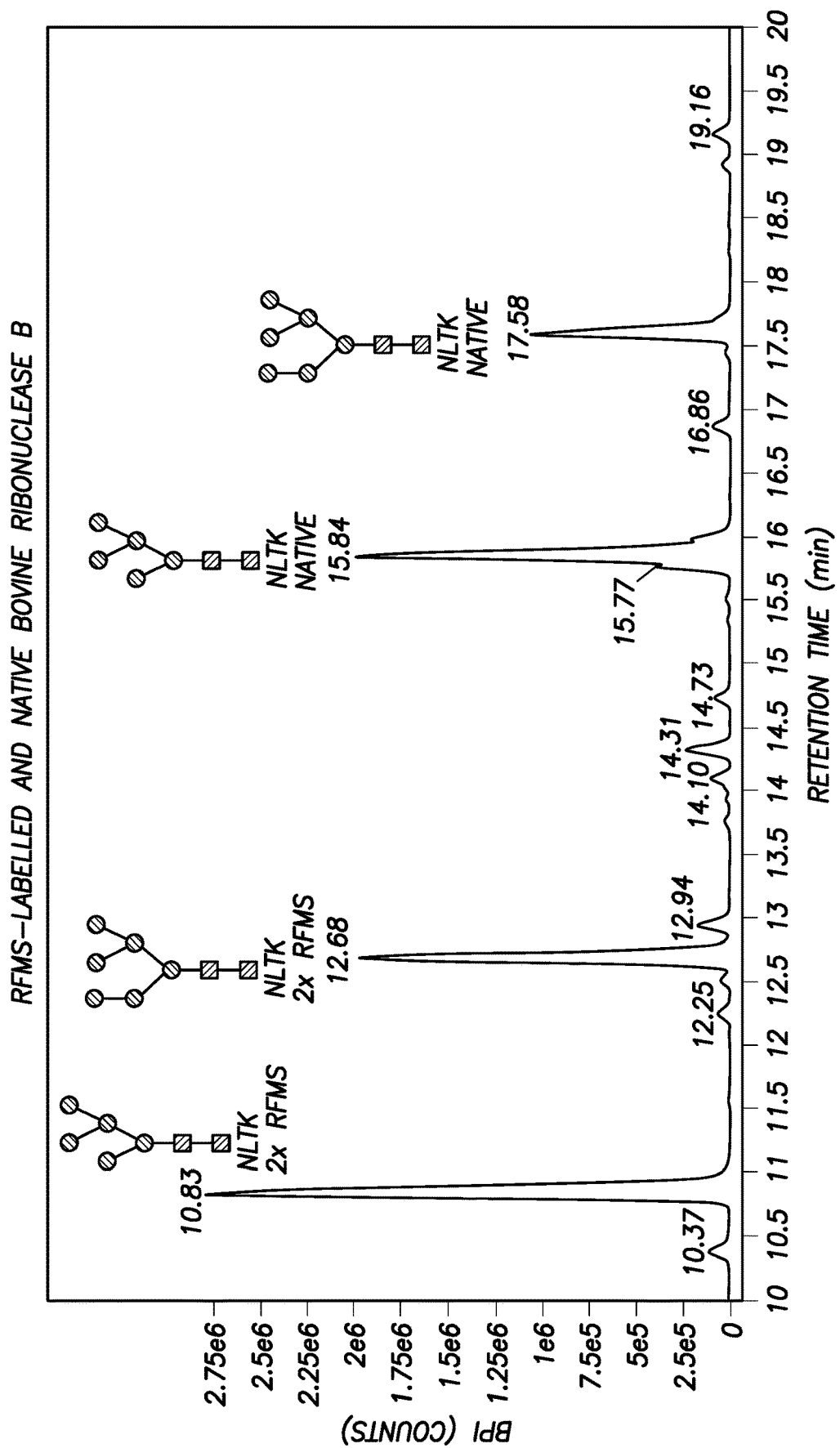
FIG. 12 provides a comparison of the ESI extracted ion chromatograms for two RFMS-labelled and native bovine ribonuclease B tryptic glycopeptides where ESI of the RFMS-labelled bovine ribonuclease B tryptic glycopeptides generated more intense ion signals than the native bovine ribonuclease B tryptic glycopeptides.
Figure 13:
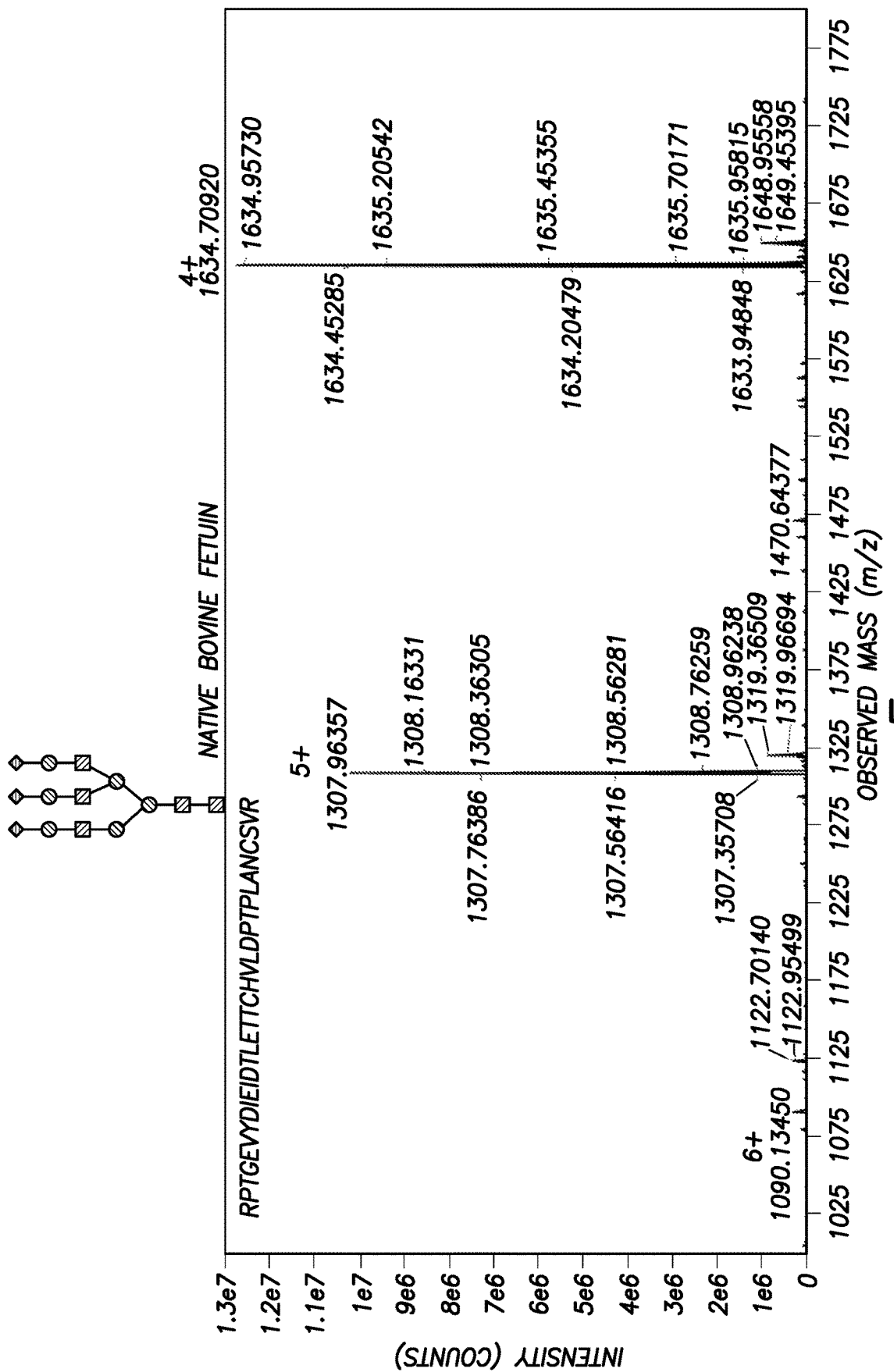
FIG. 13 shows an ESI mass spectrum of a native tryptic glycopeptide from bovine fetuin presented herein where generated ions were 4+, 5+, and 6+.
Figure 14:
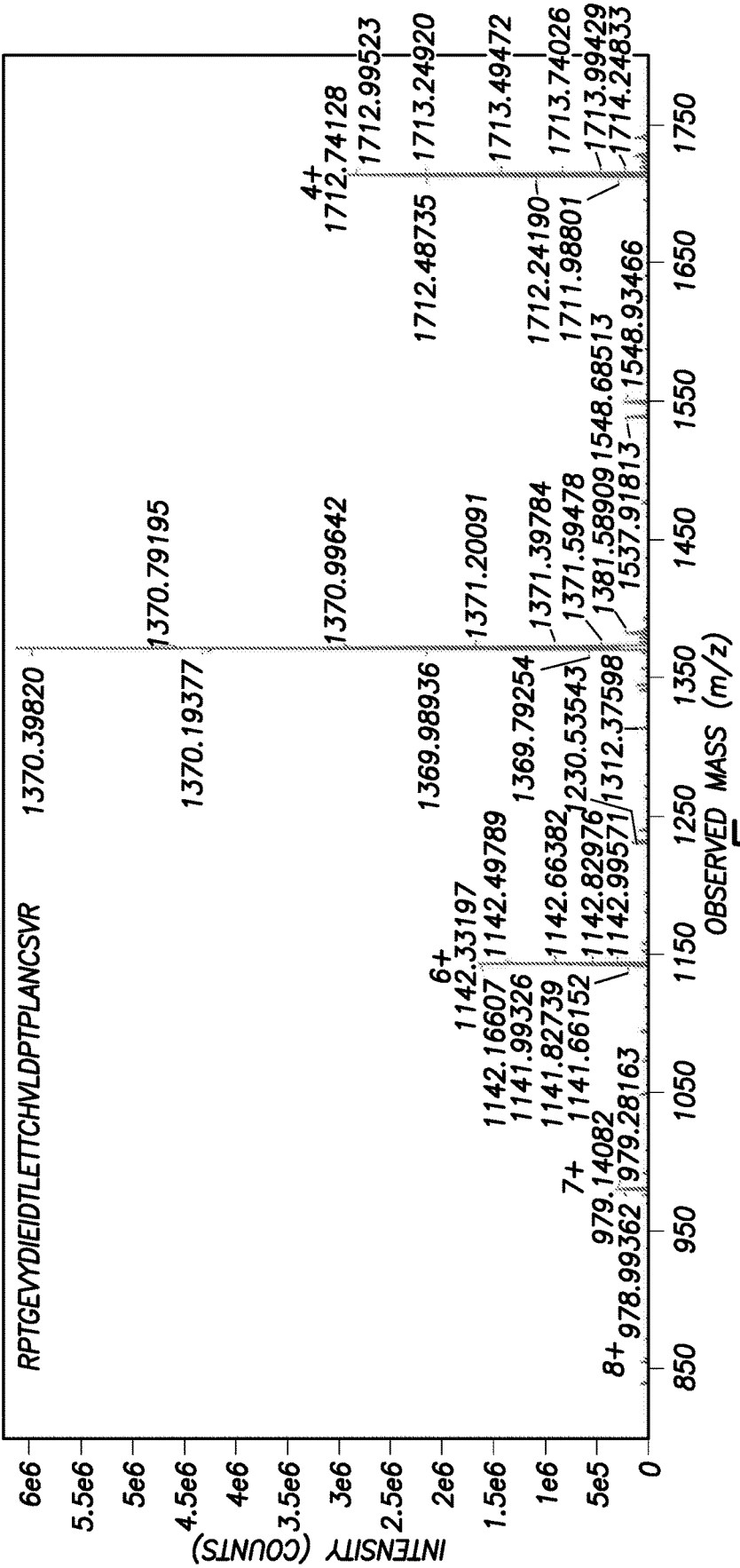
FIG. 14 shows an ESI mass spectrum a derivatized bovine fetuin tryptic glycopeptide tagged with a compound provided herein and ESI generated large amounts of 4+ and 5+ ions as well as 6+, 7+ and 8+ ions.

In addition to the increased measurement sensitivity in positive ion mode MS for tags described herein, another important change to the MS results was observed. This was the ability of this tag to generate highly charged ESI ions. For example, as shown in FIGS. 10 and 12, ESI generated nonderivatized glycopeptide derived from bovine ribonuclease B generated at 2+ ion while the same glycopeptide following labeling produced at 3+ ion. Similarly, as shown in FIGS. 13 and 14, ESI generated underivatized glycopeptide from bovine fetuin produced 4+ and 5+ ions. The tagged analogue produced significantly higher amounts of the 4+ ion as well as 6+ and 7+ ions. The 6+ and 7+ were only observed for the derivatized glycopeptide.

The ability of the tag to generate more highly charged ions has favorable implications for tandem MS (or "MSMS") analyses, particularly, electron transfer dissociation ("ETD"). ETD is a complementary technique to collision-induced dissociation ("CID") and is often used to fragment peptides that carry labile modifications, such as glycopeptides. However, ETD is limited to an effective mass-to-charge range (m/z). Coon, J. J., *Collisions or Electrons? Protein Sequence Analysis in the 21st Century*, Anal Chem 2009; 81: 3208-3215. Many underivatized glycopeptides will have ions that fall outside of this rage. However, the ability of the tags described herein to generate more highly charged ions shifts the m/z values of glycopeptides within the effective window for ETD.

The analysis of peptides with negatively-charged tags requires special conditions for their analysis. High pH conditions should be used during their separations and such methods are not yet as robust as the low pH conditions used for hydrophilic interaction chromatography ("HILIC") of glycopeptides and reversed-phase columns used in the separation of peptides.

Additionally, CID of negatively charged ions generally produces abundant levels of neutral losses and internal fragments which are difficult to interpret. Brinkworth, C. S., et al., *Negative Ion Fragmentations of Deprotonated Peptides: Backbone Cleavages Directed Through Both Asp and Glu*, Rapid Communications in Mass Spectrometry 2001; 15: 1965-1973; See also, Steinborner, S. T., et al., *The Negative Ion Mass Spectra of [M-H]– Ions Derived From Caeridin and Dynastin Peptides, Internal Backbone Cleavages Directed Through Asp and Asn Residues*, Rapid Communications in Mass Spectrometry 1997; 11: 253-258. The ETD of negative ions has been demonstrated but is still far from a routine technique. Riley, N. M., et al., *The Negative Mode Proteome with Activated Ion Negative Electron Transfer Dissociation (AI-NETD)*, Mol Cell Proteomics 2015; 14: 2644-2660.

Example I

Mannose 5 (Man5) oligosaccharide was reductively aminated in high yield with either one of two different reagents, 2-aminobenzamide ("2-AB") and 6-ADEQ (FIG. 1). The resulting labeled mannose 5 species were then separated at equivalent mass loads using hydrophilic interaction liquid chromatography ("HILIC") and subsequently detected by fluorescence and electrospray ionization ("ESI") mass spectrometry ("MS").

A procedure for reductive amination was adapted from Szabo et al to prepare 6-ADEQ labeled Man 5 oligosaccharide. Szabo et. al., *Improved Sample Preparation Method for Glycan Analysis of Glycoproteins by CE-LIF and CE-MS*, ELECTROPHORESIS 31, 1389 (2010). For this labeling reaction, 800 pmol of dried Man 5 was reconstituted in 10 µL of 350 mM 6-ADEQ in 1.2M citric acid. Into this solution, 10 µL of 1M sodium cyanoborohydride in tetrahydrofuran was subsequently mixed. The resulting mixture was incubated at 55° C. After 1 hour, the reaction was quenched via addition of 120 µL water.

2-AB labeled Man 5 was prepared using a similar reductive amination procedure, specifically a protocol adapted from work by Bigge et al. *Nonselective and Efficient Fluorescent Labeling of Glycans Using 2-Amino Benzamide and Anthranilic Acid*, Anal Biochem, 230(2), 229 (1995). For this labeling reaction, 800 pmol of dried Man 5 was reconstituted in 20 µL of 350 mM 2-AB and 1M sodium cyanoborohydride in 30:70 acetic acid/dimethylsulfoxide. The resulting mixture was incubated at 55° C. After three hours, the reaction was quenched via addition of 120 µL water.

To benchmark the sensitivity gains afforded by 6-ADEQ, the above-mentioned Man 5 oligosaccharides were analyzed by HILIC chromatography with an ACQUITY UPLC Glycan BEH Amide column. As they eluted from the column, the different labeled forms of Man 5 were serially detected by fluorescence and ESI-MS per the experimental conditions listed below.

| LC CONDITIONS | |
|---|---|
| Column | Waters ACQUITY UPLC Glycan BEH Amide 130 Å 1.7 µm 2.1 × 50 mm |
| Mobile Phase A | 50 mM Ammonium Formate Buffer, pH 4.4 |
| Mobile Phase B | Acetonitrile |
| Column Temperature | 60° C. |
| Injection Volume | 1 µL |
| Sample Concentration | 6 pmol/µL |
| Fluorescence | 6-ADEQ Labeled - Ex 370 nm/Em 480 nm (5 Hz) |
| Detection | 2-AB Labeled - Ex 330 nm/Em 420 nm (5 Hz) |

| Gradient Table | | | | |
|---|---|---|---|---|
| Time(min) | Flow Rate(mL/min) | % A | % B | Curve |
| Initial | 0.500 | 20.0 | 80.0 | Initial |
| 16.00 | 0.500 | 45.0 | 55.0 | 6 |
| 16.30 | 0.500 | 100.0 | 0.0 | 6 |
| 17.30 | 0.500 | 100.0 | 0.0 | 6 |
| 17.60 | 0.500 | 20.0 | 80.0 | 6 |
| 20.00 | 0.500 | 100.0 | 0.0 | 6 |

| MS Conditions | |
|---|---|
| Polarity | ES+ |
| Acquisition: | 500-2000 m/z (1 Hz) |
| Capillary (kV) | 2.5 |
| Source Temperature (° C.) | 120 |
| Sampling Cone | 70 |
| Source Offset | 50 |
| Desolvation Temperature (° C.) | 350 |
| Desolvation Gas Flow (L/Hr) | 500 |
| Nebulizer Gas Flow (Bar) | 6.0 |

Data corresponding to this comparison example are portrayed in FIG. 2.

As such, methods for tagging a glycan or another biopolymer for enhanced mass spectroscopy signal and fluorescence comprising the steps of providing a glycan or another biopolymer containing an aldehyde group and reacting the glycan or biopolymer with an amphipathic compound having a non-polar surface area of more than about 200 Å$^2$ and having a primary amine group under conditions that can facilitate reductive amination wherein a conjugate of said amphipathic compound and said glycan is formed. In an embodiment, the non-polar surface area is between about 200 Å$^2$ and about 1000 Å$^2$ or between about 200 Å$^2$ and about 600 Å$^2$ or between about 200 Å$^2$ and about 500 Å$^2$ or between about 200 Å$^2$ and about 500 Å$^2$.

We further propose the use of reagents, such as RapiFluor-MS, that can be used to prepare labeled glycosylamines for hydrophilic interaction chromatography in as little as 30 minutes. Lauber, M. A.; Yu, Y. Q.; Brousmiche, D. W.; Hua, Z.; Koza, S. M.; Magnelli, P.; Guthrie, E.; Taron, C. H.; Fountain, K. J., *Rapid Preparation of Released N-Glycans for HILIC Analysis Using a Labeling Reagent that Facilitates Sensitive Fluorescence and ESI-MS Detection*, Anal Chem 87 (10), 5401-9 (2015). While facilitating fast preparations, RapiFluor-MS also yields inordinate gains in mass spectrometric (MS) sensitivity when glycans are analyzed by positive ion mode electrospray ionization mass spectrometry (ESI+MS).

Figure 5:
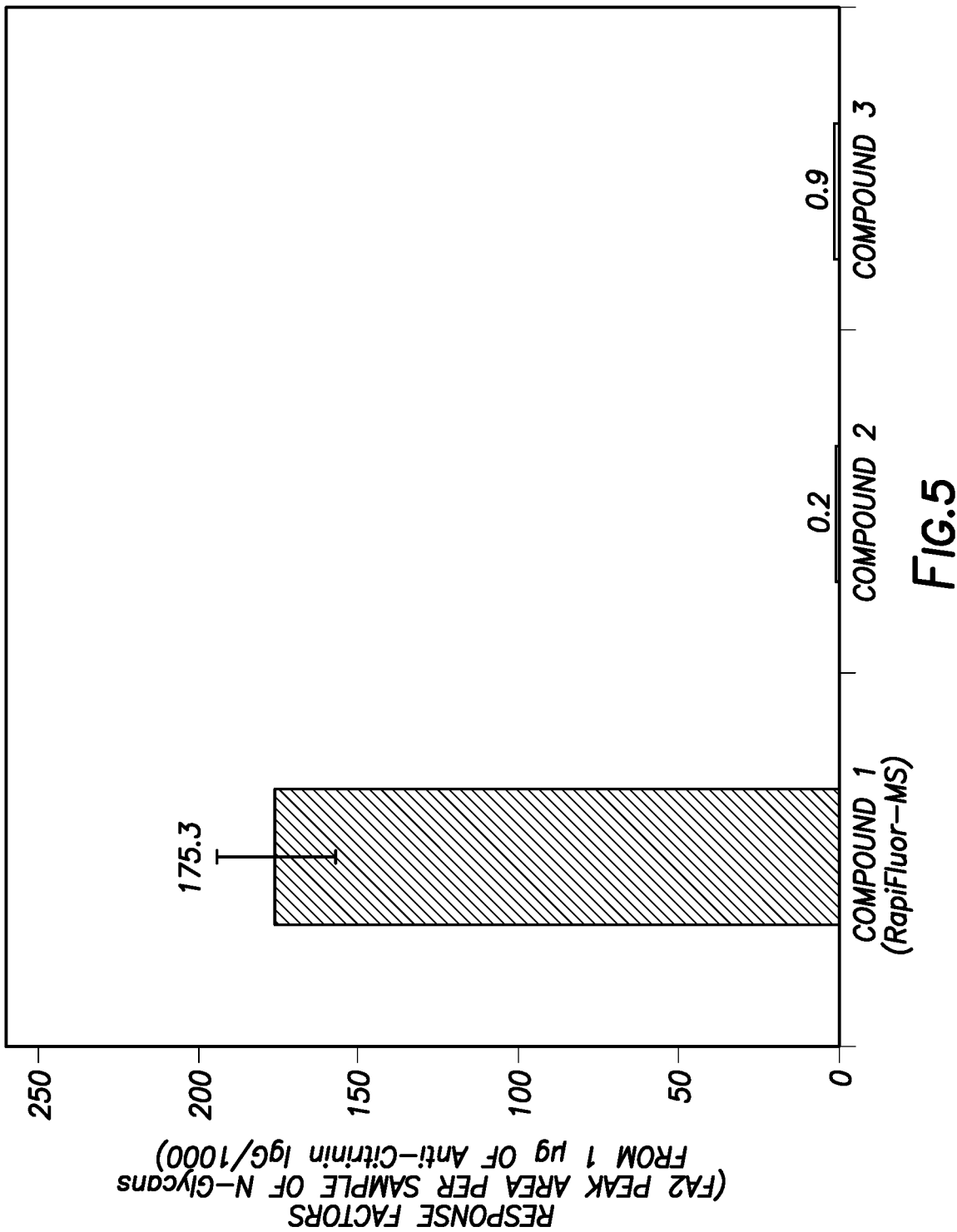
FIG. 5 shows a comparison of MS response factors as obtained for an FA2 Glycan Labeled with Compounds 1, 4, and 5 of FIG. 3 using an Ion Mobility Capable QT of Mass Spectrometer (Waters Synapt G2-S, Milford, Mass.).
Figure 6A:
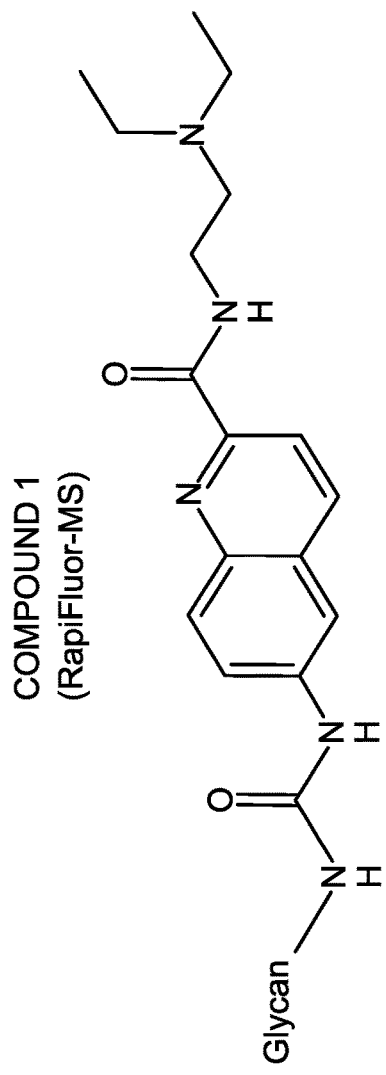
FIG. 6 shows a comparison of HILIC-MS base peak intensity chromatograms obtained for N-glycans labeled with compounds 1, 4, and 5 of FIG. 3 using a QT of Mass Spectrometer (Waters Xevo G2-XS, Milford, Mass.). N-glycans from 0.1 μg of anti-citrinin IgG1 monoclonal antibody were analyzed in each analysis.
Figure 6A:
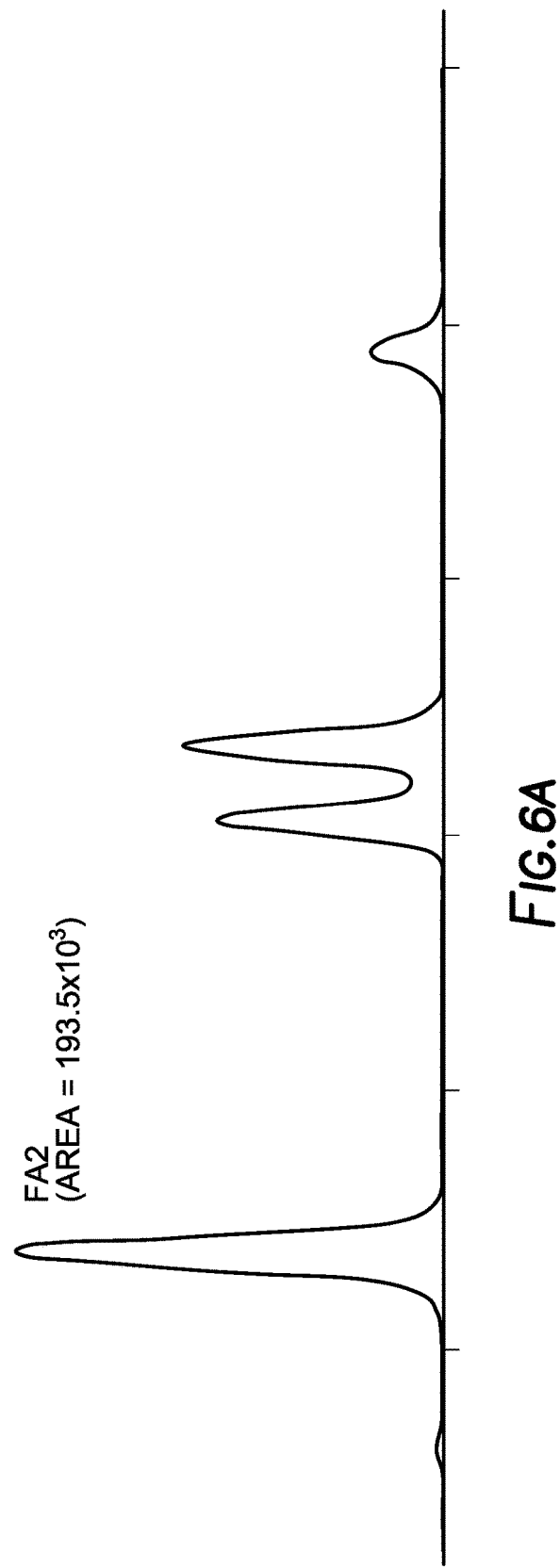
Figure 6B:
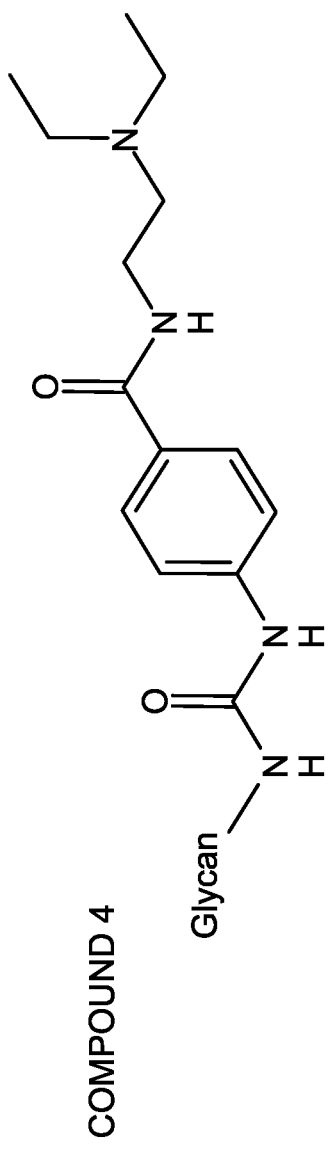
Figure 6B:
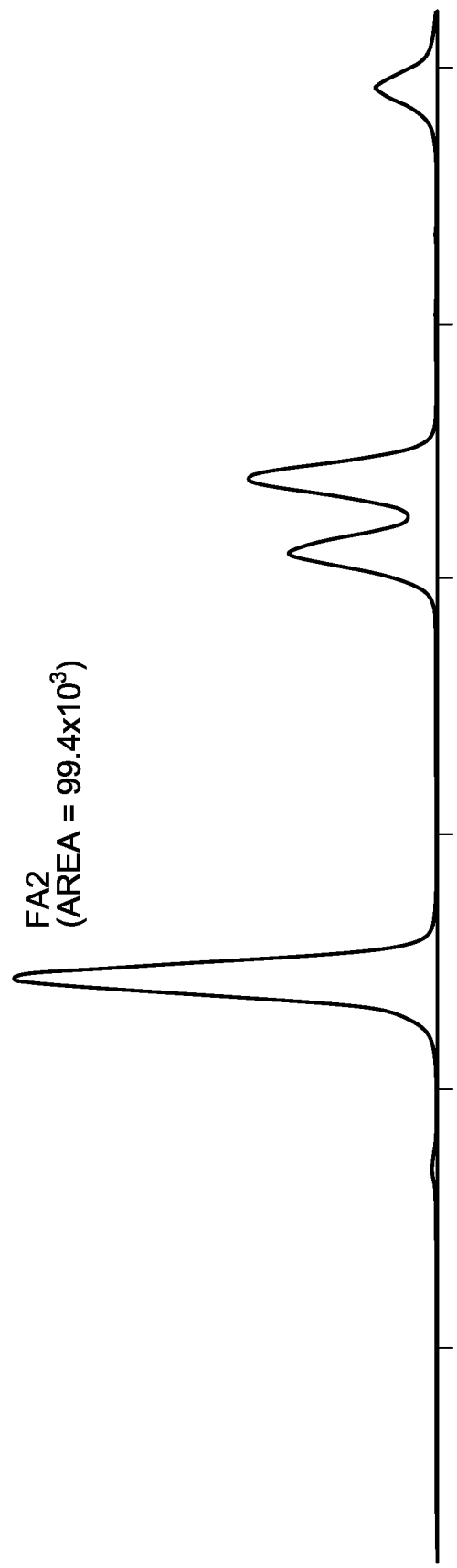
Figure 6C:
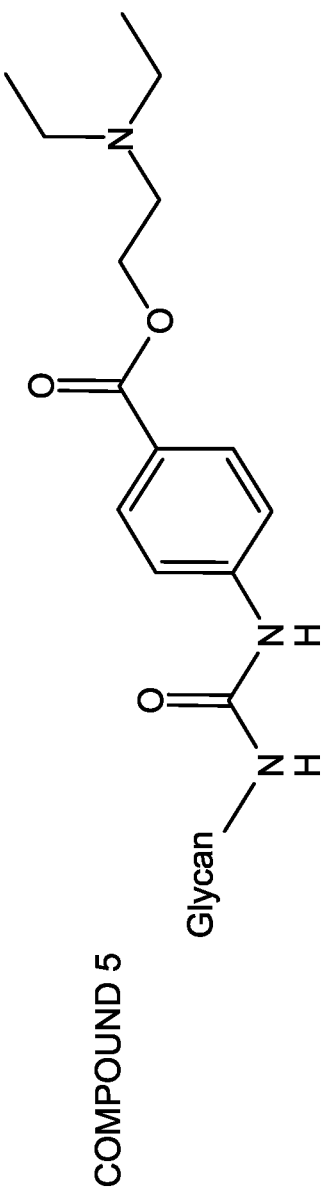
Figure 6C:
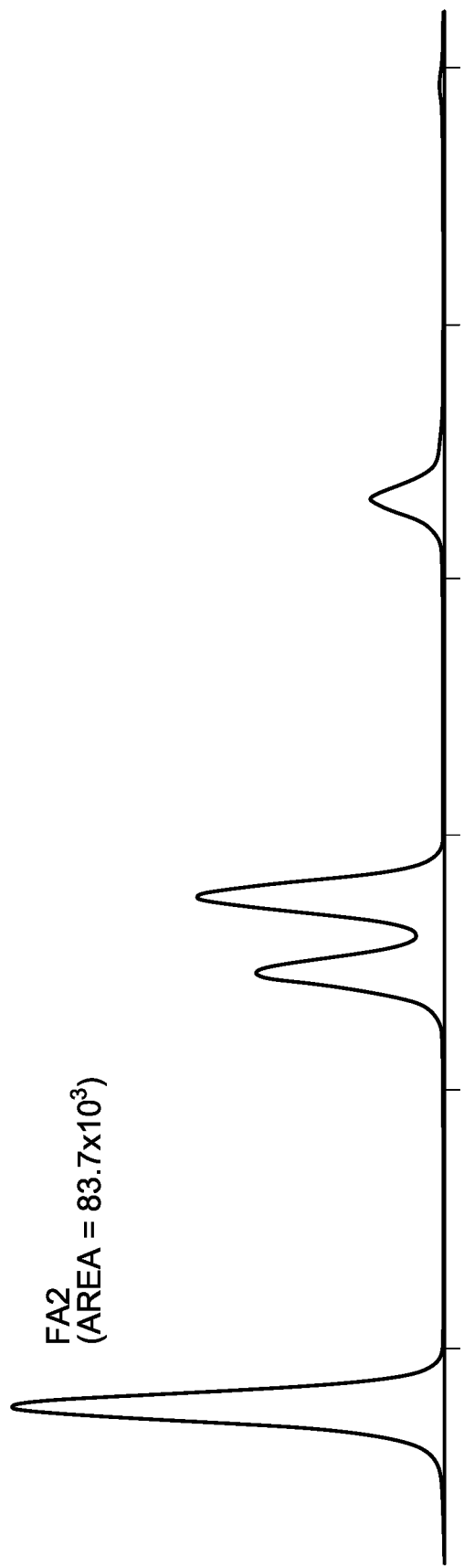
Figure 7:
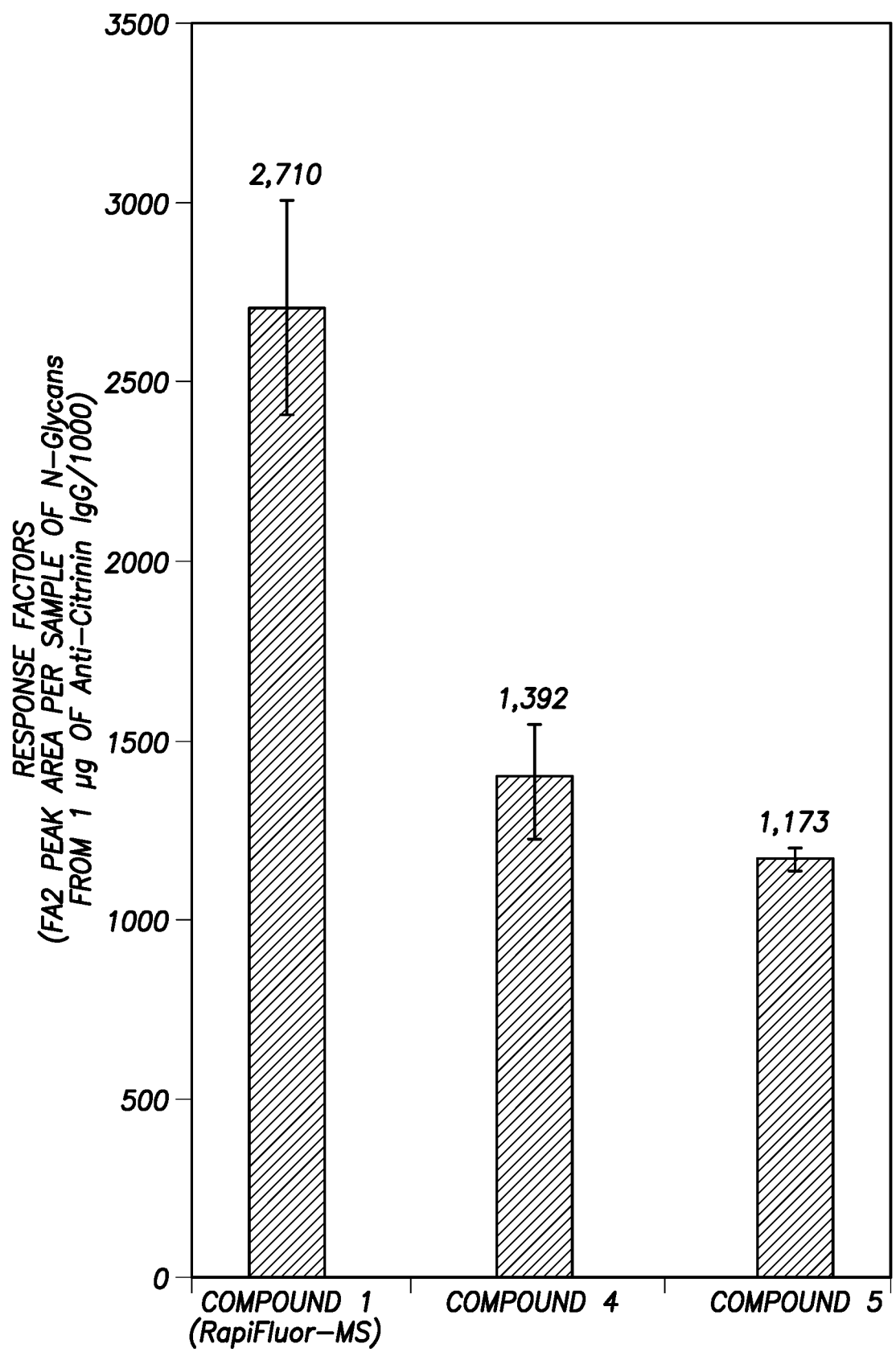
FIG. 7 shows a comparison of MS response factors as obtained for an FA2 Glycan Labeled with Compounds 1, 4, and 5 of FIG. 3 using a QT of Mass Spectrometer (Waters Xevo G2-XS, Milford, Mass.).
Figure 8A:
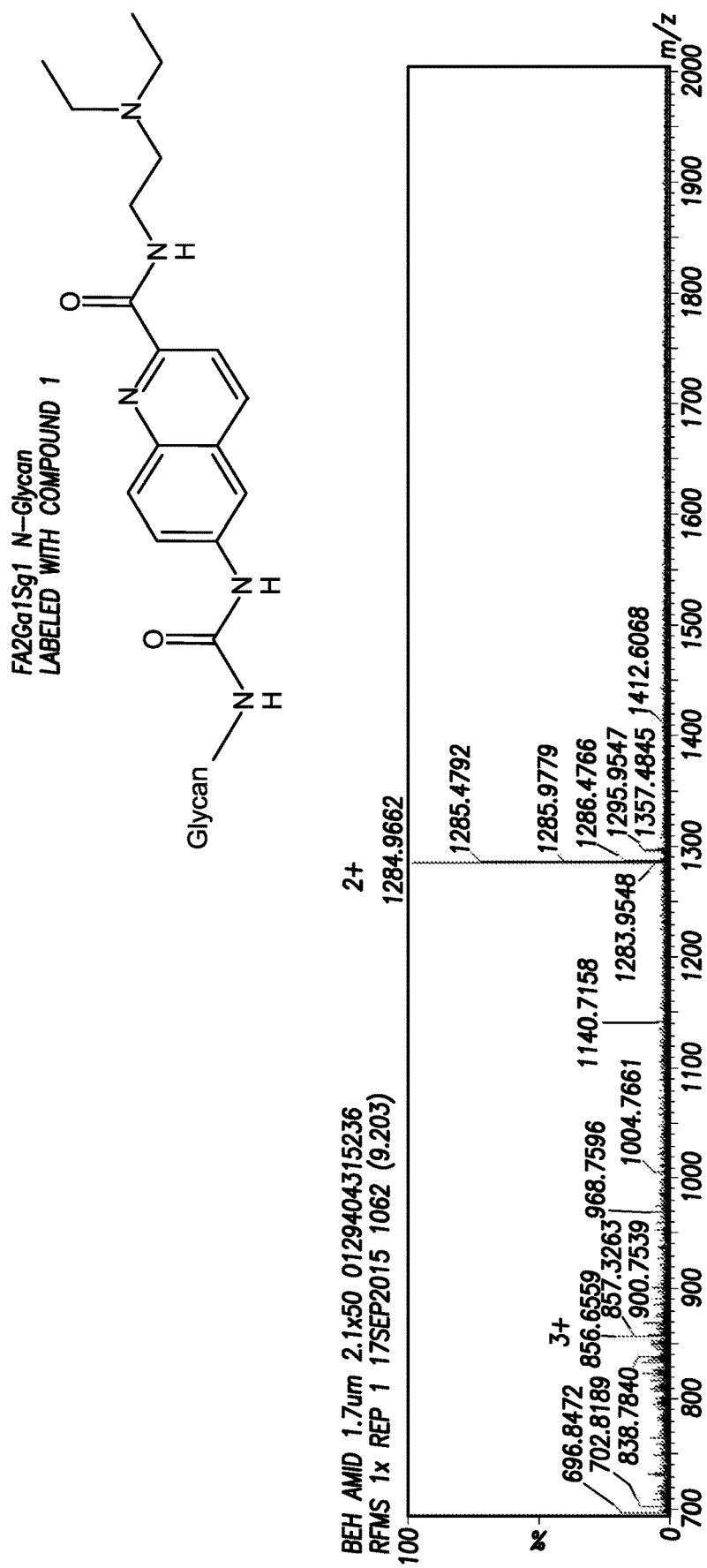
FIG. 8 shows a comparison of Mass Spectra obtained for a FA2Ga1Sg1 N-Glycan Labeled with Compounds 1, 4, and 5 of FIG. 3 using a QT of Mass Spectrometer (Waters Xevo G2-XS, Milford, Mass.).
Figure 8B:
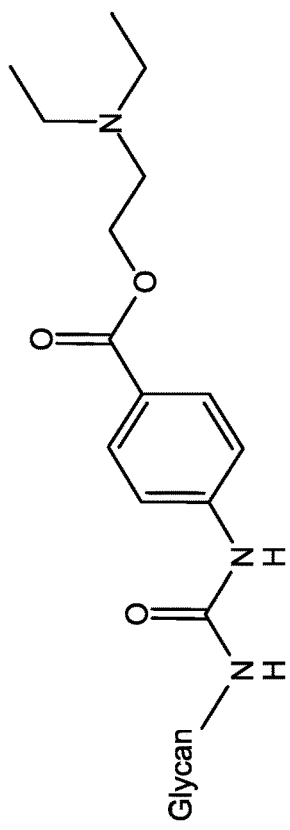
Figure 8B:
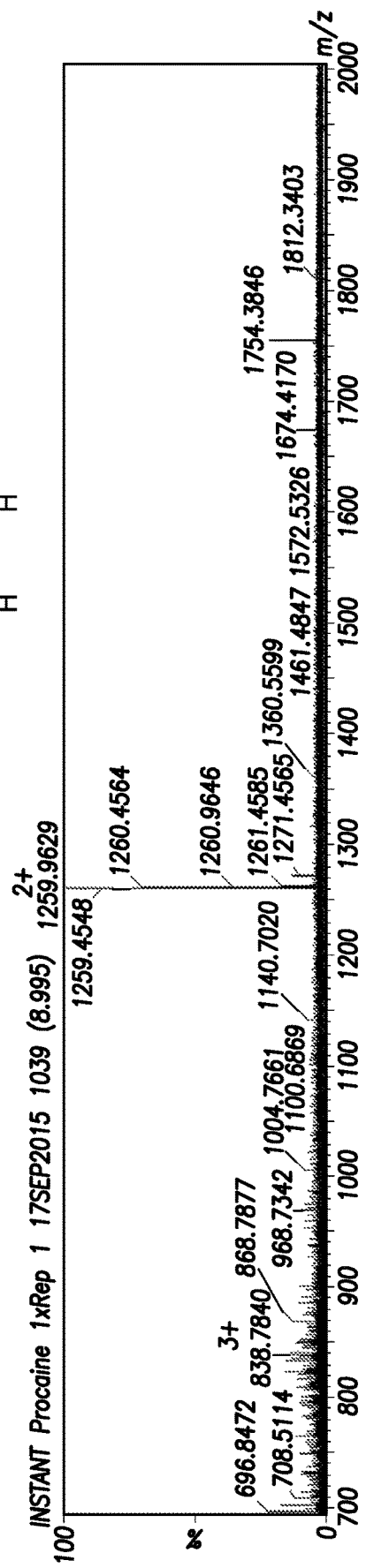
Figure 8C:
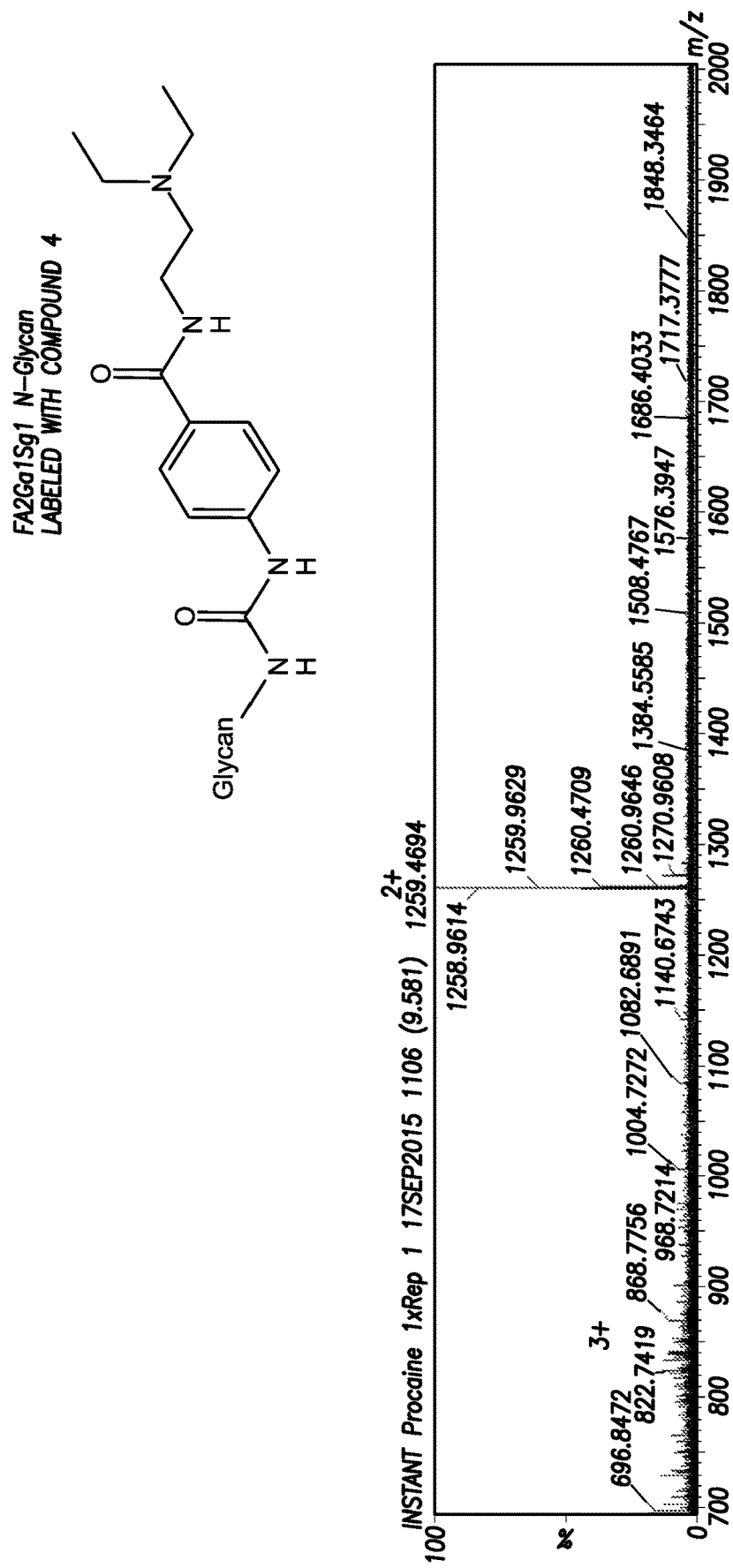

The mass spectrometric (MS) response factors of RapiFluor-MS labeled glycans have been benchmarked against other rapid tagging, glycosylamine reagents and their corresponding label moieties, including those that produce benzamide, quinoline, procainamide and procaine derivatives (FIG. 3). The results of these experiments show that the RapiFluor-MS label (from Compound 1) gives a ~600× increase in MS response versus a benzamide label (from Compound 2) and a ~200× increase in MS response versus a quinoline label (from Compound 3) (FIG. 4 and FIG. 5). Moreover, it has also been observed that the RapiFluor-MS label gives a ~2× increase in MS response versus procainamide and procaine-based labels (from Compounds 4 and 5, respectively) (FIG. 6 and FIG. 7). Additionally, it has been observed that RapiFluor-MS labeled glycans adopt comparatively higher average charge states (FIG. 8).

The RapiFluor-MS reagent incorporates an amphipathic label onto glycans that concomitantly increases their hydrophobicity and basicity. As has now been discovered, these characteristics define a unique type of labeled glycan structure that exhibits unprecedented gas phase proton affinity. Importantly, this methodology is not restricted to any one linkage chemistry and can be achieved with various rapid tagging glycosylamine labeling reagents. See e.g., U.S. patent application Ser. No. 14/458,760 (published as US2014/0350263) at [0008]-[0022], [0054]-[182] and [0191] and Ser. No. 15/005,619 (unpublished), incorporated by reference. Instead, this methodology encompasses two chemical aspects that can be imparted by a rapid tagging glycosylamine reagent: hydrophobicity and basicity. Two exemplary formula of rapid tagging glycosylamine labeling reagents include:

Formula XI

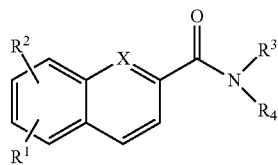

wherein
X=C or N;
$R^1$ is O=C=N— or

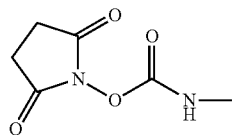

$R^2$ is independently selected from —H, —$C_1$-$C_8$ alkyl, —$C_1$-$C_8$ cycloalkyl, halo, dialkylamino, $CH_2$-dialkylamino, aminocarbonyl, alkoxycarbonyl, or alkoxy, but not Cl or O=C=N—; and $R^3$ and $R^4$ are independently selected from —H, alkyl, alkyl amino, alkylsulfonic acid, alkyl phosphonic acid, wherein either $R^3$ or $R^4$ is alkylamino, alkyl phosphonic acid, or alkylsulfonic acid.

Formula XII

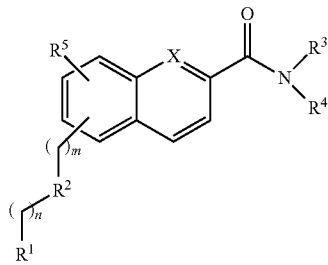

wherein
m=0-9;
n=0-9;
X=C or N
$R^1$ is O=C=N—, S=C=N—, or

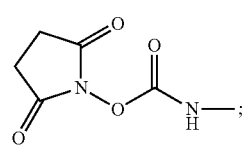

$R^2$ is independently selected from methylene, substituted nitrogen, oxygen, carbonyl, amide, ester, sulfur, sulfoxide, or sulfone;

$R^3$ and $R^4$ are independently selected from —H, alkyl, alkyl amino, alkylsulfonic acid, alkyl phosphonic acid, wherein either $R^3$ or $R^4$ is alkylamino, alkyl phosphonic acid, or alkylsulfonic acid; and $R^5$ is independently selected from —H, —$C_1$-$C_8$ alkyl, —$C_1$-$C_8$ cycloalkyl, halo, dialkylamino, $CH_2$-dialkylamino, aminocarbonyl, alkoxycarbonyl, or alkoxy, but not Cl when $R^1$ is O=C=N—, and when $R^1$ is S=C=N, $R^5$ is H.

Out of the previously described labels, the RapiFluor-MS label is unique in that it combines a high pKa ionizable group with a large non-polar surface area (FIG. 9). Not surprisingly, the RapiFluor-MS label exhibits the highest non-polar surface area, as is consistent with it also exhibiting the highest ESI+MS response factors.

Therefore, the present methods use a rapid tagging glycosylamine reagent that yields a labeling moiety having both a high pKa (>7) ionizable group and a functionality that affords a comparatively large non-polar surface area. Such rapid tagging glycosylamines reagents are taught in U.S. patent application Ser. No. 14/458,760 (published as US2014/0350263) at [0008]-[0022], [0054]-[182] and [0191] and Ser. No. 15/005,619 (unpublished), incorporated by reference. The non-polar surface areas of these label moieties are, at a minimum, 10% greater than an analogous procainamide-based label.

Example II

The response factors of N-glycans (glycosylamines) labeled with Compounds 1, 2 and 3 were evaluated via HILIC separations obtained with a UHPLC chromatograph (ACQUITY UPLC H-Class Bio, Waters, Milford, Mass.). Labeled glycans from 0.4 µg glycoprotein were separated using a 2.1×50 mm column packed with 1.7 µm amide bonded organosilica (130 Å) stationary phase (ACQUITY UPLC Glycan BEH Amide 130 Å, Waters, Milford, Mass.) along with an aqueous mobile phase comprised of 50 mM ammonium formate (pH 4.4) and another of ACN. Samples were injected as 1 µL aqueous volumes and separated at 60° C. with a flow rate of 0.4 mL/min and a 35-minute gradient going from 25 to 46% aqueous mobile phase. Eluting glycans were detected by positive ion mode electrospray ionization mass spectrometry using an ion mobility capable QT of mass spectrometer (Synapt G2-S, Waters, Milford, Mass.) operating with a capillary voltage of 3.0 kV, source temperature of 120° C., desolvation temperature of 350° C., and sample cone voltage of 80 V. Mass spectra were acquired at a rate of 1 Hz with a resolution of approximately 20,000 over a range of 500-2500 m/z.

FIG. 4 shows the HILIC-MS base peak intensity chromatograms for N-glycans from anti-citrinin murine IgG1 as labeled with Compounds 1, 2, and 3, respectively. MS (base peak intensity) response factors were calculated from these analyses and are shown in FIG. 5.

Example III

The response factors of N-glycans (glycosylamines) labeled with Compounds 1, 4 and 5 were evaluated via HILIC separations obtained with a UHPLC chromatograph (ACQUITY UPLC H-Class Bio, Waters, Milford, Mass.). Labeled glycans from 0.1 µg glycoprotein were separated using a 2.1×50 mm column packed with 1.7 µm amide bonded organosilica (130 Å) stationary phase (ACQUITY UPLC Glycan BEH Amide 130 Å, Waters, Milford, Mass.) along with an aqueous mobile phase comprised of 50 mM ammonium formate (pH 4.4) and another of ACN. Samples were injected as 0.2 µL aqueous volumes and separated at 60° C. with a flow rate of 0.4 mL/min and a 35-minute gradient going from 25 to 46% aqueous mobile phase. Eluting glycans were detected by positive ion mode electrospray ionization mass spectrometry using a QT of mass spectrometer (Xevo G2-XS QT of, Waters, Milford, Mass.) operating with a capillary voltage of 2.2 kV, source temperature of 120° C., desolvation temperature of 450° C., and sample cone voltage of 75 V. Mass spectra were acquired at a rate of 2 Hz with a resolution of approximately 40,000 over a range of 500-2500 m/z.

FIG. 6 shows the HILIC-MS base peak intensity chromatograms for N-glycans from anti-citrinin murine IgG1 as labeled with Compounds 1, 4, and 5, respectively. MS (base peak intensity) response factors were calculated from these analyses and are shown in FIG. 7.

Example IV

Glycopeptide Mapping of Ribonuclease B

The analysis of glycopeptides provides a wealth of data, including site-specific glycan information. However, glycans are difficult to characterize by routine LC-MS/MS approaches. Their collision-induced dissociation patterns show extensive glycan fragmentation, while the peptide backbone is unaffected. This can be useful for determining the glycan's composition, but hinders a definitive answer regarding its amino acid sequence. However, electron-transfer dissociation can be used for glycopeptide backbone fragmentation, when derivatized to allow higher charge states to be generated shifting their m/z values towards the effective region for ETD. Here, we utilized a rapid tagging molecule developed to improve fluorescent (FLR) and mass spectrometry (MS) performance for glycans, that when used to derivatize glycopeptides shows increased charge states and frequently, enhanced MS detection.

Methods

Glycoproteins were resuspended at 5 µg/µL in phosphate-buffered saline containing 0.1% Rapigest surfactant and 10 mM TCEP. Proteins were denatured at 60° C. for 1 hour ("hr.") and alkylated for 1 hr. with 25 mM iodoacetamide. Trypsin was added at 1:20 ratio and the proteins were digested for 18 hrs. The derivatization reagent was solubilized in DFM at 100 mg/mL and a 6.5-µL aliquot was added to a 5-µL aliquot of the digest (diluted with 20 µL of 100 mM, pH 8 phosphate buffer and 6.5 µL of DMF). After 5 minutes, a second 6.5 µL aliquot of the reagent was added. After quenching the reaction with TRIS, the samples were analyzed by optimized hydrophilic interaction liquid chromatography (HILIC)/UPLC-MS.

Preliminary Data

A successful LC-MS glycopeptide characterization requires optimization of HILILC mobile-phase conditions and derivatization to enhance their ESI-generated charge states. HILIC separation of glycopeptides requires the use of TFA, frequently at 0.1% (v/v) so that the separation is driven more by the glycans than the peptide backbone, therefore, the TFA spiked mobile phase in HILIC mode separates glycopeptide glycoforms more efficiently than reversed phase chromatography. However, including TFA as a modifier leads to decreased MS responses and generates ions with lower charges. The minimum amount of TFA required should be used and the optimized mobile phase conditions were determined to be 0.01% TFA/0.1% formic acid (v/v).

Figure 11:
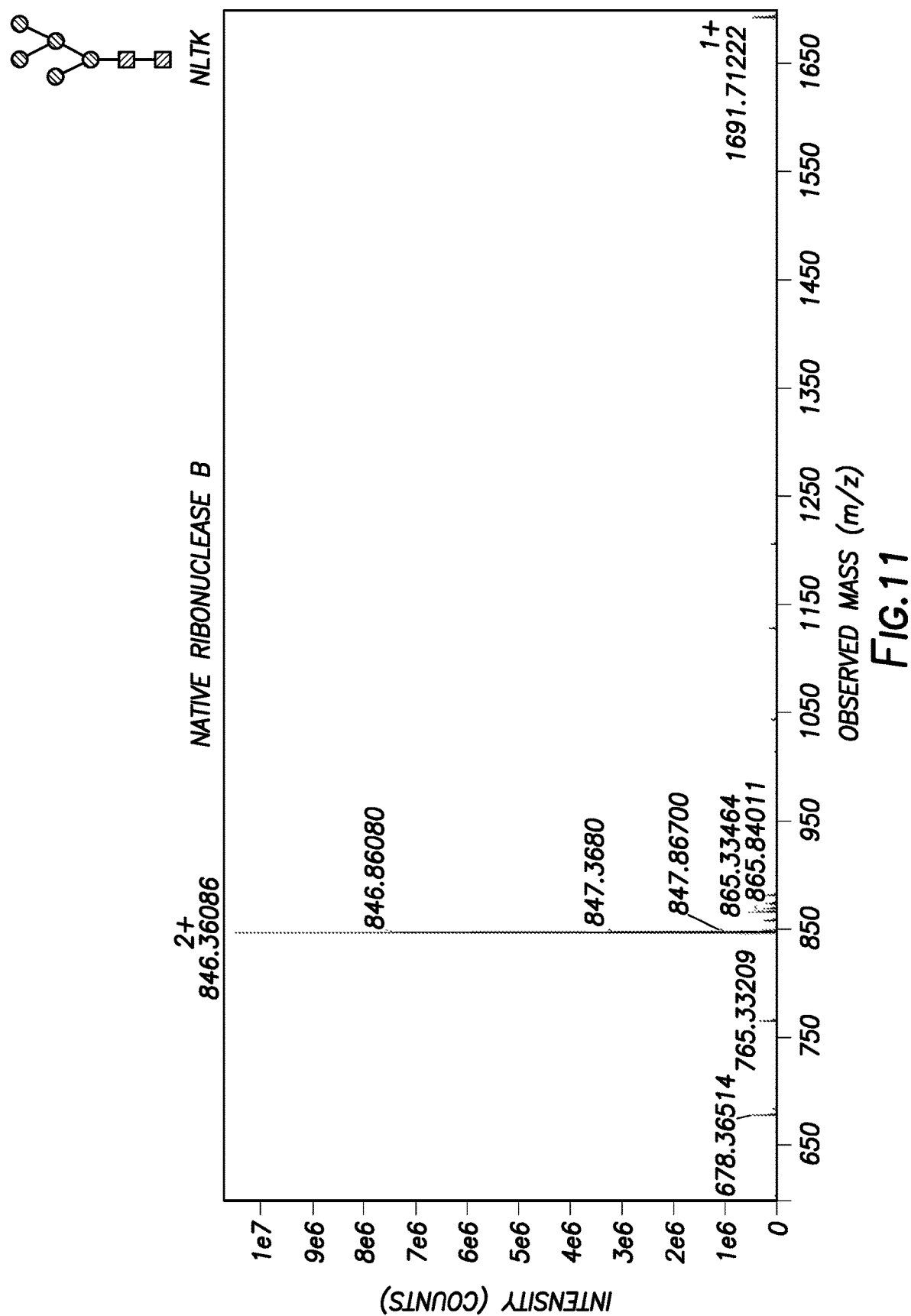
FIG. 11 shows an ESI mass spectrum of a native (un-derivatized) bovine ribonuclease B tryptic glycopeptide where generated ions were 1+ and 2+.

To generate more highly charged ions, the N-termini and lysine side chains were derivatized with a rapid glycan labelling molecule with a tertiary amino group in a simple one-step reaction. The reagent was directly added to an aliquot of the digest with no sample cleanup. Following the derivatization, ESI generated glycopeptides with additional higher charge states. For example, native glycopeptides of ribonuclease B were observed in the 1+ and 2+ charge states due to the short peptide length, while the derivatized analogues were detected as 2+ and 3+ ions. (FIG. 10 & FIG. 11). ESI of a native fetuin glycopeptide generated 4+ and 5+ ions predominantly, while the derivatized ones were observed as 3+-8+ ions. (FIG. 14). Additionally, the MS sensitivity was improved for many glycopeptides, by a factor of 3 to 5× being commonly observed.

The CID spectra of the more highly charged derivatized species were very similar to those of the native analytes. The ETD spectra of the native glycopeptides largely failed to produce significant peptide backbone fragmentation, as the m/z values were beyond the most effective ETD region. However, following derivatization, the ETD spectra appear to show enhanced fragmentation and allowed site-specific information to be obtained.

Derivatization of glycopeptides to improve their MS sensitivity and enhance charge states with optimized HILIC conditions allow their comprehensive characterization. As shown in FIGS. 10A and 10B, the comparison demonstrates that the derivatized glycopeptides resulted in mass spectral signals of approximately 203× those of the native glycopeptides. A similar trend was also observed for the integrated peak area. Increasing the signal intensity will increase the ability to detect and characterize low-abundance glycopeptides.

As shown in FIGS. 10 and 11, positive-mode ESI produced a 2+ ion for the native analyte, while the derivatized version produced significant amounts of the 3+ ion. We expected to see further charge-state enhancements for larger glycopeptides. Increasing the charge state of glycopeptides will significantly enhance their ETD fragmentation efficiency, allowing scientists to effectively fragment the peptide backbone, while leaving the glycan intact and attached to the peptide.

We claim:

1. A method of tagging a glycan for enhanced mass spectroscopy and fluorescence signals comprising the step of reacting the glycan with an amphipathic compound having a non-polar surface area of greater than about 200 Å$^2$ and a basic residue with a pKa greater than about 7 wherein a conjugate of the amphipathic compound and the glycan is formed, with the proviso that the amphipathic compound is not

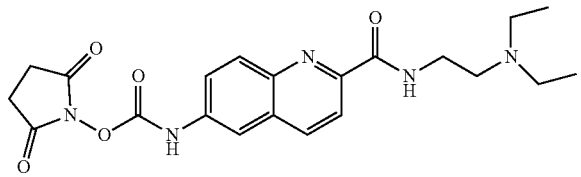 [SMILES: CCN(CC)CCNC(=O)c1ccc2cc(NC(=O)ON3C(=O)CCC3=O)ccc2n1]

and with the proviso that the amphipathic compound is not

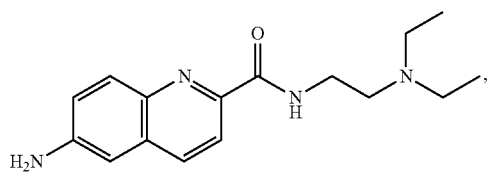 [SMILES: CCN(CC)CCNC(=O)c1ccc2cc(N)ccc2n1]

and analyzing the conjugate by positive ion mode electrospray ionization mass spectrometry.

2. The method according to claim 1 wherein the non-polar surface area is between about 200 Å$^2$ and about 1000 Å$^2$.

3. The method according to claim 1 wherein the non-polar surface area is between about 200 Å$^2$ and about 600 Å$^2$.

4. The method according to claim 1 wherein the non-polar surface area is between about 200 Å$^2$ and about 500 Å$^2$.

5. The method according to claim 1, wherein the amphipathic compound is a compound of Formula II:

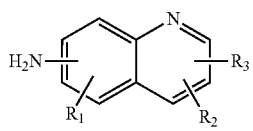

wherein
each of $R^1$ and $R^2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^3$ is

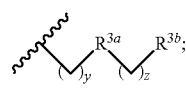

$R^{3a}$ is selected from ester, amide, amine, oxygen, urea, carbamate, carbonate, sulfur, thiourea, thiocarbamate, alkyl or carbonyl;
$R^{3b}$ is

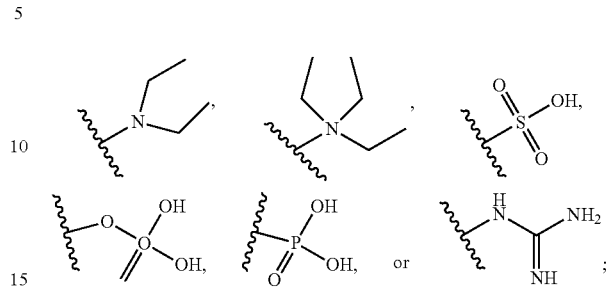

y=0-12;
z=1-12;
and salts or solvates thereof.

6. The method according to claim 5 wherein the glycan is selected from A2, FA2, M5, FA1G1, A2G1, FA2G1, FA2G2, FA2G1Ga1, FA2G2Ga1, FA2G2Sg1, FA2G1Ga2, FA2G2GaSg1, mannobiose (Man2), mannotriose (Man3), mannotetraose (Man4), mannopentaose (Man5), mannohexaose (Man6) and mannoheptaose (Man7).

7. The method according to claim 5 wherein the glycan is an O-linked glycan.

8. The method according to claim 1, wherein the amphipathic compound is a compound of Formula XI:

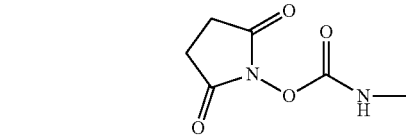

wherein
X=C or N
$R^1$ is O=C=N— or

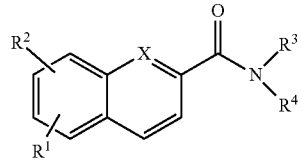

$R^2$ is independently selected from —H, —$C_1$-$C_8$ alkyl, —$C_1$-$C_8$ cycloalkyl, halo, dialkylamino, $CH_2$-dialkylamino, aminocarbonyl, alkoxycarbonyl, or alkoxy, but not Cl or O=C=N—; and
$R^3$ and $R^4$ are independently selected from —H, alkyl amino, wherein either $R^3$ or $R^4$ is alkylamino.

9. The method according to claim 8, wherein the glycan is selected from A2, FA2, M5, FA1G1, A2G1, FA2G1, FA2G2, FA2G1Ga1, FA2G2Ga1, FA2G2Sg1, FA2G1Ga2, FA2G2GaSg1, mannobiose (Man2), mannotriose (Man3), mannotetraose (Man4), mannopentaose (Man5), mannohexaose (Man6) and mannoheptaose (Man7).

10. The method according to claim 9, wherein the glycan is a N-linked glycan.

11. The method of claim 1, comprising forming the glycan by enzymatically digesting a glycoprotein.

12. The method of claim 1, wherein the conjugate is formed by reductive amination.

13. The method of claim 12, wherein the glycan is an O-linked glycan.

14. The method of claim 11, wherein the conjugate is subjected to electron transfer dissociation (ETD) mass spectrometry.

* * * * *